United States Patent
Harper et al.

(10) Patent No.: US 8,927,569 B2
(45) Date of Patent: *Jan. 6, 2015

(54) MACROCYCLIC COMPOUNDS AS ANTIVIRAL AGENTS

(75) Inventors: Steven Harper, Rome (IT); Vincenzo Summa, Rome (IT); Nigel J. Liverton, Harleysville, PA (US); John A. McCauley, Maple Glen, PA (US); John W. Butcher, Telford, PA (US); Marcello Di Filippo, Rome (IT); Maria Emilia Di Francesco, Rome (IT); Marco Ferrara, Rome (IT); Joseph J. Romano, Frederick, PA (US); Michael T. Rudd, Collegeville, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 639 days.

This patent is subject to a terminal disclaimer.

(21) Appl. No.: 12/668,987

(22) PCT Filed: Jul. 17, 2008

(86) PCT No.: PCT/GB2008/050585
§ 371 (c)(1),
(2), (4) Date: Jan. 13, 2010

(87) PCT Pub. No.: WO2009/010804
PCT Pub. Date: Jan. 22, 2009

(65) Prior Publication Data
US 2010/0183551 A1    Jul. 22, 2010

Related U.S. Application Data

(60) Provisional application No. 60/961,195, filed on Jul. 19, 2007, provisional application No. 60/964,090, filed on Aug. 9, 2007.

(51) Int. Cl.
| | |
|---|---|
| *A61K 31/44* | (2006.01) |
| *A61K 31/33* | (2006.01) |
| *C07D 245/00* | (2006.01) |
| *C07D 225/04* | (2006.01) |
| *C07D 295/00* | (2006.01) |
| *C07K 5/087* | (2006.01) |
| *C07K 5/083* | (2006.01) |

(52) U.S. Cl.
CPC .............. *C07K 5/0812* (2013.01); *C07K 5/0808* (2013.01)
USPC ........... 514/290; 514/281; 514/183; 540/454; 540/451; 540/450; 540/460; 540/461

(58) Field of Classification Search
USPC .......... 540/454, 451, 450, 460; 514/183, 281, 514/290
See application file for complete search history.

(56) References Cited

U.S. PATENT DOCUMENTS

| | | | |
|---|---|---|---|
| 3,480,613 A | 11/1969 | Walton | |
| 6,323,180 B1 | 11/2001 | Llinas-Brunet et al. | |
| 6,608,027 B1 | 8/2003 | Tsantrizos et al. | |
| 6,777,395 B2 | 8/2004 | Bhat et al. | |
| 6,955,174 B2 | 10/2005 | Friedrichs et al. | |
| 7,470,664 B2 | 12/2008 | Holloway et al. | |
| 8,138,164 B2 * | 3/2012 | Liverton et al. | 514/81 |
| 8,178,520 B2 * | 5/2012 | Di Francesco et al. | 514/183 |
| 2002/0019363 A1 | 2/2002 | Ismaili et al. | |
| 2002/0107138 A1 | 8/2002 | Hoveyda et al. | |
| 2003/0236216 A1 | 12/2003 | Devos et al. | |
| 2004/0006007 A1 | 1/2004 | Gosselin et al. | |
| 2004/0063658 A1 | 4/2004 | Roberts et al. | |
| 2004/0067901 A1 | 4/2004 | Bhat et al. | |

(Continued)

FOREIGN PATENT DOCUMENTS

| EP | 1719773 A1 | 11/2006 |
|---|---|---|
| GB | 2337262 A | 11/1999 |

(Continued)

OTHER PUBLICATIONS

Zeisel et al. "Hepatitis C virus entry: molecular mechanism and target for antiviral therapy<" Frontiers in Bioscience, 2009, vol. 14, pp. 3274-3285.*

(Continued)

*Primary Examiner* — Shengjun Wang
(74) *Attorney, Agent, or Firm* — Julie M. Lake; Laura M. Ginkel

(57) ABSTRACT

A class of macrocyclic compounds of formula (I), wherein $R^1$, $R^3$, $R^4$, $R^a$, $R^b$, A, Z, Y, X, M, W, n and m are defined herein, that are useful as inhibitors of viral proteases, particularly the hepatitis C virus (HCV) NS3 protease, are provided. Also provided are processes 5 for the synthesis and use of such macrocyclic compounds for treating or preventing HCV infection. Formula (I):

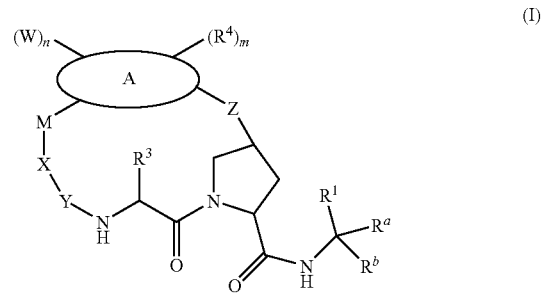

17 Claims, No Drawings

(56) References Cited

U.S. PATENT DOCUMENTS

| | | |
|---|---|---|
| 2004/0229776 A1 | 11/2004 | Chen et al. |
| 2004/0229818 A1 | 11/2004 | Llinas-Brunet |
| 2004/0254159 A1 | 12/2004 | Hasvold et al. |
| 2004/0266668 A1 | 12/2004 | Nakajima et al. |
| 2005/0020503 A1 | 1/2005 | Llinas-Brunet et al. |
| 2005/0038240 A1 | 2/2005 | Connolly et al. |
| 2006/0257980 A1 | 11/2006 | Li |
| 2007/0027071 A1 | 2/2007 | Holloway et al. |
| 2011/0028494 A1* | 2/2011 | Holloway et al. ............ 514/257 |

FOREIGN PATENT DOCUMENTS

| | | |
|---|---|---|
| GB | 2430621 A | 4/2007 |
| WO | 97/41211 A1 | 11/1997 |
| WO | 98/22496 A2 | 5/1998 |
| WO | 98/46630 A1 | 10/1998 |
| WO | 99/07733 A2 | 2/1999 |
| WO | 99/07734 A2 | 2/1999 |
| WO | 99/38888 A1 | 8/1999 |
| WO | 99/43691 A1 | 9/1999 |
| WO | 99/50230 A1 | 10/1999 |
| WO | 99/64442 A1 | 12/1999 |
| WO | 00/09543 A2 | 2/2000 |
| WO | 00/09546 A2 | 2/2000 |
| WO | 00/25780 A1 | 5/2000 |
| WO | 00/59929 A1 | 10/2000 |
| WO | 01/00622 A1 | 1/2001 |
| WO | 01/47883 A1 | 7/2001 |
| WO | 01/60379 A1 | 8/2001 |
| WO | 01/68663 A1 | 9/2001 |
| WO | 01/77091 A2 | 10/2001 |
| WO | 01/77113 A2 | 10/2001 |
| WO | 01/79246 A2 | 10/2001 |
| WO | 01/90121 A2 | 11/2001 |
| WO | 01/92282 A2 | 12/2001 |
| WO | 02/04425 A1 | 1/2002 |
| WO | 02/06246 A1 | 1/2002 |
| WO | 02/18404 A2 | 3/2002 |
| WO | 02/20497 A1 | 3/2002 |
| WO | 02/32920 A2 | 4/2002 |
| WO | 02/48116 A2 | 6/2002 |
| WO | 02/48165 A2 | 6/2002 |
| WO | 02/48172 A2 | 6/2002 |
| WO | 02/051425 A1 | 7/2002 |
| WO | 02/057287 A2 | 7/2002 |
| WO | 02/057425 A2 | 7/2002 |
| WO | 02/100415 A2 | 12/2002 |
| WO | 03/015755 A1 | 2/2003 |
| WO | 03/026589 A2 | 4/2003 |
| WO | 03/026675 A1 | 4/2003 |
| WO | 03/062192 A1 | 7/2003 |
| WO | 03/062211 A1 | 7/2003 |
| WO | 03/064455 A2 | 8/2003 |
| WO | 03/068244 A1 | 8/2003 |
| WO | 03/093290 A2 | 11/2003 |
| WO | 03/099274 A1 | 12/2003 |
| WO | 04/000858 A2 | 12/2003 |
| WO | 2004/002422 A2 | 1/2004 |
| WO | 2004/002999 A2 | 1/2004 |
| WO | 2004/003000 A2 | 1/2004 |
| WO | 2004/003138 A2 | 1/2004 |
| WO | 2004/007512 A2 | 1/2004 |
| WO | 2004/011478 A2 | 2/2004 |
| WO | 2004/013300 A2 | 2/2004 |
| WO | 2004/028481 A2 | 4/2004 |
| WO | 2004/041201 A2 | 5/2004 |
| WO | 2004/087714 A1 | 10/2004 |
| WO | 2004/093915 A1 | 11/2004 |
| WO | 2004/103996 A1 | 12/2004 |
| WO | 2004/110442 A1 | 12/2004 |
| WO | 2005/003147 A2 | 1/2005 |
| WO | 2005/016927 A1 | 2/2005 |
| WO | 2005/023819 A1 | 3/2005 |
| WO | 2005/034941 A1 | 4/2005 |
| WO | 2005/046712 A1 | 5/2005 |
| WO | 2005/070955 A1 | 8/2005 |
| WO | 2005/080399 A1 | 9/2005 |
| WO | 2006/008556 A1 | 1/2006 |
| WO | 2006/020082 A1 | 2/2006 |
| WO | 2006/021341 A1 | 3/2006 |
| WO | 2006/027628 A2 | 3/2006 |
| WO | 2006/029912 A1 | 3/2006 |
| WO | 2006/046030 A1 | 5/2006 |
| WO | 2006/046039 A2 | 5/2006 |
| WO | 2006/119061 A2 | 11/2006 |
| WO | 2006/119975 A1 | 11/2006 |
| WO | 2007/015787 A1 | 2/2007 |
| WO | 2007/015855 A1 | 2/2007 |
| WO | 2007/016441 A1 | 2/2007 |
| WO | 2007/028789 A1 | 3/2007 |
| WO | 2007/029029 A2 | 3/2007 |
| WO | 2007/131966 A1 | 11/2007 |
| WO | 2007/145894 A2 | 12/2007 |
| WO | 2007/148135 A1 | 12/2007 |
| WO | 2008/051475 A2 | 5/2008 |
| WO | 2008/051477 A2 | 5/2008 |
| WO | 2008/057028 A1 | 5/2008 |
| WO | 2008/057208 A2 | 5/2008 |
| WO | 2008/057209 A1 | 5/2008 |
| WO | 20088051514 A2 | 5/2008 |
| WO | 2008/112108 A1 | 9/2008 |
| WO | 2009/005687 A1 | 1/2009 |
| WO | 2009/010804 A1 | 1/2009 |
| WO | 2009/064955 A1 | 5/2009 |
| WO | 2009/064975 A1 | 5/2009 |

OTHER PUBLICATIONS

Youwei Yan et al., Complex of NS3 protease and NS4A peptide of BK strain hepatitis C virus: A 2.2 Angstrom resolution structure in a hexagonal crystal form, 7 Protein Science 837 (1998).

Youla S. Tsantrizos, The Design of a Potent Inhibitor of the Hepatitis C Virus NS3 Protease: BILN 2061—From the NMR Tube to the Clinic, Biopolymers (Peptide Science), vol. 76, pp. 309-323 (2004).

International Preliminary Report on Patentability, International Application No. PCT/US2009/040815, dated Nov. 2, 2010.

Brian W Dymock et al., "Novel Approaches to the Treatment of Hepatitis C Virus Infection," 11 Antiviral Chemistry & Chemotherapy 79-96 (2000).

Hugo R. Rosen & David R. Gretch, "Hepatitis C virus: current understanding and prospects for future therapies," 5 Molec. Med. Today 393-99 (1999).

Darius Moradpour & Hubert E Blum, "Current and evolving therapies for hepatitis C," 11 Euro. J. Gastroenterol. Hepatol. 1189-1202 (1999).

Ralf Bartenschlager, "Candidate Targets for Hepatitis C Virus-Specific Antiviral Therapy," 40(5-6) Intervirology 378-93 (1997).

Georg M. Lauer & Bruce D. Walker, "Hepatitis C Virus Infection," 345(1) N. Engl. J. Med. 41-52 (2001); correction: 345 (19) N. Engl. J. Med. 1425-26 (2001).

Brain W. Dymock, "Emerging therapies for hepatitis C virus infection," 6 Emerging Drugs 13-42 (2001).

Charlene Crabb, Infectious Diseases. "Hard-Won Advances Spark Excitement about Hepatitis C," Science 506-507 (2001).

Rogers E. Harry-O'Kuru et al., "A Short, Flexible Route toward 2'-C-Branched Ribonucleosides," 62 J. Org. Chem. 1754-59 (1997).

Michael S. Wolfe & Rogers E. Harry-O'Kuru, "A Concise Synthesis of 2'-C-Methylribonucleosides," 36(42) Tetrahedron Letters 7611-14 (1995).

Scott J. Miller et al., "Application of Ring-Closing Metathesis to the Synthesis of Rigidified Amino Acids and Peptides," 118 J. Am. Chem. Soc. 9606-14 (1996).

Jason S. Kingsbury et al., "A Recyclable Ru-Based Metathesis Catalyst," 121 J. Am. Chem. Soc. 791-99 (1999).

Matthias Scholl et al., "Synthesis and Activity of a New Generation of Ruthenium-Based Olefin Metathesis Catalysts Coordinated with 1,3-Dimesityl-4,5-dihydroimidazol-2-ylidene Ligands," 1(6) Organic Letters 953-56 (1999).

(56) References Cited

OTHER PUBLICATIONS

Alois Furstner et al., "Total Synthesis and Structural Refinement of the Cyclic Tripyrrole Pigment Nonylprodigiosin," 64 J. Org. Chem. 8275-80 (1999).
Tina M. Trnka & Robert H. Grubbs, "The Development of L2X2R-CHR Olefin Metathesis Catalysts: An Organometallic Success Story," 34 Acc. Chem. Res. 18-29 (2001).
A. Srikrishna et al., "Enantiospecific Construction of the BC-ring System of Taxanes," 45 Tetrahedron Letters 2939-42 (2004).
Yung-Son Hon et al., "Dibromomethane as one-carbon source in organic synthesis: a versatile methodology to prepare the cyclic and acyclic alpha-methylene or alpha-keto acid derivatives from the corresponding terminal alkenes," 60 Tetrahedron 4837-60 (2004).
Eusebio Juaristi & Hugo A. Jimenez-Vazquez, "Single Electron Transfer Mechanism in the Reaction of 1,3-Dithianyllithium and Alkyl Iodides," 56 J. Org. Chem. 1623-30 (1991).
Paola Conti et al., "Chemoenzymatic Synthesis of the Enantiomers of Desoxymuscarine," 9 Tetrahedron: Asymmetry 657-65 (1998).
Robert M. Coates & Mark W. Johnson, "Stereoselective Synthesis of Moenocinol and Assignment of Its Carbon-13 Nuclear Magnetic Resonance Spectrum," 45 J. Org. Chem. 2685-97 (1980).
D. Becker & N. Haddad, "Steric Effects in Intramolecular [2+2] Photocycloaddition of C=C Double Bonds to Cyclohexenones," 49(4) Tetrahedron 947-64 (1993).
Richard A. Bunce et al., "Tandem SN2-Michael Reactions for the Preparation of Simple Five- and Six-Membered-Ring Nitrogen and Sulfur Heterocycles," 57 J. Org. Chem. 1727-33 (1992).
Masao Tokuda et al., "Aminyl Radical Cyclization by Means of Anodic Oxidation. Stereoselective Synthesis of cis-1-Methyl-2,5-Disubstituted Pyrrolidines," 26(49) Tetrahedron Letters 6085-88 (1985).
Robert Haner et al., "174. Generation and Reactions of Lithiated tert-Butyl and 2,6-Di(tert-butyl)-4-methylphenyl Cyclopropanecarboxylates," 69 Helvetica Chimica Acta 1655-65 (1986).
Herbert O. House et al., "Cyclization of Unsaturated Hydroxylamine Derivatives," 41(5) J. Org. Chem. 855-63 (1976).
Theophil Eicher et al., "Bryophyte Constituents; 7: New Synthesis of (+)-Rosmarinic Acid and Related Compounds," Synthesis 755-62 (Jun. 1996).
Michael C. Venuti et al., "Inhibitors of Cyclic AMP Phosphodiesterase. 3. Synthesis and Biological Evaluation of Pyrido and Imidazolyl Analogues of 1,2,3,5-Tetrahydro-2-oxoimidazo[2,1-b]quinazoline," 31 J. Med. Chem. 2136-45 (1988).
Marc-Andre Poupart et al., "Solid-Phase Synthesis of Peptidomimetic Inhibitors for the Hepatitis C Virus NS3 Protease," 66(14) J. Org. Chem. 4743-51 (2001).
Nigel J. Liverton et al., Molecular Modeling Based Approach to Potent P2-P4 Macrocyclic Inhibitors of Hepatitis C NS3/NS4A Protease, 130 J. Am. Chem. Soc. 4607-09 (2008).
Anthony C. Allison & Elsie M. Eugui, "Immunosuppressive and other anti-rheumatic activities of mycophenolate mofetil," 44 Agents and Actions Supplements 165-88 (1993).
Joel Kirschbaum, "Amantadine," 12 Profiles of Drug Substances, Excipients and Related Methodology 1-36 (1983).
T. K. Chakaborty et al., "Alpha-Phenylglycinol as chiral auxilliary in diastereoselective Strecker synthesis of alpha-amino acids," 51(33) Tetrahedron 9179-90 (1995).
W. Clark Still et al., "Rapid Chromatographic Technique for Preparative Separations with Moderate Resolution," 43(14) J. Org. Chem. 2923-25 (1978).
Michael D. Cooke et al., :The occurrence of a hydride shift in the aromatization of 1,4-epoxy-1,2-dihydronaphthalenes, 11 J. Chem. Soc. Perkin Trans. I: Phys. Org. Chem. 1377 (1984).
Paul Aeberli et al., "Neuropharmacological investigation of N-benzylsulfamides," 10(4) J. Med. Chem. 636-42 (1967).
Nathalie Goudreau & Montse Llinas-Brunet, "The Therapeutic Potential of NS3 Protease Inhibitors in HCV Infection," 14(9) Expert Opinion 1129-44 (2005).
Volker Lohmann et al., "Selective Stimulation of Hepatitis C Virus and Pestivirus NS5B RNA Polymerase Activity by GTP," 274(16) J. Bio. Chem. 10807-15 (1999).
V. Lohmann et al., "Replication of Subgenomic Hepatitis C Virus RNAs in a Hepatoma Cell Line," 285 Science 110-13 (1999).
Kevin X. Chen et al. "Novel Potent Hepatitis C Virus NS3 Serine Protease Inhibitors Derived from Proline-Based Macrocycles," 49 J. Med. Chem. 995-1005 (2006).
Yuri Goldberg et al., "Highly regioselective bromination of 2,3-dimethylanisole with N-bromosuccinimide," 57 J. Org. Chem. 6374-76 (1992).
Manfred Schlosser et al., "8-Methoxyisoquinoline derivatives through ortho-selective metallation of 2-(3-methoxyphenyl)ethylamines," 32(17) Tetrahedron Letters 1965-66 (1991).
Angela Casini et al., "Carbonic Anhydrase inhibitors inhibition of cytosolic isozymes I and II with sulfamide derivatives," 13(5) Bioorg. Med. Chem. Lett. 837-40 (2003).
Kiyotaka Onisuka et al., "A novel route to 2,3-disubstituted indoles via palladium-catalyzed three-component coupling of aryl iodide, o-alkenylphenyl isocyanide and amine," 43 Tetrahedron Letters 6197-99 (2002).
Duane E. Rudisill & J. K. Stille, "Palladium-catalyzed synthesis of 2-substituted indoles," 54(25) J. Org. Chem. 5856-66 (2002).
Makoto Satoh et al., "Palladium-Catalyzed Cross-Coupling Reaction of (1-Ethoxy-1-alken-2-yl)boranes With ortho-Functionalized Iodoarenes. A Novel and Convenient Synthesis of Benzo-Fused Heteroaromatic Compounds," Synthesis Communications 373-377 (Apr. 1987).
Yuusaku Yokoyama et al., "Palladium-Catalyzed Reaction of 3-Bromoindole Derivative with Allyl Esters in the Presence of Hexan-butyldistannane," 31(8) Heterocycles 1505-11 (1990).
Steven W. Ludmerer et al., "A transient cell-based phenotype assay for hepatitis C NS3/4A protease: Application to potency determinations of a novel macrocyclic inhibitor against diverse protease sequences isolated from plasma infected with HCV," 151 Journal of Virological Methods 301-07 (2008).
John A. McCauley et al., "Bismacrocyclic Inhibitors of Hepatitis C NS314a Protease," 47 Angew. Chem. Int. Ed. 9104-07 (2008).
Ashok Arasappan et al., "P2-P4 Macrocyclic inhibitors of hepatitis C virus NS3-4A serine protease," 16 Bioorganic & Medicinal Chemistry Letters 3960-65 (2006).

\* cited by examiner

```
                        SEQUENCE LISTING

<160> NUMBER OF SEQ ID NOS: 1

<210> SEQ ID NO 1
<211> LENGTH: 11
<212> TYPE: PRT
<213> ORGANISM: Artificial Sequence
<220> FEATURE:
<223> OTHER INFORMATION: Protease Substrate
<221> NAME/KEY: ACETYLATION
<222> LOCATION: 1
<221> NAME/KEY: AMIDATION
<222> LOCATION: 11
<221> NAME/KEY: SITE
<222> LOCATION: 1
<223> OTHER INFORMATION: Europium Label
<221> NAME/KEY: MOD_RES
<222> LOCATION: 7
<223> OTHER INFORMATION: Xaa = Abu
<221> NAME/KEY: SITE
<222> LOCATION: 8
<223> OTHER INFORMATION: Xaa = 2-hydroxy propanoic acid
<221> NAME/KEY: SITE
<222> LOCATION: (11)...(11)
<223> OTHER INFORMATION: QSY-y label
<221> NAME/KEY: THIOLEST
<222> LOCATION: (7)...(8)

<400> SEQUENCE: 1

Cys Asp Asp Met Glu Glu Xaa Xaa Ser Ala Lys
 1               5                  10
```

MACROCYCLIC COMPOUNDS AS ANTIVIRAL AGENTS

CROSS-REFERENCE TO RELATED APPLICATIONS

This application is a National Stage application of International Patent Application No. PCT/GB2008/050585, filed Jul. 17, 2008, which claims priority to U.S. Provisional Patent Application No. 60/961,195, filed Jul. 19, 2007, and to U.S. Provisional Patent Application No. 60/964,090, filed Aug. 9, 2007.

FIELD OF THE INVENTION

The present invention relates to macrocyclic compounds that are useful as inhibitors of the hepatitis C virus (HCV) NS3 protease, their synthesis, and their use for treating or preventing HCV infection.

BACKGROUND OF THE INVENTION

Hepatitis C virus (HCV) infection is a major health problem that leads to chronic liver disease, such as cirrhosis and hepatocellular carcinoma, in a substantial number of infected individuals, estimated to be 2-15% of the world's population. According to the World Health Organization, there are more than 170 million infected individuals worldwide, with at least 3 to 4 million people being infected each year. Once infected, about 20% of people clear the virus, but the rest harbor HCV the rest of their lives. Ten to twenty percent of chronically infected individuals eventually develop liver-destroying cirrhosis or cancer. The viral disease is transmitted parenterally by contaminated blood and blood products, contaminated needles, or sexually and vertically from infected mothers or carrier mothers to their offspring.

Current treatments for HCV infection, which are restricted to immunotherapy with recombinant interferon-α alone or in combination with the nucleoside analog ribavirin, are of limited clinical benefit. Moreover, there is no established vaccine for HCV. Consequently, there is an urgent need for improved therapeutic agents that effectively combat chronic HCV infection.

Several virally-encoded enzymes are putative targets for therapeutic intervention, including a metalloprotease (NS2-3), a serine protease (NS3), a helicase (NS3), and an RNA-dependent RNA polymerase (NS5B). The NS3 protease is located in the N-terminal domain of the NS3 protein, and is considered a prime drug target since it is responsible for an intramolecular cleavage at the NS3/4A site and for downstream intermolecular processing at the NS4A/4B, NS4B/5A and NS5A/5B junctions. Previous research has identified classes of peptides, such as hexapeptides as well as tripeptides discussed in U.S. patent application publication nos. US2005/0020503, US2004/0229818, and US2004/0229776, showing degrees of activity in inhibiting the NS3 protease. The aim of the present invention is to provide further compounds which exhibit activity against the HCV NS3 protease.

Macrocyclic compounds that exhibit activity against the HCV NS3 protease have already been disclosed in International patent application publication nos. WO2006/119061, WO2007/015855 and WO2007/016441 (all Merck & Co., Inc.),

SUMMARY OF THE INVENTION

Thus, in one aspect, there is provided the compound of formula (I):

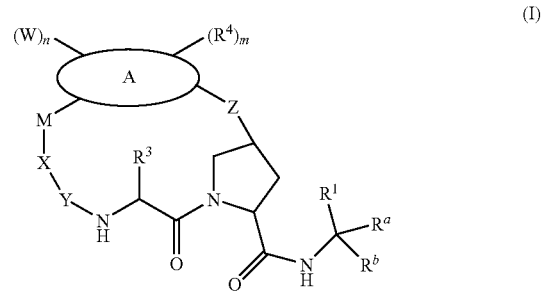

or a pharmaceutically acceptable salt thereof,
wherein:
m is 0, 1, 2 or 3;
n is 0, 1 or 2;
$R^1$ is $CO_2R^5$, $CONR^5SO_2R^5$, $CONR^5SO_2N(R^5)_2$ or tetrazolyl;
$R^a$ is $C_{2-6}$alkylene-$R^2$;
$R^b$ is hydrogen;
or $R^a$ and $R^b$, together with the carbon atom to which they are attached, form a $C_{3-6}$cycloalkyl group, optionally substituted by $R^2$;
$R^2$ is $C_{1-6}$alkyl, $C_{2-6}$alkenyl or $C_{3-8}$cycloalkyl, wherein said alkyl, alkenyl or cycloalkyl is optionally substituted with 1 to 3 halo;
$R^3$ is $C_{1-6}$alkyl, $(CH_2)_{0-3}C_{3-8}$cycloalkyl, $(CH_2)_{0-3}$aryl or $(CH_2)_{0-3}$Het, optionally substituted by halo, $OR^5$, $SR^5$, $N(R^5)_2$, $C_{1-6}$alkyl, $NO_2$, CN, $CF_3$, $NR^5SO_2R^5$, $SO_2N(R^5)_2$, $NHCO_2R^5$, $NHCOR^5$, $NHCONHR^5$, $CO_2R^5$, $C(O)R^5$ or $CON(R^5)_2$;
each $R^5$ is independently hydrogen, $C_{1-6}$alkyl or $C_{3-8}$cycloalkyl;
each W is independently halo, $OR^5$, $C_{1-6}$alkyl, CN, $NO_2$, $CF_3$, $CO_2R^5$, $CON(R^5)_2$, $COR^5$, $NR^5C(O)R^5$, aryl or heteroaryl;
Z is O or $NR^6$;
$R^6$ is hydrogen or $C_{1-6}$alkyl;
Y is C=O, $SO_2$ or $CR^cR^d$;
X is O, $NR^e$ or $CR^eR^f$;
$R^c$, $R^d$, $R^e$ and $R^f$ are independently hydrogen, halo or $C_{1-6}$alkyl;
M is $C_{4-12}$alkylene, $C_{4-12}$alkenylene or $C_{4-12}$alkynylene, optionally substituted by $C_{1-6}$alkyl, $(CH_2)_{0-3}C_{3-8}$cycloalkyl, $(CH_2)_{0-3}$aryl, and optionally containing one O or S atom or one NH or $NC_{1-6}$alkyl group, and optionally spiro-fused to a $C_{3-7}$cycloalkyl group, and optionally fused to a 3- to 8-membered ring, which ring optionally contains 1 or 2 heteroatoms selected from N, O and S;
ring A is a 8- to 10-membered fused heterobicyclic ring system containing 1 to 4 heteroatoms selected from N, O and S, where one and only one of the rings of the heterobicyclic ring system is fused to a 5- or 6-membered ring, which ring may optionally contain 1 or 2 heteroatoms selected from N, O and S; and
$R^4$ is halo, hydroxy, $C_{1-6}$alkyl, $C_{1-6}$alkoxy, CN, $NO_2$, oxo, $C_{3-8}$cycloalkyl, $N(R^5)_2$, aryl or heteroaryl, optionally substituted by 1 to 8 halo or $C_{1-4}$alkyl.

DETAILED DESCRIPTION OF THE INVENTION

In one embodiment of the present invention, m is 0 or 1.
In another embodiment of the present invention, n is 0 or 1.

In another embodiment, R' is CONR$^5$SO$_2$R$^5$ or CONR$^5$SO$_2$N(R$^5$)$_2$ where R$^5$ is as hereinbefore defined. Preferably, R$^1$ is CONR$^5$SO$_2$R$^5$ where R$^5$ is as hereinbefore defined. More preferably, R$^1$ is CONHSO$_2$R$^5$ where R$^5$ is as hereinbefore defined. Especially, R$^1$ is CONHSO$_2$—C$_{3-8}$cycloalkyl. More especially, R$^1$ is CONHSO$_2$—C$_{3-6}$cycloalkyl. Most especially, R$^1$ is CONHSO$_2$-cyclopropyl.

In another embodiment, R$^a$ is C$_{2-5}$alkylene-R$^2$ where R$^2$ is as hereinbefore defined. Preferably, R$^a$ is C$_{2-4}$alkylene-R$^2$ where R$^2$ is C$_{1-6}$alkyl, optionally substituted with 1 to 3 halo. More preferably, R$^a$ is C$_{2-3}$alkylene-R$^2$ where R$^2$ is C$_{1-4}$alkyl, optionally substituted with 1 to 3 fluoro or chloro. Most preferably, R$^a$ is ethylene-R$^2$ where R$^2$ is C$_{1-2}$alkyl, optionally substituted by 1 to 3 fluoro. Especially, R$^a$ is ethylene-R$^2$ where R$^2$ is difluoromethyl or trifluoromethyl.

In another embodiment, R$^a$ and R$^b$, together with the carbon atom to which they are attached, form a C$_{3-5}$cycloalkyl group, optionally substituted by R$^2$, where R$^2$ is C$_{1-6}$alkyl or C$_{2-6}$alkenyl. Preferably, R$^a$ and R$^b$, together with the carbon atom to which they are attached form a C$_{3-4}$cycloalkyl group, substituted by C$_{1-4}$alkyl or C$_{2-4}$alkenyl. More preferably, R$^a$ and R$^b$, together with the carbon atom to which they are attached, form a cyclopropyl group, substituted by —CH═CH$_2$.

In another embodiment, R$^3$ is C$_{1-6}$alkyl, or (CH$_2$)$_{0-3}$C$_{3-8}$cycloalkyl, optionally substituted by halo, OR$^5$ or C$_{1-6}$alkyl, where R$^5$ is as hereinbefore defined. Preferably, R$^3$ is C$_{1-6}$alkyl or (CH$_2$)$_{0-3}$C$_{3-8}$cycloalkyl. More preferably, R$^3$ is C$_{1-4}$alkyl or C$_{3-6}$cycloalkyl. Most preferably, R$^3$ is C$_{3-4}$alkyl or C$_{5-6}$cycloalkyl. Especially, R$^3$ is $^n$butyl, $^t$butyl, cyclopentyl or cyclohexyl.

In another embodiment, each W is independently halo, OR$^5$, C$_{1-6}$alkyl, CN, NO$_2$, CF$_3$, CO$_2$R$^5$ or CON(R$^5$)$_2$, where R$^5$ is as hereinbefore defined. Preferably, each W is independently halo, OC$_{1-6}$alkyl, C$_{1-6}$alkyl, CN, NO$_2$ or CF$_3$. More preferably, each W is independently OC$_{1-4}$alkyl or C$_{1-4}$alkyl. Most preferably, W is OC$_{1-2}$alkyl or C$_{1-2}$alkyl. Especially, W is methoxy or methyl.

In another embodiment, Z is O.

In another embodiment Y is C═O.

In another embodiment, X is O or NR$^e$, where R$^e$ is as hereinbefore defined. Preferably, X is O or NC$_{1-4}$alkyl. More preferably, X is O or NC$_{1-2}$alkyl. Most preferably, X is O or NCH$_3$.

In another embodiment, M is C$_{4-10}$alkylene, C$_{4-10}$alkenylene or C$_{4-10}$alkynylene, optionally substituted by C$_{1-6}$alkyl or (CH$_2$)$_{0-3}$C$_{3-8}$cycloalkyl, and optionally containing one O or S group or one NH or NC$_{1-4}$alkyl group, and optionally fused to a 3- to 8-membered carbocyclic ring. Preferably, M is C$_{5-8}$alkylene or C$_{5-8}$alkenylene, optionally substituted by C$_{1-4}$alkyl, and optionally fused to C$_{3-6}$cycloalkyl. More preferably, M is C$_{5-8}$alkylene or C$_{5-8}$alkenylene, optionally substituted by C$_{1-2}$alkyl, and optionally fused to C$_{5-6}$cycloalkyl. Most preferably, M is C$_{5-8}$alkylene or C$_{5-8}$alkenylene, optionally substituted by methyl, and optionally fused to cyclopentyl. Examples of suitable M groups are: octylene,

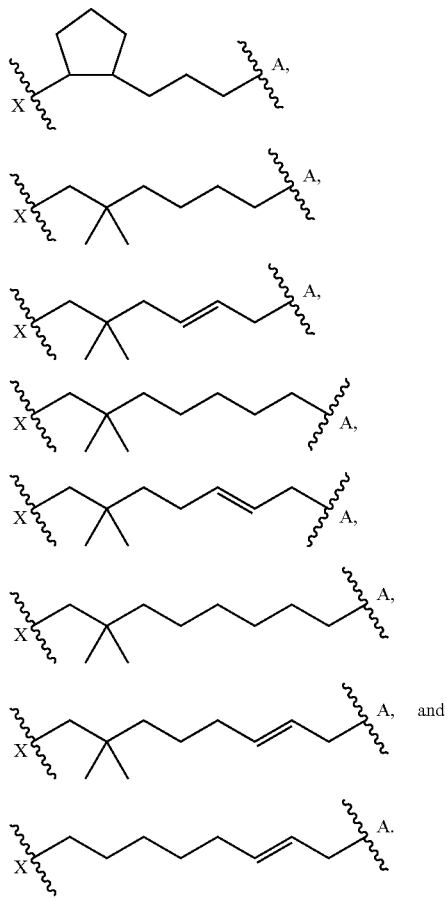

In another embodiment, A is a 9- or 10-membered fused heterobicyclic ring system containing 1 to 3 heteroatoms selected from N and O, where one and only one of the rings of the heterobicyclic system is fused to a 5- or 6-membered ring, which ring may optionally contain 1 or 2 heteroatoms selected from N and S, and which ring is optionally substituted by R$^4$, where R$^4$ is as hereinbefore defined. Preferably, A is a 9- or 10-membered fused heterobicyclic ring system containing 1 or 2 N atoms, where one and only one of the rings of the heterobicyclic system is fused to a 5- or 6-membered ring, which ring may optionally contain one S atom or two N atoms, and which ring is optionally substituted by R$^4$, where R$^4$ is as hereinbefore defined. Examples of suitable A groups, optionally substituted by R$^4$, are:

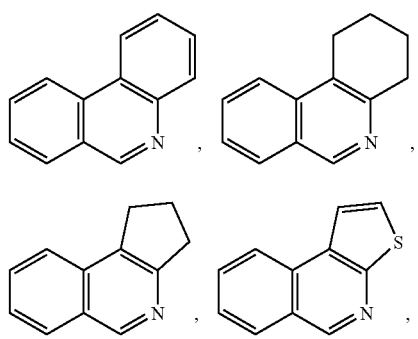

-continued

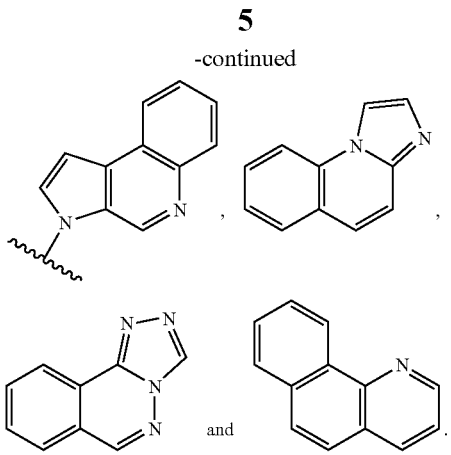

In another embodiment, when $R^4$ is present, $R^4$ is halo, hydroxy, $C_{1-6}$alkyl, $C_{1-6}$alkoxy, CN, $C_{3-8}$cycloalkyl or aryl. Preferably, $R^4$ is fluoro, chloro, bromo, $C_{1-4}$alkyl, $C_{1-4}$alkoxy, CN or phenyl. Most preferably, $R^4$ is fluoro, chloro, $C_{1-2}$alkyl, $C_{1-2}$alkoxy or CN. Especially, $R^4$ is fluoro, chloro, methyl, methoxy or CN.

In another embodiment of the present invention, there is provided the compound of formula (Ia):

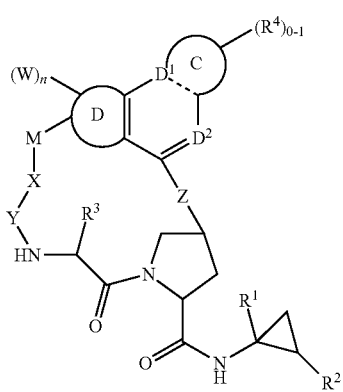

or a pharmaceutically acceptable salt thereof, wherein $R^1$, $R^2$, $R^3$, $R^4$, W, n, X, Y, Z and M are as defined in relation to formula (I);

$D^1$ is C and $D^2$ is N and the dotted line represents a double bond;

or $D^1$ is N and $D^2$ is CH and the dotted line represents a single bond;

ring C is a 5- or 6-membered ring optionally containing 1 or 2 heteroatoms selected from N and S; and ring D is a 5- or 6-membered ring optionally containing one or two N atoms.

Preferably, ring C is a 5- or 6-membered ring optionally containing 1 or 2 N atoms or one S atom. Examples of suitable C groups are phenyl, cyclohexenyl, cyclopentenyl, thienyl and imidazolyl. Preferably, ring D is a 5- or 6-membered ring optionally containing one N atom. Examples of suitable D groups are phenyl and pyrrolyl.

In another embodiment of the present invention, there is provided the compound of formula (Iaa):

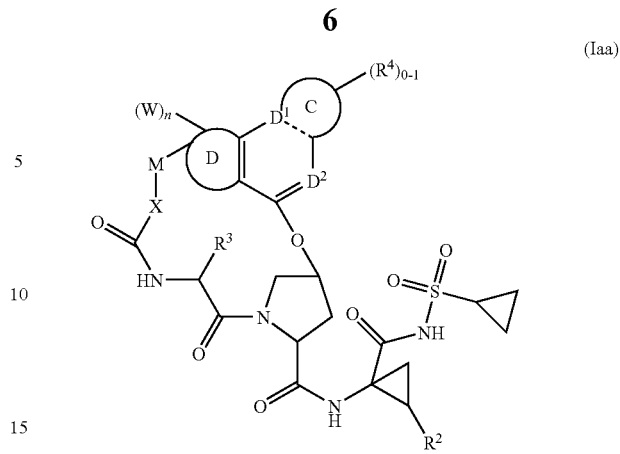

or a pharmaceutically acceptable salt thereof, wherein $R^2$, $R^3$, $R^4$, W, n, X, M, $D^1$, $D^2$, ring C and ring D are as defined in relation to formula (Ia).

In another embodiment of the present invention, there is provided the compound of formula (Iab):

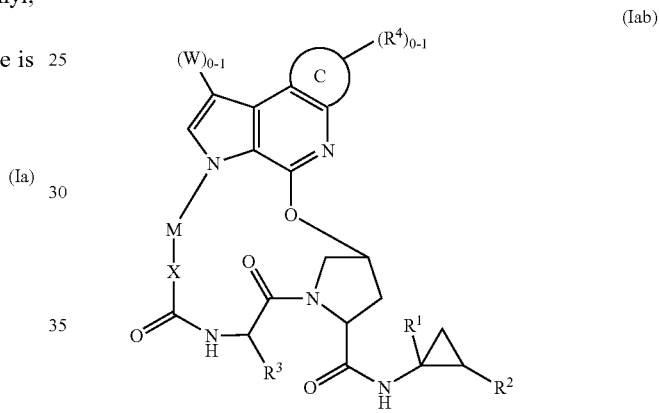

or a pharmaceutically acceptable salt thereof, wherein $R^1$, $R^2$, $R^3$, $R^4$, W, X, M and ring C are as defined in relation to formula (Ia).

In another embodiment of the present invention, there is provided the compound of formula (Iad):

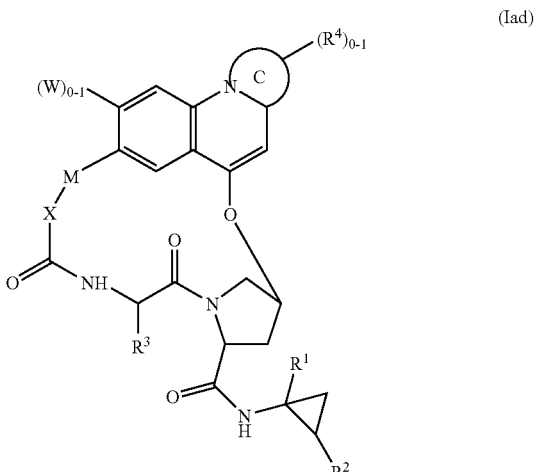

or a pharmaceutically acceptable salt thereof, wherein $R^1$, $R^2$, $R^3$, $R^4$, W, X, M and ring C are as defined in relation to formula (Ia).

In another embodiment of the present invention, there is provided the compound of formula (Iae):

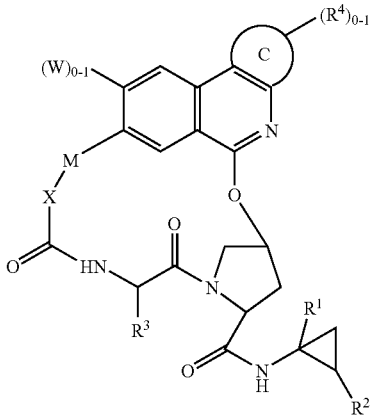

(Iae)

or a pharmaceutically acceptable salt thereof, wherein $R^1$, $R^2$, $R^3$, $R^4$, W, X, M and ring C are as defined in relation to formula (Ia).

In another embodiment of the present invention, there is provided the compound of formula (Ib):

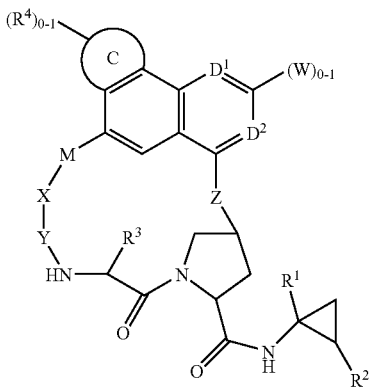

(Ib)

or a pharmaceutically acceptable salt thereof, wherein $R^1$, $R^2$, $R^3$, $R^4$, W, X, Y, Z and M are as defined in relation to formula (I);

one of $D^1$ and $D^2$ is CH and the other of $D^1$ and $D^2$ is N; and ring C is a 5- or 6-membered ring optionally containing 1 or 2 heteroatoms selected from N and S.

Preferably, ring C is a 5- or 6-membered ring optionally containing one N or S atom. An example of a suitable C group is phenyl.

In another embodiment of the present invention, there is provided the compound of formula (Iba):

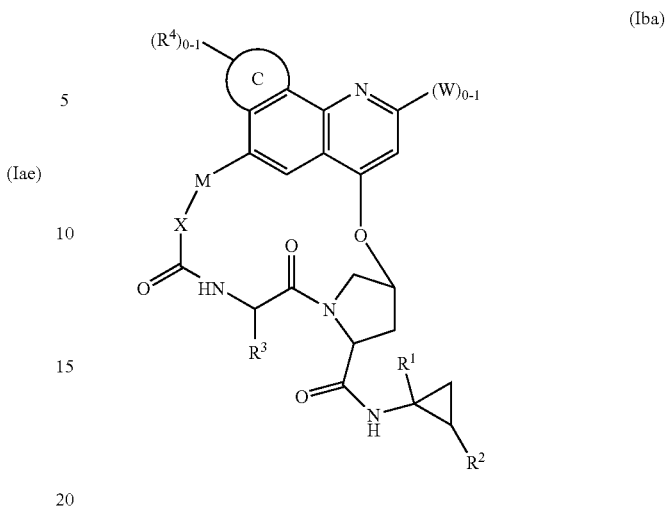

(Iba)

or a pharmaceutically acceptable salt thereof, wherein $R^1$, $R^2$, $R^3$, $R^4$, W, X, M and ring C are as defined in relation to formula (Ib).

When any variable occurs more than one time in formula (I) or in any substituent, its definition on each occurrence is independent of its definition at every other occurrence.

As used herein, the term "alkyl" as a group or part of a group refers to any linear or branched chain alkyl group having a number of carbon atoms in the specified range. Thus, for example, "$C_{1-6}$alkyl" refers to all of the hexyl alkyl and pentyl alkyl isomers as well as n-, iso-, sec- and t-butyl, n- and iso-propyl, ethyl and methyl. As another example, "$C_{1-4}$alkyl" refers to n-, iso-, sec- and t-butyl, n- and iso-propyl, ethyl and methyl.

The term "alkoxy" represents any linear or branched chain alkyl group having a number of carbon atoms in the specified range and attached through an oxygen bridge. Examples of suitable alkoxy groups include methoxy, ethoxy, n-propoxy, i-propoxy, n-butoxy, s-butoxy, i-butoxy and t-butoxy.

The term "alkenyl" as a group or part of a group refers to any linear or branched chain alkyl group containing at least one double bond, which may occur at any point along the chain, and having a number of carbon atoms in the specified range. E- and Z-forms are both included, where applicable. Examples of suitable alkenyl groups include vinyl, allyl, butenyl and pentenyl.

The term "alkynyl" as a group or part of a group refers to any linear or branched chain alkyl group containing at least one triple bond, which may occur at any point along the chain, and having a number of carbon atoms in the specified range. Examples of suitable alkenyl groups include ethynyl, propynyl, butynyl and pentynyl.

The term "cycloalkyl" refers to any cyclic alkyl ring having a number of carbon atoms in the specified range. Examples of suitable cycloalkyl groups include cyclopropyl, cyclobutyl, cyclopentyl and cyclohexyl.

The terms "alkylene", "alkenylene" and alkynylene" as a group or part of a group refer to the groups "alkyl", "alkenyl" and "alkynyl" respectively, when they are divalent, i.e. attached at two atoms.

The term "halogen" or "halo" means fluorine, chlorine, bromine and iodine (alternatively referred to as fluoro, chloro, bromo and iodo, respectively).

The term "aryl" as a group or part of a group means a carbocyclic aromatic ring. Examples of suitable aryl groups include phenyl and naphthyl.

The term "Het" as a group or part of a group means a 5- to 7-membered saturated or unsaturated non-aromatic ring having 1 to 4 heteroatoms selected from N, O and S.

The term "heteroaryl" as a group or part of a group means a 5- to 10-membered heteroaromatic ring system containing 1 to 4 heteroatoms selected from N, O and S. Examples of such groups include pyrrolyl, furanyl, thienyl, pyridyl, pyrazolyl, imidazolyl, oxazolyl, isoxazolyl, thiazolyl, isothiazolyl, pyrazinyl, pyrimidinyl, pyridazinyl, triazolyl, oxadiazolyl, thiadiazolyl, triazinyl, tetrazolyl, indolyl, benzothienyl, benzimidazolyl, benzofuryl, quinolyl and isoquinolyl.

Unless expressly stated to the contrary, all ranges cited herein are inclusive. For example, a heteroaryl ring described as containing from "1 to 3 heteroatoms" means the ring can contain 1, 2, or 3 heteroatoms.

Where a compound or group is described as "optionally substituted" one or more substituents may be present. Furthermore, optional substituents may be attached to the compounds or groups which they substitute in a variety of ways, either directly or through a connecting group of which the following are examples: amine, amide, ester, ether, thioether, sulfonamide, sulfamide, sulfoxide, urea, thiourea and urethane. As appropriate an optional substituent may itself be substituted by another substituent, the latter being connected directly to the former or through a connecting group such as those exemplified above.

Specific compounds within the scope of this invention include those named in the Examples and Tables hereinbelow and their pharmaceutically acceptable salts.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, fumaric acid, p-toluenesulfonic acid, maleic acid, succinic acid, acetic acid, citric acid, tartaric acid, carbonic acid, phosphoric acid or sulfuric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulfate ester, or reduction or oxidation of a susceptible functionality.

The present invention includes within its scope solvates of the compounds of formula (I) and salts thereof, for example, hydrates.

The present invention also includes within its scope any enantiomers, diastereomers, geometric isomers and tautomers of the compounds of formula (I). It is to be understood that all such isomers and mixtures thereof are encompassed within the scope of the invention.

The preferred compounds of the present invention will have the stereochemistry as shown in formula (Ic):

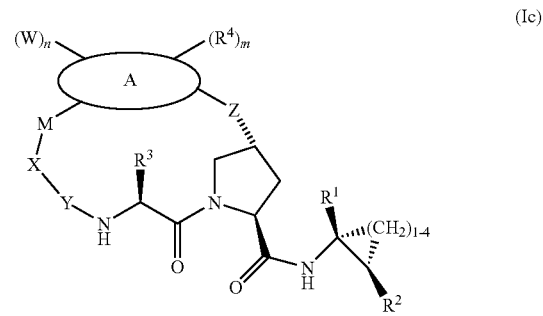

(Ic)

The present invention further provides a compound of formula (I) or a pharmaceutically acceptable salt thereof for use in therapy.

The present invention also provides a compound of formula (I) or a pharmaceutically acceptable salt thereof for use in the treatment or prevention of infection by hepatitis C virus in a human or animal.

In another aspect, the invention provides the use of a compound of formula (I) as defined above, or a pharmaceutically acceptable salt thereof, for the manufacture of a medicament for treatment or prevention of infection by hepatitis C virus in a human or animal.

A further aspect of the invention provides a pharmaceutical composition comprising a compound of formula (I) as defined above, or a pharmaceutically acceptable salt thereof, in association with a pharmaceutically acceptable carrier. The composition may be in any suitable form, depending on the intended method of administration. It may for example be in the form of a tablet, capsule or liquid for oral administration, or of a solution or suspension for administration parenterally.

The pharmaceutical compositions optionally also include one or more other agents for the treatment of viral infections such as an antiviral agent, or an immunomodulatory agent such as α-, β- or γ-interferon.

In a further aspect, the invention provides a method of inhibiting hepatitis C virus protease and/or of treating or preventing an illness due to hepatitis C virus, the method involving administering to a human or animal (preferably mammalian) subject suffering from the condition a therapeutically or prophylactically effective amount of the pharmaceutical composition described above or of a compound of formula (I) as defined above, or a pharmaceutically acceptable salt thereof. "Effective amount" means an amount sufficient to cause a benefit to the subject or at least to cause a change in the subject's condition.

The term "subject" (alternatively referred to herein as "patient") as used herein refers to an animal, preferably a mammal, most preferably a human, who has been the object of treatment, observation or experiment.

The dosage rate at which the compound is administered will depend on a variety of factors including the activity of the specific compound employed, the metabolic stability and length of action of that compound, the age of the patient, body weight, general health, sex, diet, mode and time of administration, rate of excretion, drug combination, the severity of the particular condition and the host undergoing therapy. Suitable dosage levels may be of the order of 0.02 to 5 or 10 g per day, with oral dosages two to five times higher. For instance, administration of from 10 to 50 mg of the compound per kg of body weight from one to three times per day may be in order. Appropriate values are selectable by routine testing. The compound may be administered alone or in combination with other treatments, either simultaneously or sequentially. For instance, it may be administered in combination with effective amounts of antiviral agents, immunomodulators, anti-infectives or vaccines known to those of ordinary skill in the art. It may be administered by any suitable route, including orally, intravenously, cutaneously and subcutaneously. It may be administered directly to a suitable site or in a manner in which it targets a particular site, such as a certain type of cell. Suitable targeting methods are already known.

An additional aspect of the invention provides a method of preparation of a pharmaceutical composition, involving admixing at least one compound of formula (I) as defined above, or a pharmaceutically acceptable salt thereof, with one or more pharmaceutically acceptable adjuvants, diluents or carriers and/or with one or more other therapeutically or prophylactically active agents.

As noted above, the present invention also relates to a method of inhibiting HCV NS3 protease, inhibiting HCV replication, or preventing or treating HCV infection with a compound of the present invention in combination with one or more therapeutic agents and a pharmaceutical composition comprising a compound of the present invention and one or more therapeutic agents selected from the group consisting of a HCV antiviral agent, an immunomodulator, and an anti-infective agent. Such therapeutic agents active against HCV include ribavirin, levovirin, viramidine, thymosin alpha-1, interferon-β, interferon-α, pegylated interferon-α (peginterferon-α), a combination of interferon-α and ribavirin, a combination of peginterferon-α and ribavirin, a combination of interferon-α and levovirin, and a combination of peginterferon-α and levovirin. Interferon-α includes recombinant interferon-α2a (such as Roferon interferon available from Hoffmann-LaRoche, Nutley, N.J.), pegylated interferon-α2a (Pegasys™), interferon-α2b (such as Intron-A interferon available from Schering Corp., Kenilworth, N.J.), pegylated interferon-α2b (PegIntron™), a recombinant consensus interferon (such as interferon alphacon-1), and a purified interferon-α product. Amgen's recombinant consensus interferon has the brand name Infergen®. Levovirin is the L-enantiomer of ribavirin which has shown immunomodulatory activity similar to ribavirin. Viramidine represents an analog of ribavirin disclosed in WO 01/60379 (ICN Pharmaceuticals). In accordance with the method of the present invention, the individual components of the combination can be administered separately at different times during the course of therapy or concurrently in divided or single combination forms.

For the treatment of HCV infection, the compounds of the present invention may also be administered in combination with an agent that is an inhibitor of HCV NS3 serine protease. HCV NS3 protease inhibitors are disclosed in WO 98/22496, WO 98/46630, WO 99/07733, WO 99/07734, WO 99/38888, WO 99/50230, WO 99/64442, WO 00/09543, WO 00/59929, GB-2337262, WO 02/48116, WO 02/48172, and U.S. Pat. No. 6,323,180.

Ribavirin, levovirin, and viramidine may exert their anti-HCV effects by modulating intracellular pools of guanine nucleotides via inhibition of the intracellular enzyme inosine monophosphate dehydrogenase (IMPDH). Thus, inhibition of IMPDH represents another useful target for the discovery of inhibitors of HCV replication. Therefore, the compounds of the present invention may also be administered in combination with an inhibitor of IMPDH, such as VX-497, disclosed in WO 97/41211 and WO 01/00622 (Vertex); another IMPDH inhibitor, such as that disclosed in WO 00/25780 (Bristol-Myers Squibb); or mycophenolate mofetil [see A. C. Allison and E. M. Eugui, *Agents Action,* 44 (Suppl.): 165 (1993)].

For the treatment of HCV infection, the compounds of the present invention may also be administered in combination with the antiviral agent amantadine (1-aminoadamantane) [see J. Kirschbaum, *Anal. Profiles Drug Subs.* 12: 1-36 (1983)].

The compounds of the present invention may also be combined for the treatment of HCV infection with antiviral 2'-C-branched ribonucleosides disclosed in R. E. Harry-O'kuru, et al., *J. Org. Chem.,* 62: 1754-1759 (1997); M. S. Wolfe, et al., *Tetrahedron Lett.,* 36: 7611-7614 (1995); U.S. Pat. No. 3,480,613; WO 01/90121; WO 01/92282; WO 02/32920; WO 04/002999; WO 04/003000; and WO 04/002422. Such 2'-C-branched ribonucleosides include 2'-C-methyl-cytidine, 2'-C-methyl-uridine, 2'-C-methyl-adenosine, 2'-C-methyl-guanosine, and 9-(2-C-methyl-β-D-ribofuranosyl)-2,6-diaminopurine, and the corresponding amino acid ester of the ribose C-2', C-3', and C-5' hydroxyls and the corresponding optionally substituted cyclic 1,3-propanediol esters of the 5'-phosphate derivatives.

The compounds of the present invention may also be combined for the treatment of HCV infection with other nucleosides having anti-HCV properties, such as those disclosed in WO 02/51425 (Mitsubishi Pharma Corp.); WO 01/79246, WO 02/32920 and WO 02/48165 (Pharmasset, Ltd.); WO 01/68663 (ICN Pharmaceuticals); WO 99/43691; WO 02/18404 (Hoffmann-LaRoche); U.S. 2002/0019363; WO 02/100415; WO 03/026589; WO 03/026675; WO 03/093290; US 2003/0236216; US 2004/0006007; WO 04/011478; WO 04/013300; US 2004/0063658; and WO 04/028481.

For the treatment of HCV infection, the compounds of the present invention may also be administered in combination with an agent that is an inhibitor of HCV NS5B polymerase. Such HCV NS5B polymerase inhibitors that may be used as combination therapy include those disclosed in WO 02/057287, U.S. Pat. No. 6,777,395, WO 02/057425, US 2004/0067901, WO 03/068244, WO 2004/000858, WO 04/003138 and WO 2004/007512. Other such HCV polymerase inhibitors include valopicitabine (NM-283; Idenix) and 2'-F-2'-beta-methylcytidine (see also WO 2005/003147, assigned to Pharmasset, Ltd.).

The compounds of the present invention may also be combined for the treatment of HCV infection with non-nucleoside inhibitors of HCV polymerase such as those disclosed in WO 01/77091 (Tularik, Inc.); WO 01/47883 (Japan Tobacco, Inc.); WO 02/04425 (Boehringer Ingelheim); WO 02/06246, WO 03/062211, WO 2004/087714, WO 2004/110442, WO 2005/034941, WO 2005/023819, WO2006/029912, WO 2006/008556, WO 2006/027628 GB2430621, WO2006/046030, WO2006/046039, WO2006/119975, WO2007/028789 and WO2007/029029 (all Istituto di Ricerche di Biologia Molecolare P. Angeletti S.p.A.); WO 02/20497; WO 2005/016927 (in particular JTK003), and WO 2005/080399 (Japan Tobacco, Inc.); WO 2006/020082 (Bristol-Myers Squibb Company); and HCV-796 (Viropharma Inc.).

The present invention also provides a process for the preparation of compounds of formula (I).

According to a general process (a), compounds of formula (I) may be prepared by the coupling of the acid of formula (II) with the amine of formula (III):

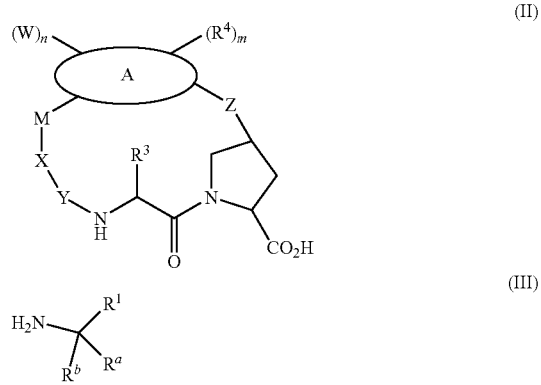

where m, n, $R^1$, $R^a$, $R^b$, $R^3$, $R^4$, M, W, X, Y, Z and ring A are as defined in relation to formula (I). The reaction is conveniently carried out in the presence of a coupling reagent, such as TBTU or HATU, and a base, such as diisopropylethylamine or triethylamine, in a solvent. Suitable solvents include DMF and dichloromethane.

The compound of formula (II) where M has 4 or more carbon atoms in the tether and one or more double bonds may be prepared by the internal ring closure of the diene of formula (IV):

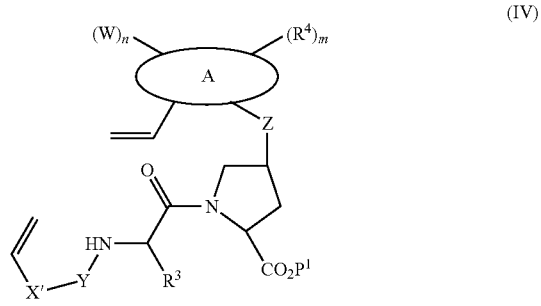

where m, n, $R^3$, $R^4$, W, Y, Z and ring A are as defined in relation to formula (I), $P^1$ is $C_{1-6}$alkyl, such as methyl, and X' is a suitable precursor to or the same as X. The reaction is conveniently carried out in the presence of a metathesis catalyst, such as Zhan catalyst [dichloro(5-chloro-2-isopropoxybenzylidene)(1,3-dimethylimidazolidin-2-ylidene)ruthenium], preferably at raised temperature, in a suitable solvent such as 1,2-dichloroethane. The resultant ring double bond may be hydrogenated to give a further compound of formula (II). The hydrogenation is preferably carried out in the presence of a suitable catalyst, such as palladium on carbon, in a suitable solvent, such as methanol/ethyl acetate mixture.

Compounds of formulae (II), (III) and (IV) are either well known in the art or may be prepared by conventional methodology well known to one of ordinary skill in the art using, for instance, procedures described in the accompanying Schemes and Examples, or by alternative procedures which will be readily apparent.

Further details of suitable procedures will be found in the accompanying Schemes and Examples. For instance compounds of formula (I) can be converted into other compounds of formula (I) using synthetic methodology well known in the art.

Thus, for instance, the compound of formula (I) where M is unsaturated may be converted into the compound of formula (I) where M is saturated by hydrogenation, preferably in the presence of a suitable catalyst, such as palladium on carbon, in a suitable solvent, such as methanol/ethyl acetate mixture.

The compounds of the present inventions are useful in the inhibition of HCV protease (e.g., HCV NS3 protease) and the prevention or treatment of infection by HCV. For example, the compounds of this invention are useful in treating infection by HCV after suspected past exposure to HCV by such means as blood transfusion, exchange of body fluids, bites, accidental needle stick, or exposure to patient blood during surgery.

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HCV protease, e.g., by competitive inhibition. Thus the compounds of this invention are commercial products to be sold for these purposes.

General Description of Synthesis:

The compounds of the present invention may be synthesised as outlined in the following general schemes.

Compounds above are generally accessible by formation of the central macrocyclic ring, followed by elaboration as shown in the following general scheme (P=protecting group, Q=leaving group):

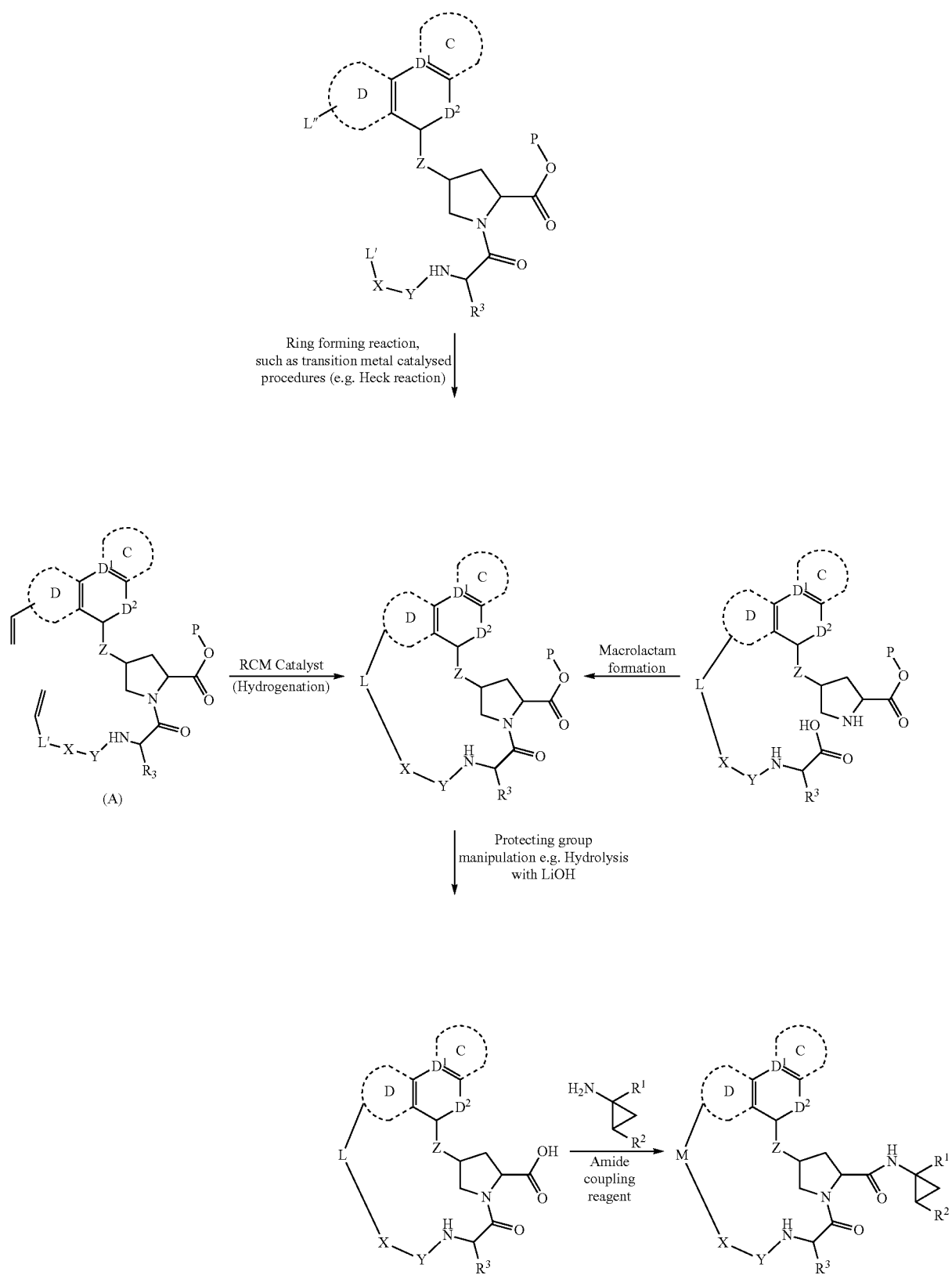

The same general approach was used for the preparation of compounds in which ring C is attached to ring D rather than ring B.
General procedures for preparing intermediates for the Formula (A) are shown in Schemes 2-3a:
Scheme 2
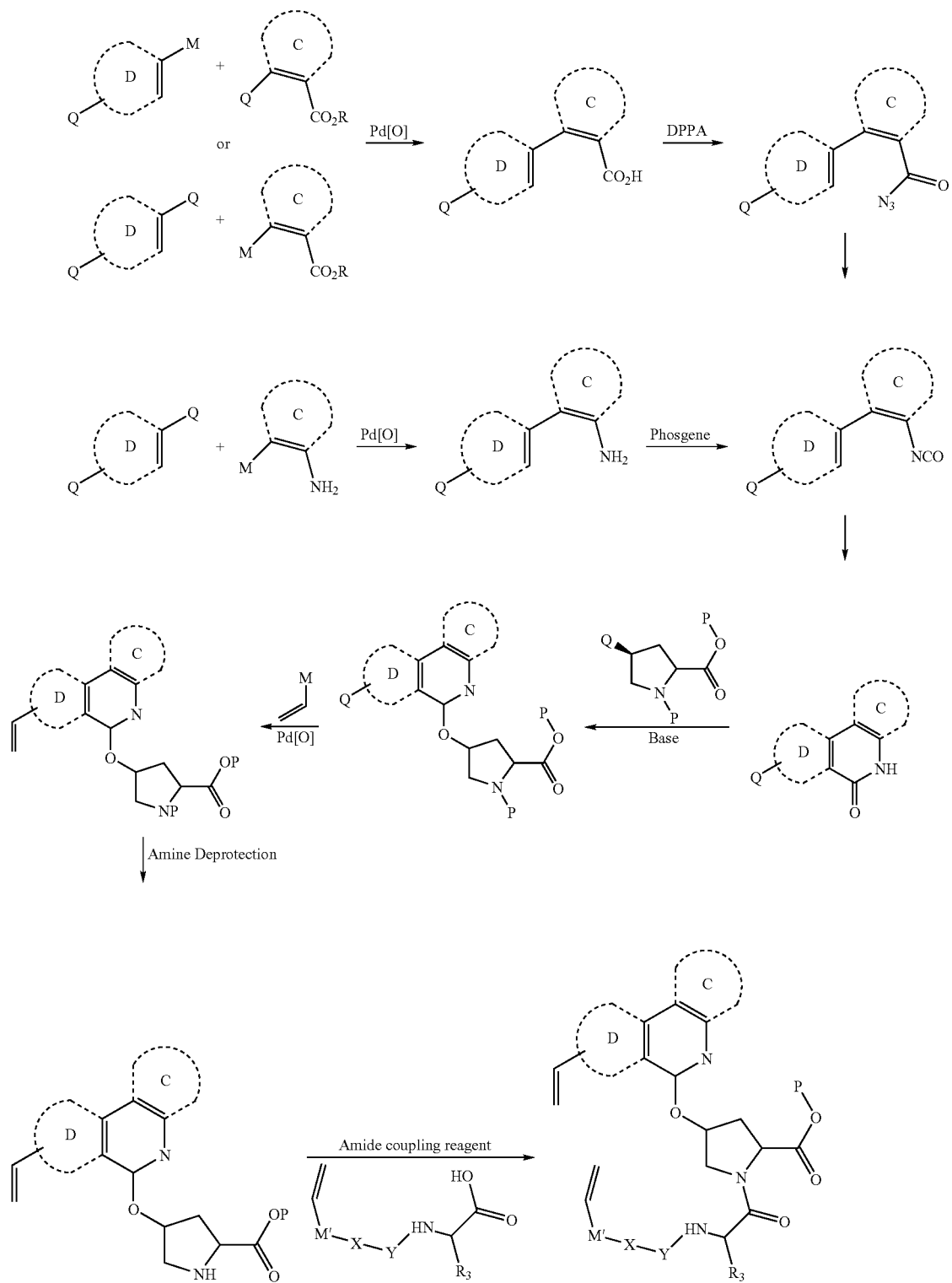

Scheme 3
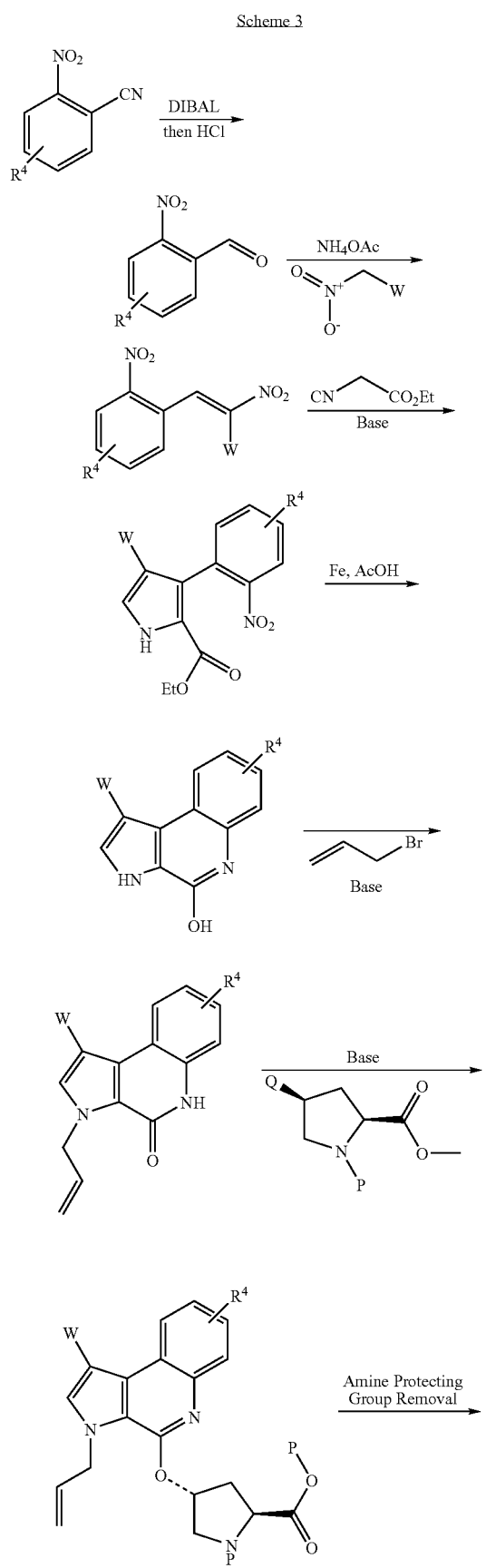
-continued
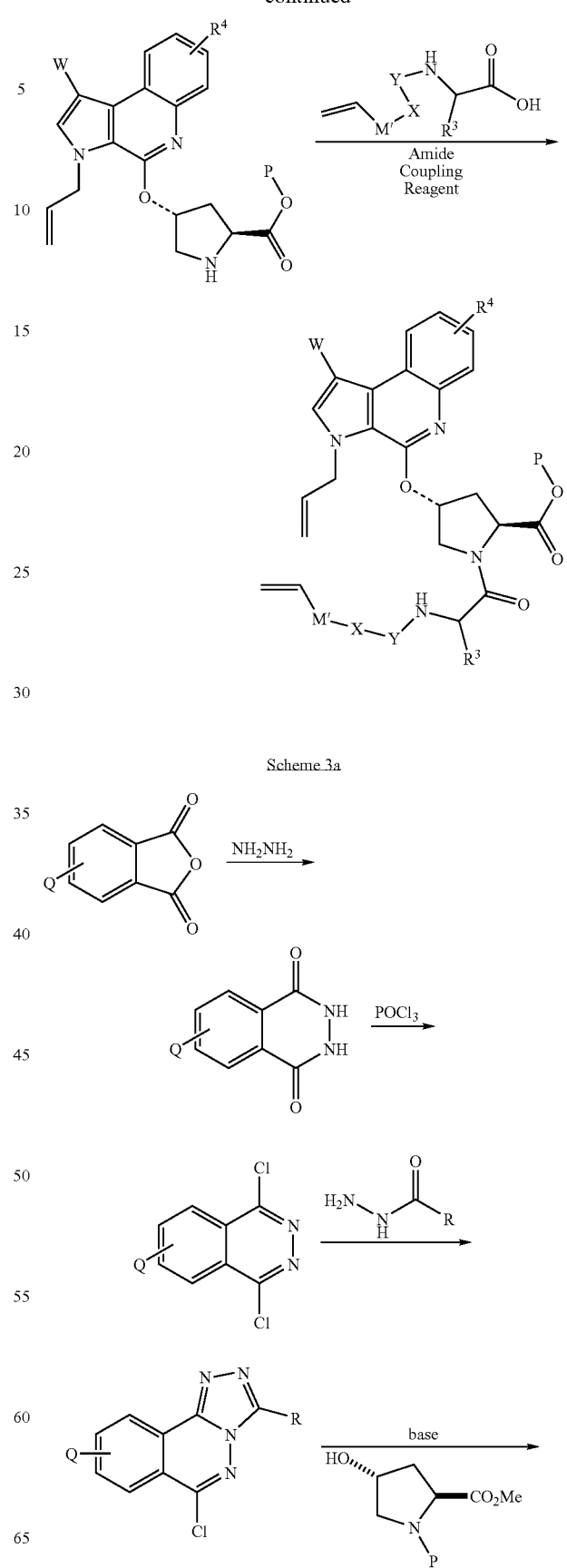
Scheme 3a

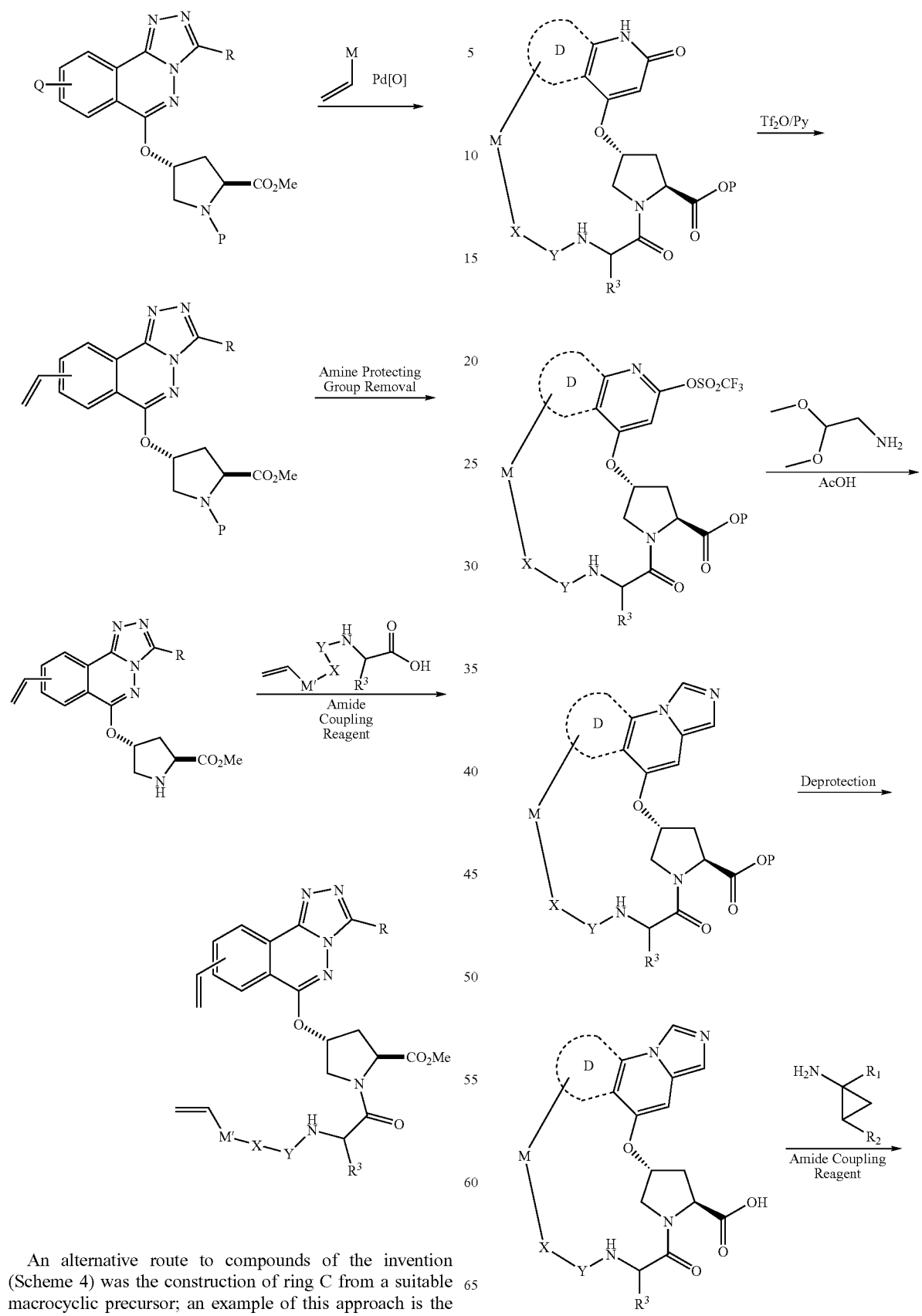
An alternative route to compounds of the invention (Scheme 4) was the construction of ring C from a suitable macrocyclic precursor; an example of this approach is the synthesis of the compounds exemplified below.

-continued

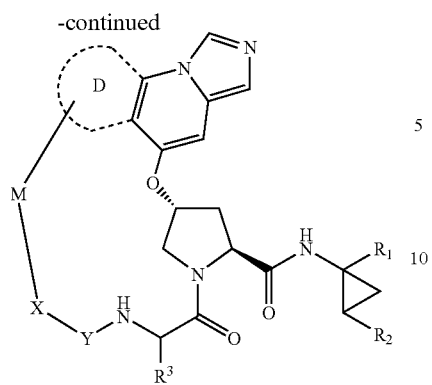

During any of the above synthetic sequences, it may be necessary and/or desirable to protect sensitive or reactive groups on any of the molecules concerned. This may be achieved by means of conventional protecting groups such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3$^{rd}$ ed., 1999. The protecting groups may be removed at a convenient subsequent stage using methods known from the art.

The HCV NS3 protease inhibitory activity of the present compounds may be tested using assays known in the art. One such assay is HCV NS3 protease time-resolved fluorescence (TRF) assay described as follows:

HCV NS3 Protease Time-Resolved Fluorescence (TRF) Assay

The NS3 protease TRF assay was performed in a final volume of 100 μl in assay buffer containing 50 mM HEPES, pH 7.5, 150 mM NaCl, 15% glycerol, 0.15% TRITON X-100, 10 mM DTT, and 0.1% PEG 8000: The NS3 protease was pre-incubated with various concentrations of inhibitors for 10-30 minutes. The peptide substrate for the assay is Ac-C (Eu)-DDMEE-Abu-[COO]-XSAK(QSY7)-NH$_2$ (SEQ. ID. NO. 1), where Eu is an europium-labeled group, Abu is 1-aminobutanoic acid which connects an ester linkage with 2-hydroxy propanoic acid (X). Hydrolysis of the peptide by NS3 protease activity causes in separation of the fluorophore from the quencher, resulting in an increase in fluorescence. Activity of the protease was initiated by adding the TRF peptide substrate (final concentration 50-100 nM). The reaction was quenched after 1 hour at room temperature with 100 μl of 500 mM MES, pH 5.5. Product fluorescence was detected using either a VICTOR V2 or FUSION fluorimeter (PERKIN ELMER LIFE AND ANALYTICAL SCIENCES) with excitation at 340 nm and emission at 615 nm with 50-400 μs delay. Testing concentrations of different enzyme forms was selected with a signal to background ratio of 10-30. The inhibition constants were derived using a four-parameter fit.

The compounds of the present invention were active in the TRF assay with activities of <10 μM.

Another suitable assay is the cellular Replicon or rheplisa assay described as follows:

Cell Based HCV Replication Assay

Cell clones that stably maintain subgenomic HCV replicon were obtained by transfecting Huh-7 cells with an RNA replicon identical to I$_{377}$neo/NS3-3'/wt described by Lohmann et al. (1999) (EMBL-genbank No. AJ242652), followed by selection with neomycin sulfate (G418). Viral replication was monitored by measuring the expression of the NS3 protein by an ELISA assay performed directly on cells grown in 96 wells microtiter plates (Cell-ELISA) using the anti-NS3 monoclonal antibody 10E5/24 (as described in International patent application publication no. WO 02/59321). Cells were seeded into 96 well plates at a density of 10$^4$ cells per well in a final volume of 0.1 ml of DMEM/10% FCS. Two hours after plating, 50 μl of DMEM/10% FCS containing a 3× concentration of inhibitor were added, cells were incubated for 96 hours and then fixed for 10 minutes with ice-cold isopropanol. Each condition was tested in duplicate and average absorbance values were used for calculations. The cells were washed twice with PBS, blocked with 5% non-fat dry milk in PBS+0.1% TRITON X100+0.02% SDS (PBSTS) and then incubated o/n at 4° C. with the 10E5/24 mab diluted in Milk/PBSTS. After washing 5 times with PBSTS, the cells were incubated for 3 hours at room temperature with Fc specific anti-mouse IgG conjugated to alkaline phosphatase (SIGMA), diluted in Milk/PBSTS. After washing again as above, the reaction was developed with p-nitrophenyl phosphate disodium substrate (SIGMA) and the absorbance at 405/620 nm read at intervals. For calculations, we used data sets where samples incubated without inhibitors had absorbance values comprised between 1 and 1.5. The inhibitor concentration that reduced by 50% the expression of NS3 (IC$_{50}$) was calculated by fitting the data to the Hill equation, $$\text{Fraction inhibition} = 1 - (A_i - b)/(A_0 - b) = [I]^n/([I]^n + IC50)$$

where:
- A$_i$=absorbance value of HBI10 cells supplemented with the indicated inhibitor concentration.
- A$_0$=absorbance value of HBI10 cells incubated without inhibitor.
- b=absorbance value of Huh-7 cells plated at the same density in the same microtiter plates and incubated without inhibitor.
- n=Hill coefficient.

The compounds of the present invention were active in the cell based HCV replication assay with activities <50 μM, and especially <5 μM.

Other examples of such assays are described in e.g., International patent application publication no. WO2005/046712. Compounds useful as HCV NS3 protease inhibitors would have a Ki less than 50 μM, more preferably less than 10 μM, most preferably less than 1 μM, especially less than 100 nM, and more especially less than 50 nM.

The following examples serve to illustrate the invention and its practice.

$^1$H NMR spectra were recorded on BRUKER AM series spectrometers operating at (reported) frequencies between 300 and 600 MHz. Chemical shifts (δ) for signals corresponding to non-exchangeable protons (and exchangeable protons where visible) are recorded in parts per million (ppm) relative to tetramethylsilane and are measured using the residual solvent peak as reference. Signals are tabulated in the order: multiplicity (s, singlet; d, doublet; t, triplet; q, quartet; m, multiplet; b, broad, and combinations thereof); coupling constant(s) in Hertz (Hz); number of protons. Mass spectral (MS) data were obtained on a PERKIN ELMER API 100, or WATERS MICROMASS ZQ, operating in negative (ES$^-$) or positive (ES$^+$) ionization mode and results are reported as the ratio of mass over charge (m/z). Preparative scale HPLC separations were carried out on a WATERS MICROMASS System incorporating a 2525 pump module, a MICROMASS ZMD detector and a 2767 collection module, under FRACTION LINX software or on a SHIMADZU preparative system.

Zhan Ruthenium Metathesis Catalyst RC-303 (Zhan Catalyst 1B, RC-303, Zannan Pharma Ltd.)

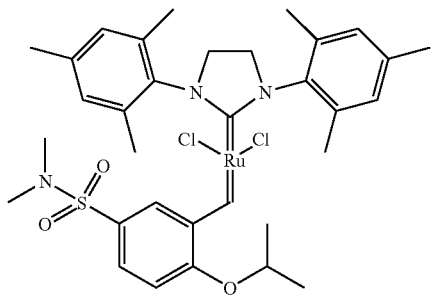

LIST OF ABBREVIATIONS

BOP Benzotriazole-1-yl-oxy-tris-(dimethylamino)-phosphonium hexafluorophosphate
Brosyl chloride 4-Bromophenyl sulfonylchloride
$CH_3CN$ Acetonitrile
DABCO 1,4-Diazabicyclo[2.2.2]octane
DBU 1,8-Diazabicyclo[5.4.0]undec-7-ene
DCC Dicyclohexylcarbodiimide
DCE Dichloroethane
DCM Dichloromethane
DMAP 4-Dimethylamino pyridine
DIPEA Diisoproylethylamine
DMF Dimethylformamide
DMSO Dimethyl Sulfoxide
EDC N-(3-Dimethylaminopropyl)-N'-ethylcarbodiimide
$Et_3N$ Triethylamine
$Et_2O$ Diethyl ether
EtOAc Ethyl Acetate
EtOH Ethanol
h hour(s)
HATU O-(7-Azabenzotriazol-1-yl)-N,N,N',N'-tetramethyluronium hexafluorophosphate
HBr Hydrobromic acid
HCl Hydrochloric acid
HOAc Acetic acid
HOAt 1-Hydroxy-7-azabenzotriazole
HOBT 1-hydroxybenzotriazole
LiOH Lithium hydroxide
MeOH Methanol
min minute(s)
$MgSO_4$ Magnesium sulfate
$Na_2SO_4$ Sodium sulfate
$NaHCO_3$ Sodium bicarbonate
NaOH Sodium hydroxide
$NH_4Cl$ Ammonium chloride
$NH_4OH$ Ammonium hydroxide
NMP N-methyl-pyrrolidinone
Nle Norleucine Pd/C Palladium on carbon
PhMe Toluene
$PPh_3$ Triphenylphosphine
RT Room temperature
TBAF Tetrabutylammonium fluoride
TBTU O-Benzotriazol-1-yl-N,N,N',N'-tetramethyluronium tetrafluoroborate
TEA Triethylamine
THF Tetrahydrofuran

SYNTHESIS OF INTERMEDIATES

Preparation of Intermediates A

| Intermediate | Name | Lit. Reference |
|---|---|---|
| A1 | (1R,2S)-1-Amino-N-(cyclopropylsulfonyl)-2-vinylcyclopropanecarboxamide hydrochloride | Wang et al, U.S. Pat. No. 6,995,174 |
| A2 | Ethyl (1R,2S)-1-amino-2-vinylcyclopropanecarboxylate hydrochloride | Llinas-Brunet et al, U.S. Pat. No. 6,323,180 |

Intermediate A3: (1R,2R)-1-Amino-N-(cyclopropylsulfonyl)-2-ethylcyclopropanecarboxamide hydrochloride Step 1: tert-Butyl ((1R,2R)-1-{[(cyclopropylsulfonyl)amino]carbonyl}-2-ethylcyclopropyl)carbamate A hydrogenaton vessel was charged with a methanol (1000 mL) slurry of tert-butyl ((1R,2S)-1-{[(cyclopropylsulfonyl)amino]carbonyl}-2-vinylcyclopropyl)carbamate (164 g, 0.50 mol) and 5% Ru/C (dry, 7.5 wt %, 12.4 g) and stirred. The vessel was placed under nitrogen (20 psig) and vented to atmospheric pressure three times to remove residual oxygen. The vessel was then placed under hydrogen (50 psig). After 20 h, the vessel was vented to atmospheric pressure. The reaction slurry was then transferred out of the reaction and filtered through SOLKA FLOK (34 grams, wetted w/100 mL MeOH) to yield a clear, light brown solution. The SOLKA FLOK was rinsed with MeOH (200 mL×2). The combined methanol solutions were concentrated under reduced pressure to yield crude product as a white solid (153 g). The crude product was slurried in EtOAc (800 mL), warmed to 40° C. and aged 30 min. The solution was then seeded, aged 30 min, and heptane (500 mL) was added via addition funnel over 30 min. The partially crystallized solid was cooled to RT and aged overnight after which additional heptane (500 mL) was added. After 1 h, additional heptane (250 mL) was added via addition funnel, and the white slurry aged for 1 h. The solution was filtered and the solid was rinsed with heptane/EtOAc (500 mL, 4:1) and dried under reduced pressure to give tert-butyl ((1R,2R)-1-{[(cyclopropylsulfonyl)amino]carbonyl}-2-ethylcyclopropyl)carbamate (125.9 g).

Step 2: (1R,2R)-1-Amino-N-(cyclopropylsulfonyl)-2-ethylcyclopropanecarboxamide hydrochloride (Intermediate A3)

A solution of the product from Step 1 above (92 g, 0.28 mol) in DCM (1200 mL) was cooled to 0° C. and HCl bubbled through the solution for 10 min, the cooling bath removed and the reaction mixture stirred for 2 h. Nitrogen was bubbled through the reaction mixture for 5 min and the volatiles evaporated. The residue was azeotroped with DCM (×3) to give an off white powder (75 g). LRMS (M+H)+ Calcd.=233. found 233

Preparation of Intermediates B

Intermediate B1:
N-[(pent-4-en-1-yloxy)carbonyl]-L-norleucine

To a solution of 1-penten-4-ol (0.95 g, 11.0 mmol) in DMF (15 mL) at 0° C. was added carbonyldiimidazole (1.79 g, 11.0 mmol). The reaction mixture was warmed to RT and stirred for 30 min. L-norleucine methyl ester hydrochloride (2.0 g, 11.0 mmol) was then added, the reaction mixture was heated to 50° C. and stirred for 15 min. Upon cooling, the reaction mixture was diluted with Et$_2$O and washed twice with water. The organic layer was dried over sodium sulfate, filtered and concentrated. The crude product was purified by silica gel chromatography (gradient elution 10 to 90% EtOAc in hexanes) to afford 2.1 g (74%) methyl N-[(pent-4-en-1-yloxy)carbonyl]-L-norleucinate as a clear oil.

To a stirred solution of methyl N-[(pent-4-enyloxy)carbonyl]-L-norleucinate (8.50 g, 33.03 mmol) in THF (20 mL) was added 1N NaOH (20 mL). This reaction solution was stirred at RT for 3 h, then acidified to pH 3 with 1N HCl and extracted with (3×250 mL) EtOAc. The combined EtOAc layer was washed with 50 mL water, 50 mL brine, dried over sodium sulfate, filtered and concentrated to give 7.09 g (88%) of the title product as clear oil. LRMS (ESI) m/z 244 [(M+H)+; calcd for $C_{12}H_{22}NO_4$: 244].

Intermediate B2: (2S)-3,3-dimethyl-2-{[(pent-4-en-1-yloxy)carbonyl]amino}butanoic acid Diisopropylethyl amine (9.85 g, 76.2 mmol) was added dropwise to a 0° C. solution of 4-penten-1-ol (7.22 g, 83.9 mmol) and triphosgene (11.3 g, 38.1 mmol) in 160 mL dioxane. The resulting white suspension was stirred for 5 min at 0° C., then allowed to warm to 25° C. over 1 h. The suspension was cooled to 0° C. with an ice bath and 1 N NaOH (76.2 mL) and L-tert-butylglycine (10.0 g, 76.2 mmol) were added. The reaction mixture was warmed to 25° C. and stirred for 18 h. The dioxane was removed in vacuo and the reaction mixture was basified to pH 12 with 1 N NaOH. The aqueous layer was extracted with DCM (3×150 mL), then acidified to pH~1 with 6 N HCl. The aqueous layer was extracted with DCM (3×150 mL). The combined organic layers were dried over MgSO$_4$ and concentrated to give the compound as a tan oil (13.7 g, 73.9% yield). LRMS (ESI) m/z 244 [(M+H)+; calcd for $C_{12}H_{22}NO_4$ 244].

The following carbamate intermediates (B3-B24) were prepared using the chemistry described for the preparation of (2S)-3,3-dimethyl-2-{[(pent-4-en-1-yloxy)carbonyl] amino}butanoic acid (B2), by utilizing the appropriate amino acid and alcohol. Compounds in Table 1 having a basic group or acidic group are depicted and named as the free base or acid. Depending on the reaction and purification conditions, various compounds in Table 1 having a basic group were isolated in either the free base form, or as a salt (such as HCl salt), or in both free base and salt forms. Various compounds in the table having an acid group were isolated in either the acid form, or as a salt (such as Na salt), or in both acid and salt forms.

| Int | Amino Acid | Alcohol | Name | LRMS (M + H)+ |
|---|---|---|---|---|
| B3 | L-Norleucine | 3-Buten-1-ol | N-[(but-3-en-1-yloxy)carbonyl]-L-norleucine | 230.3 |
| B4 | L-Norleucine | 5-Hexen-1-ol | N-[(hex-5-en-1-yloxy)carbonyl]-L-norleucine | 258.3 |
| B5 | L-Norleucine | 6-Hepten-1-ol | N-[(hept-6-en-1-yloxy)carbonyl]-L-norleucine | 272.3 |
| B6 | L-Norleucine | 7-Octen-1-ol | N-[(oct-7-en-1-yloxy)carbonyl]-L-norleucine | 286.4 |
| B7 | L-Valine | 4-Penten-1-ol | N-[(Pent-4-en-1-yloxy)carbonyl]-L-valine | 230.3 |
| B8 | L-Valine | 4-Propen-1-ol | N-[(allyloxy)carbonyl]-L-valine | 202.2 |
| B9 | L-Valine | 4-Buten-1-ol | N-[(but-3-en-1-yloxy)carbonyl]-L-valine | 216.3 |
| B10 | L-tert-leucine | 5-Hexen-1-ol | N-[(Hex-5-en-1-yloxy)carbonyl]-3-methyl-L-valine | 258.3 |
| B11 | L-tert-leucine | 6-Hepten-1-ol | N-[(Hept-6-en-1-yloxy)carbonyl]-3-methyl-L-valine | 272.3 |
| B12 | L-tert-leucine | 3-Buten-1-ol | N-[(But-3-en-1-yloxy)carbonyl]-3-methyl-L-valine | 230.3 |
| B13 | L-tert-leucine | 2,2-Dimethyl hex-5-en-1-ol Ref: J. Org. Chem. (1991), 56, 1623 | N-{[(2,2-Dimethylhex-5-en-1-yl)oxy]carbonyl}-3-methyl-L-valine | 286.3 |
| B14 | L-tert-leucine | Allyl alcohol | N-[(allyloxy)carbonyl]-3-methyl-L-valine | 215.2 |
| B15 | L-tert-leucine | 7-Octen-1-ol | 3-Methyl-N-[(oct-7-en-1-yloxy)carbonyl]-L-valine | 286.3 |
| B16 | L-Cyclohexyl-glycine | 6-Hepten-1-ol | (2S)-Cyclohexyl {[(hept-6-en-1-yloxy)carbonyl]amino}acetic acid | 298.3 |
| B17 | L-Cyclohexyl-glycine | 5-Hexen-1-ol | (2S)-Cyclohexyl {[(hex-5-en-1-yloxy)carbonyl]amino}acetic acid | 284.4 |
| B18 | L-tert-leucine | 6-Heptyn-1-ol | N-[(hept-6-yn-1-yloxy)carbonyl]-3-methyl-L-valine | 270.2 |
| B19 | L-Cyclohexyl- | 2,2-dimethylhept-6-en-1-ol. | (2S)-cyclohexyl({[(2,2-dimethylhept-6-en-1- | 326.5 |

-continued

| Int | Amino Acid | Alcohol | Name | LRMS (M + H)+ |
|---|---|---|---|---|
| | glycine | Ref: WO2005/030796 | yl)oxy]carbonyl}amino)acetic acid | |
| B20 | L-Cyclohexyl-glycine | 2,2-Dimethylpent-4-en-1-ol Ref: Tetrahed-ron (1987), 43, 5637 | (2S)-cyclohexyl({[(2,2-dimethylpent-4-en-1-yl)oxy]carbonyl}amino)acetic acid | 298.3 |
| B21 | L-Cyclopentyl-glycine | 2,2-Dimethylpent-4-en-1-ol Ref: Tetrahed-ron (1987), 43, 5637 | (2S)-cyclopentyl({[(2,2-dimethylpent-4-en-1-yl)oxy]carbonyl}amino)acetic acid | 284.3 |
| B22 | L-Cyclohexyl-glycine | 2-allylcyclo pentanol Ref: JACS (1982), 104, 2444 | (2S)-({[(2-allylcyclopentyl)oxy]carbonyl}amino)(cyclohexyl)acetic acid | 310.3 |
| B23 | L-tert-leucine | 2,2-Dimethylpent-4-en-1-ol Ref: Tetrahed-ron (1987), 43, 5637. | N-{[(2,2-dimethylpent-4-en-1-yl)oxy]carbonyl}-3-methyl-L-valine | 272.3 |
| B24 | L-Norleucine | 2,2-Dimethylpent-4-en-1-ol Ref: Tetrahed-ron. (1987), 43, 5637. | N-{[(2,2-dimethylpent-4-en-1-yl)oxy]carbonyl}-L-norleucine | 272 |
| B25 | L-Cyclopentyl glycine | 2,2-dimethylhept-6-en-1-ol Ref: J. Org. Chem. (1980), 43, 2685. | (2S)-cyclopentyl({[(2,2-dimethylhept-6-en-1-yl)oxy]carbonyl}amino)acetic acid | 312 |

Intermediate B26: 3-methyl-N-{[methyl(pent-4-en-1-yl)amino]carbonyl}-L-valine

Step 1: Methyl 3-methyl-N-{[methyl(pent-4-en-1-yl)amino]carbonyl}-L-valinate To a solution of N-methylpent-4-en-1-amine (ref: Org. Biomol. Chem.; EN; 2; 20; 2004; 3006-3017) (2.0 g, 21.2 mmol) in THF (20 mL) was added methyl 3-methyl-N-(oxomethylene)-L-valinate (Ref: EP 0 486 948 A2) (3.5 g, 20.2 mmol). After 2 h, the solvent was removed in vacuo and the crude material was purified on silica (40% EtOAc/hexanes) to yield the title compound. LRMS (M+H)+ 271.3

Step 2: N-{[(1,1-Dimethylpent-4-en-1-yl)amino]carbonyl}-L-valine

To a solution of the product from Step 1, methyl 3-methyl-N-{[methyl(pent-4-en-1-yl)amino]carbonyl}-L-valinate, (3.0 g, 11.2 mmol) in THF (40 mL) was added 1M lithium hydroxide (56.0 mL, 1 M solution 56.0 mmol). The reaction mixture was stirred at 50° C. under nitrogen for 1 h, cooled to r.t. and THF removed in vacuo. Aqueous KHSO$_4$ was then added and the mixture extracted with DCM (3×). The combined organic extracts were dried over anhydrous Na$_2$SO$_4$ and the solvent was removed in vacuo to give the title compound as a colorless oil (2.95 g). LRMS (M+H)+=257.3.

| Int | Amino Acid | Amine | Name | LRMS (M + H)+ |
|---|---|---|---|---|
| B26 | L-tert-leucine | N-methylpent-4-en-1-amine Ref: Org. Biomol. Chem. 2; 20; 2004; 3006-3017 | 3-methyl-N-{[methyl(pent-4-en-1-yl)amino]carbonyl}-L-valine | 257.3 |
| B27 | L-Cyclohexyl-glycine | N,2,2-trimethylpent-4-en-1-amine | (2S)-cyclohexyl({[(2,2-dimethylpent-4-en-1)(methyl)amino]carbonyl}amino)acetic acid | 311.4 |
| B28 | L-Cyclopentyl-glycine | N-methylhept-6-en-1-amine | (2S)-cyclopentyl({[hept-6-en-1-yl(methyl)amino]carbonyl}amino)acetic acid | 297.1 |

Preparation of Intermediates C

Intermediate C1: 8-bromo-9-methoxy-6-oxo-5,6-dihydrophenanthridine-3-carbonitrile Step 1: 1-bromo-4-iodo-2-methoxybenzene To a suspension of 4-bromo-3-methoxyaniline (25 g, 124 mmol) in concentrated HCl (1.7 L) cooled to 0° C. was added sodium nitrite (11.1 g, 161 mmol) in water (250 mL) slowly over 30 min keeping the temperature below 8° C. After stirring for 2 h, to the resulting orange solution was added KI (61.6 g, 371 mmol) in water (250 mL) slowly over 30 min keeping the temperature below 8° C. The mixture was then warmed to r.t. and stirred for a further 1.5 h. It was then filtered through a sintered glass wool funnel. The resulting solid was dissolved in EtOAc (1.2 L) and washed with water, 0.5 N NaOH, aq. sodium bisulfite, and brine. The organic layer was then dried over $Na_2SO_4$, filtered through a pad of silica, and then solvent was removed in vacuo. The crude material was purified on silica (100% hexanes) to yield the title product.

Step 2: 2-amino-4'-bromo-3'-methoxybiphenyl-4-carbonitrile

To a mixture of the product from Step 1, -bromo-4-iodo-2-methoxybenzene (750 mg, 2.4 mmol), CsF (1.09 g, 7.2 mmol), (2-amino-4-cyanophenyl)boronic acid hydrochloride (390 mg, 2.4 mmol), and $Pd(PPh_3)_4$ (277 mg, 0.24 mmol) was added DME (15 mL) under N2. It was then heated to 100° C. After 36 h, to the thick red suspension was added EtOAc and water. The organic layer was washed with brine, dried over $Na_2SO_4$, and the solvent was removed in vacuo. The residue was purified on silica (gradient elution, 3-50% EtOAc/hex) to yield the title compound as a red oil. LRMS $(M+H)^+=303.1$.

Step 3: 8-bromo-9-methoxy-6-oxo-5,6-dihydrophenanthridine-3-carbonitrile

To the product from Step 2,2-amino-4'-bromo-3'-methoxybiphenyl-4-carbonitrile (363 mg, 1.2 mmol) was added phosgene (20% solution in PhMe, 5.9 g, 11.97 mmol) and the mixture was heated to reflux for 2 h. The solvent was then removed in vacuo to give crude 4'-bromo-2-isocyanato-3'-methoxybiphenyl-4-carbonitrile (394 mg, 1.2 mmol) which was then taken up in chlorobenzene (4 mL). To this mixture was then added $AlCl_3$ (319 mg, 2.4 mmol) at r.t. 1 N HCl (30 mL) was then added which caused a grey precipitate to form. This was isolated by filtration and washed with DCM and MeOH to give the title compound. LRMS $(M+H)^+=329.0$.

Intermediate C2: 8-bromo-3,9-dimethoxyphenanthridin-6(5H)-one

Step 1: 4'-bromo-3',4-dimethoxy-2-nitrobiphenyl

To a solution of 1-iodo-4-methoxy-2-nitrobenzene (5 g, 17.9 mmol) in THF (50 mL) cooled to −60° C. was added phenylmagnesium bromide (10.4 mL, 25 wt %, 19.7 mmol) which gave a dark red solution. Trimethylborate (2.4 mL, 21.5 mmol) was then added dropwise. After 30 min, the reaction was quenched with 1 N HCl (40 mL) and extracted with ether. The organic layer was then dried over $Na_2SO_4$ and the solvent was removed in vacuo to give a dark brown oil which was tritrated with DCM to yield (4-methoxy-2-nitrophenyl)boronic acid as grey solid. A portion of this material (1.57 g, 8 mmol) was then taken up in DME (1 mL) and 1-bromo-4-iodo-2-methoxybenzene (C1, step 1) (2.5 g, 8 mmol), CsF (2.73 g, 18 mmol), and tetrakistriphenylphosphine palladium (0.92 g, 0.8 mmol) under nitrogen. The mixture was then heated to 100° C. for 18 h. The mixture was then extracted with water and EtOAc. The organic layer was then dried over $Na_2SO_4$ and the solvent was removed in vacuo. The crude material was then purified on silica (gradient elution, 3-50% EtOAc/hexanes) to yield the title compound as a yellow solid.

Step 2: 4'-bromo-3',4-dimethoxybiphenyl-2-amine

To a solution of the product from Step 1,4'-bromo-3',4-dimethoxy-2-nitrobiphenyl (1.5 g, 4.4 mmol) in THF (10 mL) was added HCl (12M, 9.24 mL, 111 mmol) and iron powder (4.48 g, 80.2 mmol). After 3 days at r.t., the solution was basified with saturated NaOH and extracted with EtOAc. The organic layer was then dried over $Na_2SO_4$ and the solvent was removed in vacuo. The crude material was then purified on silica (gradient elution, 5-45% EtOAc/hexanes) to yield the title compound as an orange foam. LRMS $(M+H)^+=308.2$.

Step 3: 8-bromo-3,9-dimethoxyphenanthridin-6(5H)-one

The title compound was prepared according to Step 3 of intermediate C1. LRMS $(M+H)^+=334.1$.

The following intermediates (C3-C6) were prepared using the chemistry described for the preparation of 8-bromo-9-methoxy-6-oxo-5,6-dihydrophenanthridine-3-carbonitrile (C1) or 8-bromo-3,9-dimethoxyphenanthridin-6(5H)-one (C2), by utilizing the appropriate aminoboronic acid or ester in step 2 (C1) or nitroboronic acid in step 1 (C2).

Compounds in Table 1 having a basic group or acidic group are depicted and named as the free base or acid. Depending on the reaction and purification conditions, various compounds in Table 1 having a basic group were isolated in either the free base form, or as a salt (such as HCl salt), or in both free base and salt forms. Various compounds in the table having an acid group were isolated in either the acid form, or as a salt (such as Na salt), or in both acid and salt forms.

| Int. | Procedure | Name | LRMS $(M + H)^+$ |
|---|---|---|---|
| C3 | C1 | 8-bromo-9-methoxyphenanthridin-6(5H)-one | 304.2 |
| C4 | C1 | 8-bromo-9-methoxy-3-methylphenanthridin-6(5H)-one | 318.2 |
| C5 | C2 | 8-bromo-3-fluoro-9-methoxyphenanthridin-6(5H)-one | 322.1 |
| C6 | C1 | 8-bromo-2-chloro-9-methoxyphenanthridin-6(5H)-one | 338.2 |

Intermediate C7: 6-bromo-2-ethoxybenzo[h]quinolin-4-ol

Step 1: ethyl 3-ethoxy-3-iminopropanoate hydrochloride

To a solution of ethyl cyanoacetate (5 g, 44.2 mol) in $Et_2O$ (4.5 mL) was added EtOH (2.84 mL, 48.6 mmol). HCl (g) was then bubbled into the solution for 10 min at 0° C. The mixture was then warmed to r.t. and stirred overnight. The solvent was then removed in vacuo to yield the title compound as a white powder. LRMS $(M+H)^+=160.3$.

Step 2: ethyl (3E)-3-[(1,4-bromo-1-naphthyl)imino]-3-ethoxypropanoate

To a solution of the product from Step 1, ethyl 3-ethoxy-3-iminopropanoate hydrochloride (5.27 g, 26.9 mmol) in EtOH (60 mL) was added 4-bromonaphthalen-1-amine (3.42 g, 15.4 mmol) under $N_2$ and the mixture was stirred at r.t. after sonicating for 5 min. After overnight, the resulting solid was removed by filtration and the solvent was removed in vacuo. The crude product was purified on silica (gradient elution, 0-30% EtOAc/hexanes) to yield the title compound as an oil. LRMS (M+H)$^+$=364.1.

Step 3: 6-bromo-2-ethoxybenzo[h]quinolin-4-ol

To refluxing DOWTHERM A (50 mL) was added the product from Step 2, ethyl (3E)-3-[(4-bromo-1-naphthyl)imino]-3-ethoxypropanoate (5.61 g, 15.4 mmol) in DOWTHERM A (5 mL). The mixture was then heated at this temperature for 5 min, and then cooled to r.t. The mixture was then diluted with hexanes and the resulting solid was removed by filtration. The solid was washed with additional hexanes to yield the title compound as a brown solid. LRMS (M+H)$^+$=318.1.

Intermediate C8: 8-bromo-6-chloro-9-methoxy-1,2,3,4-tetrahydrophenanthridine

Step 1: ethyl 2-{[(trifluoromethyl)sulfonyl]oxy}cyclohex-1-ene-1-carboxylate To a solution of ethyl cyclohexanone-2-carboxylate (5.02 g, 29.5 mmol) in DCM (100 mL) cooled to −78° C. was added DIPEA (25.4 mL, 146 mmol) and then triflic anhydride (5.98 mL, 35.4 mmol) dropwise. The mixture was then warmed to r.t. and stirred overnight. The reaction was then quenched with aqueous citric acid and extracted with additional water. The organic layer was dried over $Na_2SO_4$ and the solvent was removed in vacuo. The crude product was purified on silica (100% DCM) to give the title product as an oil.

Step 2: ethyl 2-(4-bromo-3-methoxyphenyl)cyclohex-1-ene-1-carboxylate

To a solution of the product from Step 1, ethyl 2-{[(trifluoromethyl)sulfonyl]oxy}cyclohex-1-ene-1-carboxylate (6.65 g, 22.0 mmol) in dioxane (125 mL) was added potassium carbonate (4.56 g, 33.0 mmol), PPh$_3$ (0.346 g, 1.32 mmol), bis(pinacolato)diboron (6.15 g, 24.20 mmol), and PdCl$_2$(PPh$_3$)$_2$ (0.463 g, 0.66 mmol). The mixture was then heated to 80° C. overnight. This solution was then cooled to r.t. and added to a mixture of 1-bromo-4-iodo-2-methoxybenzene (6.86 g, 21.92 mmol), PdCl$_2$(dppf) (0.481 g, 0.657 mmol), potassium carbonate (9.09 g, 65.7 mmol). This mixture was then heated to 80° C. overnight. The mixture was then cooled to r.t., diluted with EtOAc (300 mL) and washed with brine and aqueous KHSO$_4$. The organic layer was then dried over $Na_2SO_4$ and the solvent was removed in vacuo. The crude material was then purified on silica (100% DCM) to give impure product which was repurified on silica (gradient elution, 5-20% EtOAc/hexanes) to give the title compound.

Step 3: 8-bromo-9-methoxy-1,3,4,5-tetrahydrophenanthridin-6(2H)-one

To a solution of the product from Step 2, ethyl 2-(4-bromo-3-methoxyphenyl)cyclohex-1-ene-1-carboxylate (2.0 g, 5.9 mmol) in THF (120 mL), EtOH (50 mL), and water (12 mL) was added LiOH (0.565 g, 23.6 mmol) and the reaction was stirred at 70° C. for 24 h. After cooling to r.t., the EtOH and THF were removed in vacuo and the aqueous layer was washed with Et$_2$O. The pH was then adjusted to 1.4 with concentrated HCl and extracted with DCM two times. The organic layer was then dried over $Na_2SO_4$ and the solvent was removed in vacuo to yield 2-(4-bromo-3-methoxyphenyl)cyclohex-1-ene-1-carboxylic acid, which was dissolved in PhMe (9.6 mL) and treated with TEA (0.94 mL, 6.75 mmol) and diphenylphosphoryl azide (1.04 mL, 4.82 mmol). After 1 h at r.t., the mixture was filtered through a pad of silica washing with PhMe. Diphenylmethane (10 mL) was then added and the PhMe was removed in vacuo. The mixture was then heated to 250° C. for 2 h, cooled to r.t., the solids were removed by filtration, and washed with hexanes to give the title product as a tan solid. LRMS (M+H)$^+$=307.9.

Step 4: 8-bromo-6-chloro-9-methoxy-1,2,3,4-tetrahydrophenanthridine

To the product from Step 3, 8-bromo-9-methoxy-1,3,4,5-tetrahydrophenanthridin-6(2H)-one (880 mg, 2.86 mmol) was added POCl$_3$ (6 mL, 64.4 mmol) and the mixture was heated to 80° C. for 3 h. The excess POCl$_3$ was then removed in vacuo, the residue was dissolved in DCM and the pH was adjusted to 5 with 1N NaOH. The organic layer was then dried over $Na_2SO_4$ and the solvent was removed in vacuo. The resulting solid was tritrated with ether to yield the title compound as a light yellow solid. LRMS (M+H)$^+$=325.8.

Intermediate C9: 7-bromo-5-chloro-8-methoxy-2,3-dihydro-1H-cyclopenta[c]isoquinoline The title compound was prepared according to the procedure for intermediate C8 starting from methyl 2-oxocyclopentanecarboxylate in place of ethyl cyclohexanone-2-carboxylate in Step 1. LRMS (M+H)$^+$=311.8.

Intermediate C10: 3-allyl-1-methyl-3H-pyrrolo[2,3-c]quinolin-4-ol

Ref. Alazard et. al. Bioorg Med Chem Lett. 1991, 1, 725-728

Step 1: 1-Nitro-2-[2-nitroprop-1-en-1-yl]benzene

A solution of 2-nitrobenzaldehyde (5.0 g, 33.1 mmol) and ammonium acetate (2.55 g, 33.1 mmol) in AcOH (20 mL) was treated dropwise at 20° C. with nitroethane (2.84 mL, 39.7 mmol). The resulting solution was heated under reflux for 2 h, then cooled and diluted with EtOAc. The organic layer was washed with saturated aqueous NaHCO$_3$ solution and brine, then dried over $Na_2SO_4$. Filtration and removal of the volatiles gave a residue that was purified on silica gel (gradient elution, 0-40% EtOAc/hexanes) to give the title compound as an oil. (2.3 g, 33%). LCMS (ES+) m/z 209 (M+H)$^+$

Step 2: Ethyl 4-methyl-3-(2-nitrophenyl)-1H-pyrrole-2-carboxylate

A solution of 1-nitro-2-[2-nitroprop-1-en-1-yl]benzene (4.1 g, 19.7 mmol) in a mixture of THF (131 mL) and tert-BuOH (66 mL) was treated with DBU (4.45 mL, 29.5 mmol) and ethyl isocyanoacetate (2.67 g, 2.58 mL) added. The resulting solution was stirred for 1 h then heated to 70° C. for 4 h. The mixture was cooled and concentrated in vacuo to give a residue was taken up in EtOAc and aqueous HCl (1 N). The organic layer was separated and washed with brine then dried over $Na_2SO_4$. Filtration and solvent removal afforded a residue that was purified on silica gel (gradient elution, 0-40% EtOAc/hexanes) to afford the title compound (3.2 g, 59%) as solid. LCMS (ES+) m/z 275 (M+H)$^+$

Step 3: 1-methyl-3H-pyrrolo[2,3-c]quinolin-4-ol

A solution of ethyl 4-methyl-3-(2-nitrophenyl)-1H-pyrrole-2-carboxylate (3.2 g, 11.67 mmol) in AcOH (117 mL)

was treated at 20° C. with iron dust (6.52 g, 117 mmol). The reaction mixture was heated at 100° C. for 3 h. The white precipitate was removed by filtration and the filtrates were concentrated to give a residue that was purified on silica gel (gradient elution, 50-100% MeOH/Acetone) to afford the title compound (2.0 g, 86%) as a solid. LCMS (ES+) m/z 199 (M+H)$^+$.

Step 4:
3-allyl-1-methyl-3H-pyrrolo[2,3-c]quinolin-4-ol

A solution of 1-methyl-3H-pyrrolo[2,3-c]quinolin-4-ol (1.2 g, 6.05 mmol) in a mixture of THF (30 mL) and NMP (60 mL) was treated with $Cs_2CO_3$ (2.95 g, 9.08 mmol). Allyl bromide (0.524 mL, 6.06 mmol) was added dropwise, and the resulting mixture was stirred at 40° C. for 12 h. The mixture was cooled and quenched with aqueous HCl (1 N) and EtOAc. The organic layer was separated, washed with aqueous HCl (1 N), brine, and dried over $Na_2SO_4$. Filtration and removal of the volatiles gave a residue that was triturated with $Et_2O$ to give the title compound (0.78 g, 54%) as a solid. LCMS (ES+) m/z 239 (M+H)$^+$.

Intermediate C11: 3-allyl-7-methoxy-1-methyl-3H-pyrrolo[2,3-c]quinolin-4-ol

Prepared from 2-nitro-4-methoxybenzaldehyde according to the procedures described for intermediate C10. LCMS (ES+) m/z 269 (M+H)$^+$.

Intermediate C12:
7-bromo-8-methoxythieno[2,3-c]isoquinolin-5-ol

Step 1:
3-(4-bromo-3-methoxyphenyl)thiophene-2-carboxylic acid

A solution of 3-(dihydroxyboryl)thiophene-2-carboxylic acid (1.89 g, 10.85 mmol) and 1-bromo-4-iodo-2-methoxybenzene (3.09 g, 9.86 mmol) in a 3:1 mixture of MeCN:H2O (100 mL) was treated with $K_2CO_3$ (4.09 g, 29.6). Pd(OAc)$_2$ (66.4 mg, 0.30 mmol) and biphenyl-2-yl(dicyclohexyl)phosphine (207 mg, 0.59 mmol) were added and the mixture was stirred at 90° C. for 3 h. The mixture was cooled and concentrated, and the residue was added at 0° C. to a mixture of 10% aqueous NaOH (100 mL) and DCM. The mixture was acidified to pH=1 by addition of aqueous HCl (6 N) and the solid precipitate was collected by filtration, washed with cold $H_2O$ and DCM, then dried to afford the title compound (2.29 g, 74%). LCMS (ES$^+$) m/z 313, 315 (M+H)$^+$.

Step 2:
3-(4-bromo-3-methoxyphenyl)thiophene-2-carbonyl azide

A stirred solution of 3-(4-bromo-3-methoxyphenyl)thiophene-2-carboxylic acid (2.23 g, 7.13 mmol) in benzene (28.5 mL) was treated with triethylamine (1.39 ml, 9.98 mmol) and diphenylphosphoryl azide (1.96 g, 7.13 mmol). The mixture was stirred for 20 h, then the volatiles were removed ant the residue was purified by column chromatography on silica gel (eluent: toluene) to afford the title (1.63 g, 68%). LCMS (ES$^+$) m/z 310, 312 (M+H–N$_2$)$^+$.

Step 3:
7-bromo-8-methoxythieno[2,3-c]isoquinolin-5-ol

A solution of 3-(4-bromo-3-methoxyphenyl)thiophene-2-carbonyl azide (530 mg, 1.57 mmol) was dissolved in diphenylmethane (10 mL) was stirred, and the temperature was raised gradually to 270° C. Stirring was continued for 3 h then the mixture was cooled to 20° C. The precipitate was collected by filtration then washed with diphenylmethane and hexane to afford the title compound (431 mg, 89%). LCMS (ES$^+$) m/z 310, 312 (M+H)$^+$.

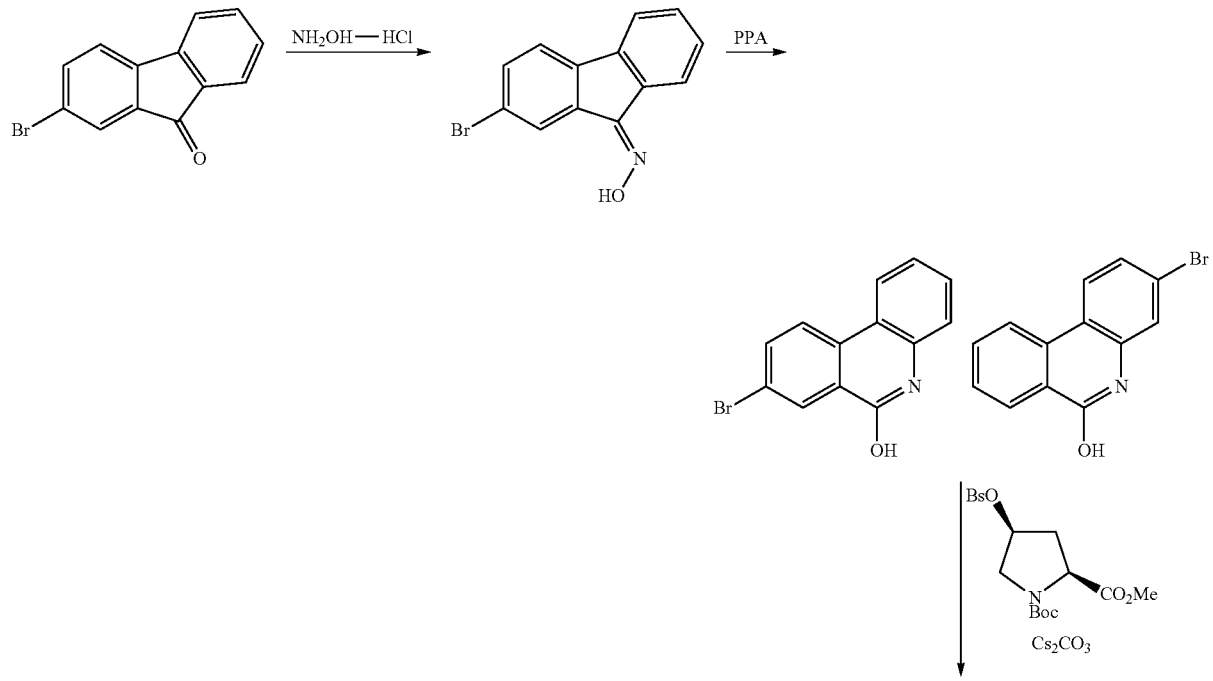

Scheme 1

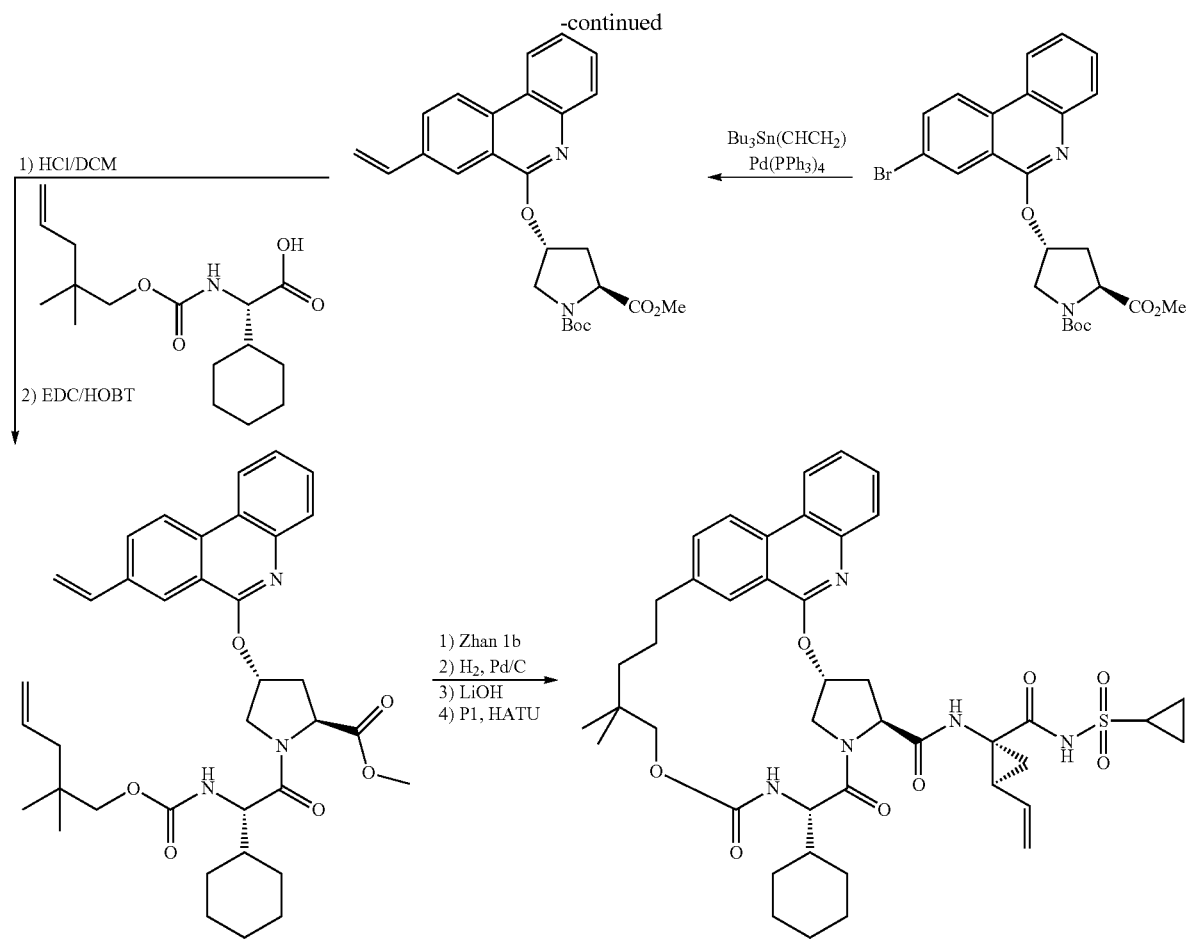

Example 1

(2R,4S,7S)-7-cyclohexyl-N-((1R,2S)-1-{[(cyclopropylsulfonyl)amino]carbonyl}-2-vinylcyclopropyl)-12,12-dimethyl-6,9-dioxo-3,4,6,7,8,9,12,13,14,15-decahydro-2H,11H-16,18-(ethanediylidene)-2,5-methano[1,10,3,6]dioxadiazacyclononadecino[11,12-b]quinoline-4-carboxamide

Step 1: (9Z)-2-bromo-9H-fluoren-9-one oxime

To a solution of 2-bromo-9H-fluoren-9-one (100 mg, 0.39 mmol) in EtOH (10 mL) and water (3 mL) was added hydroxylamine hydrochloride (54 mg, 0.77 mmol). The mixture was then heated to reflux for 1 h. The solvent was then removed in vacuo, and to the residue was added aqueous $NaHCO_3$. The solid was then filtered and dried to give the title product. LRMS $(M+H)^+$ 274.2.

Step 2: 8-bromophenanthridin-6-ol

To the solid product from Step 1, (9Z)-2-bromo-9H-fluoren-9-one oxime (106 mg, 0.387 mmol) was added polyphosphoric acid (5 g). The mixture was then heated to 185° C. for 2 h. After cooling to r.t., water was added and the resulting solid was collected by filtration to give a 1:1 mixture of the title compounds and the regioisomeric 3-bromophenanthridin-6-ol. LRMS $(M+H)^+$=274.2.

Step 3: 1-tert-butyl 2-methyl (2S,4R)-4-[(8-bromophenanthridin-6-yl)oxy]pyrrolidine-1,2-dicarboxylate To a solution of the product mixture from Step 2 (176 mg, 0.642 mmol) in NMP (1.5 mL) was added 1-tert-butyl 2-methyl (2S,4S)-4-{[(4-bromophenyl)sulfonyl]oxy}pyrrolidine-1,2-dicarboxylate (373 mg, 0.803 mmol) and $Cs_2CO_3$ (418 mg, 1.29 mmol). The mixture was then heated to 60° C. for 18 h, and worked up with water and EtOAc. The organic layer was washed with brine, dried over $MgSO_4$, and the solvent was removed in vacuo. The crude material was purified on silica (gradient elution, 10-50% EtOAc/hex) to yield the title compound as a 1:1 mixture with the expected regioisomer. LRMS $((M-Boc)+H)^+$=401.2.

Step 4: 1-tert-butyl 2-methyl (2S,4R)-4-[(8-vinylphenanthridin-6-yl)oxy]pyrrolidine-1,2-dicarboxylate To a degassed solution of the product mixture from Step 3 (320 mg, 0.64 mmol) in PhMe (5 mL) was added vinyltributyltin (0.225 mL, 0.77 mmol) and tetrakis(triphenylphosphine)palladium (74 mg, 0.06 mmol). The mixture was then heated to reflux for 18 h. The solvent was then removed in vacuo and the crude material was purified on silica (gradient elution, 5-50% EtOAc/hex) to provide the title compound as a 1:1 mixture with the expected regioisomer. LRMS $((M-Boc)+H)^+$=349.3.

Step 5: methyl (4R)-1-[(2S)-2-cyclohexyl-2-({[(2,2-dimethylpent-4-en-1-yl)oxy]carbonyl}amino)acetyl]-4-[(8-vinylphenanthridin-6-yl)oxy]-L-prolinate To a solution of the product mixture from Step 4 (100 mg, 0.26 mmol) in DCM (5 mL) was bubbled HCl(g) for 10 min. After stirring for an additional 30 min, the solvent was removed in vacuo to yield methyl (4R)-4-[(8-vinylphenanthridin-6-yl)oxy]-L-prolinate hydrochloride, which was taken up in DCM (5 mL) and linker intermediate B20, (2S)-cyclohexyl({[(2,2-dimethylpent-4-en-1-yl)oxy]carbonyl}amino)acetic acid (85 mg, 0.29 mmol), TEA (0.073 mL, 0.52 mmol), EDC (63 mg, 0.33 mmol), and HOBT (50 mg, 0.33 mmol) were added. The mixture was stirred at r.t. for 18 h, the solvent was removed in vacuo, and the residue was taken up in EtOAc and extracted with NaHCO$_3$. The organic layer was dried over MgSO$_4$ and the solvent was removed in vacuo. The crude material was then purified on silica (gradient elution, 10-50% EtOAc/hex) to yield the title compound as a 1:1 mixture with the expected regioisomer. LRMS (M+H)$^+$=628.4.

Step 6: methyl (2R,4S,7S,14E)-7-cyclohexyl-12,12-dimethyl-6,9-dioxo-3,4,6,7,8,9,12,13-octahydro-2H,11H-16,18-(ethanediylidene)-2,5-methano[1,10,3,6]dioxadiazacyclononadecino[11,12-b]quinoline-4-carboxylate To a degassed solution of the mixture from Step 5 (100 mg, 0.16 mmol) in DCE (20 mL) was added the Zhan 1b catalyst (12 mg, 0.016 mmol) and the mixture was stirred at r.t. for 18 h. The solvent was then removed in vacuo and the crude material was purified on silica (gradient elution, 10-50% EtOAc/hex) to yield the title compound as a single isomer. LRMS (M+H)$^+$=600.4.

Step 7: methyl (2R,4S,7S)-7-cyclohexyl-12,12-dimethyl-6,9-dioxo-3,4,6,7,8,9,12,13,14,15-decahydro-2H,11H-16,18-(ethanediylidene)-2,5-methano[1,10,3,6]dioxadiazacyclononadecino[11,12-b]quinoline-4-carboxylate To a solution of the product from Step 6, methyl (2R,4S,7S,14E)-7-cyclohexyl-12,12-dimethyl-6,9-dioxo-3,4,6,7,8,9,12,13-octahydro-2H,11H-16,18-(ethanediylidene)-2,5-methano[1,10,3,6]dioxadiazacyclononadecino[11,12-b]quinoline-4-carboxylate (47 mg, 0.078 mmol) in EtOH (5 mL) was added Pd/C (10%, 4 mg). The mixture was then placed under a H$_2$ atmosphere (balloon pressure) and stirred for 18 h. The mixture was then filtered and the solvent was removed in vacuo to yield the title compound. LRMS (M+H)$^+$=602.4.

Step 8: (2R,4S,7S)-7-cyclohexyl-12,12-dimethyl-6,9-dioxo-3,4,6,7,8,9,12,13,14,15-decahydro-2H,11H-16,18-(ethanediylidene)-2,5-methano[1,10,3,6]dioxadiazacyclononadecino[11,12-b]quinoline-4-carboxylic acid To a solution of the product from Step 7, methyl (2R,4S,7S)-7-cyclohexyl-12,12-dimethyl-6,9-dioxo-3,4,6,7,8,9,12,13,14,15-decahydro-2H,11H-16,18-(ethanediylidene)-2,5-methano[1,10,3,6]dioxadiazacyclononadecino[11,12-b]quinoline-4-carboxylate (47 mg, 0.078 mmol) in THF (2 mL) and water (2 mL) was added LiOH (19 mg, 0.78 mmol). The mixture was then heated to 70° C. for 30 min and 1N HCl was then added to neutralize the base. The mixture was then extracted with EtOAc, the organic layer was dried over MgSO$_4$, and the solvent was removed in vacuo to yield the title compound. LRMS (M+H)$^+$=588.5.

Step 9: (2R,4S,7S)-7-cyclohexyl-N-((1R,2S)-1-{[(cyclopropylsulfonyl)amino]carbonyl}-2-vinylcyclopropyl)-12,12-dimethyl-6,9-dioxo-3,4,6,7,8,9,12,13,14,15-decahydro-2H,11H-16,18-(ethanediylidene)-2,5-methano[1,10,3,6]dioxadiazacyclononadecino[11,12-b]quinoline-4-carboxamide To a solution of the product from Step 8, (2R,4S,7S)-7-cyclohexyl-12,12-dimethyl-6,9-dioxo-3,4,6,7,8,9,12,13,14,15-decahydro-2H,11H-16,18-(ethanediylidene)-2,5-methano[1,10,3,6]dioxadiazacyclononadecino[11,12-b]quinoline-4-carboxylic acid (45 mg, 0.077 mmol) in DMF (1 mL) was added acylsulfonamide intermediate A1 (27 mg, 0.1 mmol), DIPEA (0.04 mL, 0.23 mmol), and HATU (38 mg, 0.1 mmol). After 20 min, the mixture was purified directly by reverse phase chromatography (100×30 mm, 40-95% ACN/0.15% aq. TFA) to give the title compound as a white solid. LRMS (M+H)$^+$=800.6.

Scheme 2

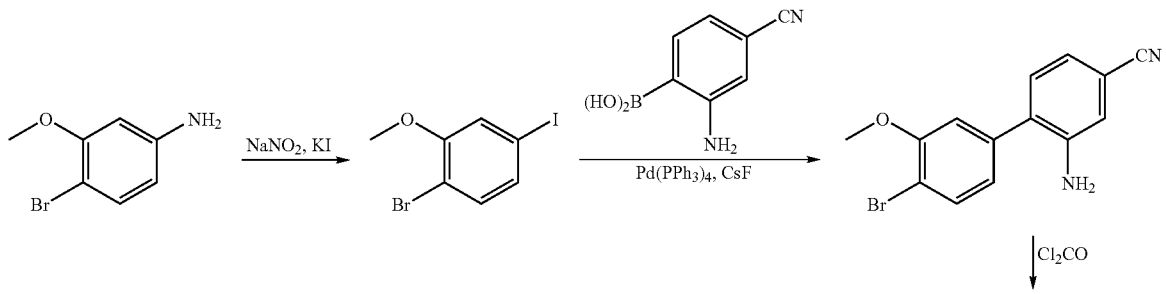

-continued
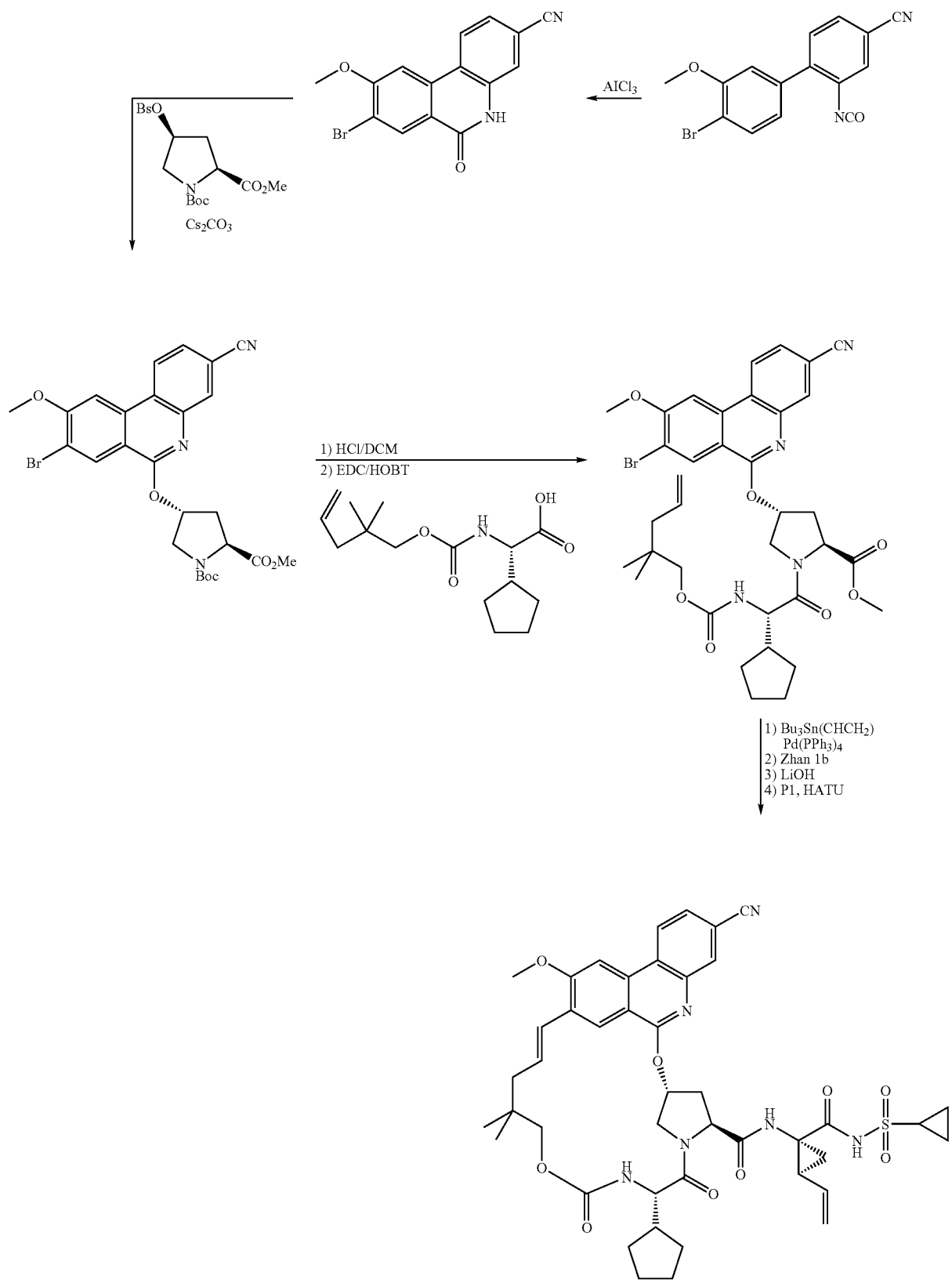

Example 2

(2R,4S,7S,14E)-21-cyano-7-cyclopentyl-N-((1R,2S)-1-{[(cyclopropylsulfonyl)amino]carbonyl}-2-vinylcyclopropyl)-25-methoxy-12,12-dimethyl-6,9-dioxo-3,4,6,7,8,9,12,13-octahydro-2H,11H-16,18-(ethanediylidene)-2,5-methano[1,10,3,6]dioxadiazacyclononadecino[11,12-b]quinoline-4-carboxamide

Step 1: 1-tert-butyl 2-methyl (2S,4R)-4-[(8-bromo-3-cyano-9-methoxyphenanthridin-6-yl)oxy]pyrrolidine-1,2-dicarboxylate To a solution of 8-bromo-9-methoxy-6-oxo-5,6-dihydrophenanthridine-3-carbonitrile (C1), 8-bromo-9-methoxy-6-oxo-5,6-dihydrophenanthridine-3-carbonitrile (354 mg, 1.07 mmol) in NMP (10 mL) was added 1-tert-butyl 2-methyl (2S,4S)-4-{[(4-bromophenyl)sulfonyl]oxy}pyrrolidine-1,2-dicarboxylate (549 mg, 1.18 mmol) and $Cs_2CO_3$ (876 mg, 2.69 mmol). The mixture was then heated to 60° C. for 18 h, and worked up with water and EtOAc. The organic layer was washed with brine, dried over $MgSO_4$, and the solvent was removed in vacuo. The crude material was purified on silica (gradient elution, 10-50% EtOAc/hex) to yield the title compound. LRMS ((M-Boc)+H)$^+$=456.2.

Step 2: methyl (4R)-4-[(8-bromo-3-cyano-9-methoxyphenanthridin-6-yl)oxy]-1-[(2S)-2-cyclopentyl-2-({[(2,2-dimethylpent-4-en-1-yl)oxy]carbonyl}amino)acetyl]-L-prolinate To a solution of the product mixture from Step 1, 1-tert-butyl 2-methyl (2S,4R)-4-[(8-bromo-3-cyano-9-methoxyphenanthridin-6-yl)oxy]pyrrolidine-1,2-dicarboxylate (419 mg, 0.75 mmol) in DCM (10 mL) was bubbled HCl(g) for 20 min. After stirring for an additional 30 min, the solvent was removed in vacuo to yield methyl (4R)-4-[(8-bromo-3-cyano-9-methoxyphenanthridin-6-yl)oxy]-L-prolinate hydrochloride, which was taken up in DCM (5 mL) and linker intermediate B21, (2S)-cyclopentyl({[(2,2-dimethylpent-4-en-1-yl)oxy]carbonyl}amino)acetic acid (234 mg, 0.83 mmol), TEA (0.314 mL, 2.25 mmol), EDC (187 mg, 0.98 mmol), and HOBT (149 mg, 0.98 mmol) were added. The mixture was stirred at r.t. for 18 h, the solvent was removed in vacuo, and the residue was taken up in EtOAc and extracted with $NaHCO_3$. The organic layer was dried over $MgSO_4$ and the solvent was removed in vacuo. The crude material was then purified on silica (gradient elution, 0-10% EtOAc/MeOH/$NH_3$) to yield the title compound. LRMS (M+H)$^+$=721.4.

Step 3: methyl (4R)-4-[(3-cyano-9-methoxy-8-vinylphenanthridin-6-yl)oxy]-1-[(2S)-2-cyclopentyl-2-({[(2,2-dimethylpent-4-en-1-yl)oxy]carbonyl}amino)acetyl]-L-prolinate To a degassed solution of the product mixture from Step 2, methyl (4R)-4-[(8-bromo-3-cyano-9-methoxyphenanthridin-6-yl)oxy]-1-[(2S)-2-cyclopentyl-2-({[(2,2-dimethylpent-4-en-1-yl)oxy]carbonyl}amino)acetyl]-L-prolinate (420 mg, 0.58 mmol) in PhMe (10 mL) was added vinyltributyltin (0.205 mL, 0.70 mmol) and tetrakis(triphenylphosphine)palladium (67 mg, 0.06 mmol). The mixture was then heated to reflux for 18 h. The solvent was then removed in vacuo and the crude material was purified on silica (gradient elution, 10-50% EtOAc/hex) to provide the title compound. LRMS (M+H)$^+$=669.3.

Step 4: methyl (2R,4S,7S,14E)-21-cyano-7-cyclopentyl-25-methoxy-12,12-dimethyl-6,9-dioxo-3,4,6,7,8,9,12,13-octahydro-2H,11H-16,18-(ethanediylidene)-2,5-methano[1,10,3,6]dioxadiazacyclononadecino[11,12-b]quinoline-4-carboxylate To a degassed solution of the mixture from Step 3, methyl (4R)-4-[(3-cyano-9-methoxy-8-vinylphenanthridin-6-yl)oxy]-1-[(2S)-2-cyclopentyl-2-({[(2,2-dimethylpent-4-en-1-yl)oxy]carbonyl}amino)acetyl]-L-prolinate (306 mg, 0.45 mmol) in DCE (60 mL) was added the Zhan 1b catalyst (33 mg, 0.05 mmol) and the mixture was stirred at 70° C. for 2 h. The solvent was then removed in vacuo and the crude material was purified on silica (gradient elution, 10-50% EtOAc/hex) to yield the title compound. LRMS (M+H)$^+$=641.4.

Step 5: (2R,4S,7S,14E)-21-cyano-7-cyclopentyl-25-methoxy-12,12-dimethyl-6,9-dioxo-3,4,6,7,8,9,12,13-octahydro-2H,11H-16,18-(ethanediylidene)-2,5-methano[1,10,3,6]dioxadiazacyclononadecino[11,12-b]quinoline-4-carboxylic acid To a solution of the product from Step 4, methyl (2R,4S,7S,14E)-21-cyano-7-cyclopentyl-25-methoxy-12,12-dimethyl-6,9-dioxo-3,4,6,7,8,9,12,13-octahydro-2H,11H-16,18-(ethanediylidene)-2,5-methano[1,10,3,6]dioxadiazacyclononadecino[11,12-b]quinoline-4-carboxylate (277 mg, 0.43 mmol) in THF (5 mL) and water (5 mL) was added LiOH (155 mg, 6.48 mmol). The mixture was then heated to 65° C. for 30 min and 1N HCl was then added to neutralize the base. The mixture was then extracted with EtOAc, the organic layer was dried over $MgSO_4$, and the solvent was removed in vacuo to yield the title compound. LRMS (M+H)$^+$=627.4.

Step 6: (2R,4S,7S,14E)-21-cyano-7-cyclopentyl-N-((1R,2S)-1-{[(cyclopropylsulfonyl)amino]carbonyl}-2-vinylcyclopropyl)-25-methoxy-12,12-dimethyl-6,9-dioxo-3,4,6,7,8,9,12,13-octahydro-2H,11H-16,18-(ethanediylidene)-2,5-methano[1,10,3,6]dioxadiazacyclononadecino[11,12-b]quinoline-4-carboxamide To a solution of the product from Step 5, (2R,4S,7S,14E)-21-cyano-7-cyclopentyl-25-methoxy-12,12-dimethyl-6,9-dioxo-3,4,6,7,8,9,12,13-octahydro-2H,11H-16,18-(ethanediylidene)-2,5-methano[1,10,3,6]dioxadiazacyclononadecino[11,12-b]quinoline-4-carboxylic acid (80 mg, 0.13 mmol) in DMF (2 mL) was added acylsulfonamide intermediate A1 (43 mg, 0.16 mmol), DIPEA (0.067 mL, 0.38 mmol), and HATU (68 mg, 0.18 mmol). After 30 min, the mixture was purified directly by reverse phase chromatography (100×30 mm, 40-95% ACN/0.15% aq. TFA) to give the title compound as a white solid. LRMS (M+H)$^+$=839.4.

Example 3

(2R,4S,7S)-21-cyano-7-cyclopentyl-N-((1R,2S)-1-{[(cyclopropylsulfonyl)amino]carbonyl}-2-vinylcyclopropyl)-25-methoxy-12,12-dimethyl-6,9-dioxo-3,4,6,7,8,9,12,13,14,15-decahydro-2H,11H-16,18-(ethanediylidene)-2,5-methano[1,10,3,6]dioxadiazacyclononadecino[11,12-b]quinoline-4-carboxamide Step 1: (2R,4S,7S)-21-cyano-7-cyclopentyl-25-methoxy-12,12-dimethyl-6,9-dioxo-3,4,6,7,8,9,12,13,14,15-decahydro-2H,11H-16,18-(ethanediylidene)-2,5-methano[1,10,3,6]dioxadiazacyclononadecino[11,12-b]quinoline-4-carboxylic acid To a solution of (2R,4S,7S,14E)-21-cyano-7-cyclopentyl-25-methoxy-12,12-dimethyl-6,9-dioxo-3,4,6,7,8,9,12,13-octahydro-2H,11H-16,18-(ethanediylidene)-2,5-methano[1,10,3,6]dioxadiazacyclononadecino[11,12-b]quinoline-4-carboxylic acid (Example 2, Step 5, 130 mg, 0.207 mmol) in THF (10 mL) was added Pd/C (10%, 13 mg). The mixture was then placed under a $H_2$ atmosphere (balloon pressure) and stirred for 2 h. The mixture was then filtered and the solvent was removed in vacuo to yield the title compound. LRMS $(M+H)^+$=629.4.

Step 2: (2R,4S,7S)-21-cyano-7-cyclopentyl-N-((1R,2S)-1-{[(cyclopropylsulfonyl)amino]carbonyl}-2-vinylcyclopropyl)-25-methoxy-12,12-dimethyl-6,9-dioxo-3,4,6,7,8,9,12,13,14,15-decahydro-2H,11H-16,18-(ethanediylidene)-2,5-methano[1,10,3,6]dioxadiazacyclononadecino[11,12-b]quinoline-4-carboxamide To a solution of the product from Step 1, (2R,4S,7S)-21-cyano-7-cyclopentyl-25-methoxy-12,12-dimethyl-6,9-dioxo-3,4,6,7,8,9,12,13,14,15-decahydro-2H,11H-16,18-(ethanediylidene)-2,5-methano[1,10,3,6]dioxadiazacyclononadecino[11,12-b]quinoline-4-carboxylic acid (130 mg, 0.21 mmol) in DMF (2 mL) was added acylsulfonamide intermediate A1 (69 mg, 0.26 mmol), DIPEA (0.11 mL, 0.62 mmol), and HATU (110 mg, 0.29 mmol). After 30 min, the mixture was purified directly by reverse phase chromatography (100×30 mm, 40-95% ACN/0.15% aq. TFA) to give the title compound as a white solid. LRMS $(M+H)^+$=841.6.

Example 4

(3R,5S,8S)-8-cyclohexyl-N-((1R,2S)-1-{[(cyclopropylsulfonyl)amino]carbonyl}-2-vinylcyclopropyl)-18-methoxy-13,13-dimethyl-7,10-dioxo-2,11-dioxa-6,9,27-triazapentacyclo[15.10.2.1$^{3,6}$.0$^{20,28}$.0$^{21,26}$]triaconta-1(27),15,17,19,21(26),28-hexaene-5-carboxamide Step 1: (4R)-4-[(8-bromo-9-methoxy-1,2,3,4-tetrahydrophenanthridin-6-yl)oxy]-1-(tert-butoxycarbonyl)-L-proline To a solution of (4R)-1-(tert-butoxycarbonyl)-4-hydroxy-L-proline (639 mg, 2.76 mmol) in DMSO (10 mL) was added KOtBu (873 mg, 7.78 mmol) at r.t. The temperature rose to 32° C. and the reaction was stirred for 30 min. The solution was cooled to ~13° C. and the intermediate C8, 8-bromo-6-chloro-9-methoxy-1,2,3,4-tetrahydrophenanthridine (820 mg, 2.51 mmol) was added in 8 mL of DMSO slurry) over 5 min. The ice bath was removed and the mixture was allowed to stir for 1 h. The reaction was slowly quenched into a well-stirred mixture of aqueous citric acid (150 mL) and allowed to stir at r.t. for 30 min. The resulting solids were filtered, dissolved with EtOAc, washed with $H_2O$/KHSO$_4$, dried over $Na_2SO_4$, and the solvent was removed in vacuo to yield the title compound. LRMS $(M+H)^+$=520.9.

Step 2: ethyl (4R)-4-[(8-bromo-9-methoxy-1,2,3,4-tetrahydrophenanthridin-6-yl)oxy]-L-prolinate hydrochloride To a solution of the product from Step 1, (4R)-4-[(8-bromo-9-methoxy-1,2,3,4-tetrahydrophenanthridin-6-yl)oxy]-1-(tert-butoxycarbonyl)-L-proline (500 mg, 0.96 mmol) in EtOH (80 mL) was bubbled HCl (g) for 30 min. The mixture was then stirred for 2 days at r.t. and then the solvent was removed in vacuo to yield the title compound. LRMS $(M+H)^+$=448.9.

Step 3: ethyl (4R)-4-[(8-bromo-9-methoxy-1,2,3,4-tetrahydrophenanthridin-6-yl)oxy]-1-[(2S)-2-cyclohexyl-2-({[(2,2-dimethylpent-4-en-1-yl)oxy]carbonyl}amino)acetyl]-L-prolinate To a solution of the product from Step 2, ethyl (4R)-4-[(8-bromo-9-methoxy-1,2,3,4-tetrahydrophenanthridin-6-yl)oxy]-L-prolinate hydrochloride (466 mg, 0.96 mmol) in DMF (8 mL) was added linker intermediate B20, (2S)-cyclohexyl({[(2,2-dimethylpent-4-en-1-yl)oxy]carbonyl}amino)acetic acid (300 mg, 1.0 mmol)), DIPEA (0.50 mL, 2.88 mmol), HATU (547 mg, 1.44 mmol), and DMAP (59 mg, 0.48 mmol) were added. The mixture was stirred at r.t. for 18 h and then the mixture was poured into 120 mL of aqueous citric acid. The resulting solid was removed by filtration and washed with water. The solid was then dissolved in EtOAc, dried over $Na_2SO_4$, and the solvent was removed in vacuo. The crude material was then purified on silica (gradient elution, 20-50% EtOAc/hexanes) to yield the title compound. LRMS $(M+H)^+$=728.0.

Step 4: (3R,5S,8S)-8-cyclohexyl-18-methoxy-13,13-dimethyl-7,10-dioxo-2,11-dioxa-6,9,27-triazapentacyclo[15.10.2.1$^{3,6}$.0$^{20,28}$.0$^{21,26}$]triaconta-1(27),15,17,19,21(26),28-hexaene-5-carboxylic acid Using the product from Step 3, ethyl (4R)-4-[(8-bromo-9-methoxy-1,2,3,4-tetrahydrophenanthridin-6-yl)oxy]-1-[(2S)-2-cyclohexyl-2-({[(2,2-dimethylpent-4-en-1-yl)oxy]carbonyl}amino)acetyl]-L-prolinate, the title compound was prepared according to Example 2, Steps 6-8. LRMS $(M+H)^+$=620.0.

Step 5: (3R,5S,8S)-8-cyclohexyl-N-((1R,2S)-1-{[(cyclopropylsulfonyl)amino]carbonyl}-2-vinylcyclopropyl)-18-methoxy-13,13-dimethyl-7,10-dioxo-2,11-dioxa-6,9,27-triazapentacyclo[15.10.2.1$^{3,6}$.0$^{20,28}$.0$^{21,26}$]triaconta-1(27),15,17,19,21(26),28-hexaene-5-carboxamide Using the product from Step 4, (3R,5S,8S)-8-cyclohexyl-18-methoxy-13,13-dimethyl-7,10-dioxo-2,11-dioxa-6,9,27-triazapentacyclo[15.10.2.1$^{3,6}$]triaconta-1(27), 15,17,19,21(26),28-hexaene-5-carboxylic acid, the title compound was prepared according to Step 9, Example 2. LRMS (M+H)$^+$=832.2.

Example 5

(3R,5S,8S)-8-cyclohexyl-N-((1R,2S)-1-{[(cyclopropylsulfonyl)amino]carbonyl}-2-vinylcyclopropyl)-18-methoxy-13,13-dimethyl-7,10-dioxo-2,11-dioxa-6,9,27-triazapentacyclo[15.10.2.1$^{3,6}$.0$^{20,28}$.0$^{21,26}$]triaconta-1(27),17,19,21(26),28-pentaene-5-carboxamide Using the product from Step 4, Example 4, (3R,5S,8S)-8-cyclohexyl-18-methoxy-13,13-dimethyl-7,10-dioxo-2,11-dioxa-6,9,27-triazapentacyclo[15.10.2.1$^{3,6}$.0$^{20,28}$.0$^{21,26}$]triaconta-1(27),15,17,19,21(26),28-hexaene-5-carboxylic acid, the title compound was prepared according to Example 3, Steps 1-2. LRMS (M+H)$^+$=834.2.

The following examples were prepared using a procedure similar to that described for Examples 2 and 3, starting with the appropriate intermediates A, B, and C indicated.

Compounds in Table 1 having a basic group or acidic group are depicted and named as the free base or acid. Depending on the reaction and purification conditions, various compounds in Table 1 having a basic group were isolated in either the free base form, or as a salt (such as HCl salt), or in both free base and salt forms. Various compounds in the table having an acid group were isolated in either the acid form, or as a salt (such as Na salt), or in both acid and salt forms.

| Ex. | Name | LRMS (M + H)+ | Procedure | Intermediates |
|---|---|---|---|---|
| 6 | (2R,4S,7S)-7-cyclopentyl-N—((1R,2S)-1-{[(cyclopropylsulfonyl)amino]carbonyl}-2-vinylcyclopropyl)-25-methoxy-12,12-dimethyl-6,9-dioxo-3,4,6,7,8,9,12,13,14,15-decahydro-2H,11H-16,18-(ethanediylidene)-2,5-methano[1,10,3,6]dioxadiazacyclononadecino[11,12-b]quinoline-4-carboxamide | 816.4 | 3 | B21, C3, A1 |
| 7 | (2R,4S,7S)-7-cyclopentyl-N—((1R,2S)-1-{[(cyclopropylsulfonyl)amino]carbonyl}-2-vinylcyclopropyl)-25-methoxy-12,12,21-trimethyl-6,9-dioxo-3,4,6,7,8,9,12,13,14,15-decahydro-2H,11H-16,18-etheno-2,5-methano[1,10,3,6]dioxadiazacyclononadecino[11,12-b]quinoline-4-carboxamide | 830.3 | 3 | C4, B21, A1 |
| 8 | (2R,4S,7S,14E)-7-cyclohexyl-N—((1R,2S)-1-{[(cyclopropylsulfonyl)amino]carbonyl}-2-vinylcyclopropyl)-25-methoxy-10,12,12-trimethyl-6,9-dioxo-3,4,6,7,8,9,10,11,12,13-decahydro-2H-16,18-etheno-2,5-methano[1,5,8,10]oxatriazacyclo nonadecino[19,18-b]quinoline-4-carboxamide | 841.3 | 2 | C3, B27, A1 |
| 9 | (2R,4S,7S,14Z)-7-cyclohexyl-N—((1R,2S)-1-{[(cyclopropylsulfonyl)amino]carbonyl}-2-vinylcyclopropyl)-25-methoxy-10,12,12-trimethyl-6,9-dioxo-3,4,6,7,8,9,10,11,12,13-decahydro-2H-16,18-etheno-2,5-methano [1,5,8,10]oxatriazacyclononadecino[19,18-b]quinoline-4-carboxamide | 841.3 | 2 | C3, B27, A1 |
| 10 | (2R,4S,7S)-7-cyclohexyl-N—((1R,2S)-1-{[(cyclopropylsulfonyl)amino]carbonyl}-2-vinylcyclopropyl)-25-methoxy-10,12,12-trimethyl-6,9-dioxo-3,4,6,7,8,9,10,11,12,13,14,15-dodecahydro-2H-16,18-etheno-2,5-methano[1,5,8,10]oxatriazacyclononadecino[19,18-b]quinoline-4-carboxamide | 843.4 | 3 | C3, B27, A1 |
| 11 | (3aR,7S,10S,12R,24aR)-7-cyclohexyl-N—((1R,2S)-1-{[(cyclopropylsulfonyl)amino]carbonyl}-2-vinylcyclopropyl)-25-methoxy-5,8-dioxo-1,2,3,3a,5,6,7,8,11,12,22,23,24,24a-tetradecahydro-10H-19,21-etheno-9,12-methanocyclopenta[18,19][1,10,3,6]dioxadiazacyclononadecino[11,12-b]quinoline-10-carboxamide | 842.3 | 3 Separate | C3, B22, A1 |
| 12 | (3aS,7S,10S,12R,24aS)-7-cyclohexyl-N—((1R,2S)-1-{[(cyclopropylsulfonyl)amino]carbonyl}-2-vinylcyclopropyl)-25-methoxy-5,8-dioxo-1,2,3,3a,5,6,7,8,11,12,22,23,24,24a-tetradecahydro-10H-19,21-etheno-9,12-methanocyclopenta[18,19][1,10,3,6]dioxadiazacyclononadecino[11,12-b]quinoline-10-carboxamide | 842.3 | 3 Separate | C3, B22, A1 |
| 13 | (2R,4S,7S,14E)-20-chloro-7-cyclopentyl-N—((1R,2S)-1-{[(cyclopropylsulfonyl)amino]carbonyl}-2-vinylcyclo propyl)-25-methoxy-12,12-dimethyl-6,9-dioxo-3,4,6,7,8,9,12,13-octahydro-2H,11H-16,18-etheno-2,5-methano[1,10,3,6]dioxadiazacyclononadecino[11,12-b]quinoline-4-carboxamide | 848.4 | 2 | C6, B21, A1 |
| 14 | (2R,4S,7S)-20-chloro-7-cyclopentyl-N—((1R,2S)-1-{[(cyclopropylsulfonyl)amino]carbonyl}-2-vinylcyclopropyl)-25-methoxy-12,12-dimethyl-6,9-dioxo-3,4,6,7,8,9,12,13,14,15-decahydro-2H,11H-16,18-etheno-2,5-methano[1,10,3,6]dioxadiazacyclononadecino[11,12-b]quinoline-4-carboxamide | 850.3 | 3 | C6, B21, A1 |
| 15 | (2R,4S,7S)-7-cyclopentyl-N—((1R,2S)-1-{[(cyclopropylsulfonyl)amino]carbonyl}-2-vinylcyclopropyl)-21-fluoro-25-methoxy-12,12-dimethyl-6,9-dioxo-3,4,6,7,8,9,12,13,14,15-decahydro-2H,11H-16,18-(ethanediylidene)-2,5-methano[1,10,3,6]dioxadiazacyclononadecino[11,12-b]quinoline-4-carboxamide | 834.3 | 3 | C5, B21, A1 |
| 16 | (2R,4S,7S,14E)-7-cyclopentyl-N—((1R,2S)-1-{[(cyclopropylsulfonyl)amino]carbonyl}-2-vinylcyclopropyl)-21,25-dimethoxy-12,12- | 844.5 | 2 | C2, B21, |

-continued

| Ex. | Name | LRMS (M + H)+ | Procedure | Intermediates |
|---|---|---|---|---|
| | dimethyl-6,9-dioxo-3,4,6,7,8,9,12,13-octahydro-2H,11H-16,18-(ethanediylidene)-2,5-methano[1,10,3,6]dioxadiazacyclononadecino[11,12-b]quinoline-4-carboxamide | | | A1 |
| 17 | (2R,4S,7S)-7-cyclopentyl-N—((1R,2S)-1-{[(cyclopropylsulfonyl)amino]carbonyl}-2-vinylcyclopropyl)-21,25-dimethoxy-12,12-dimethyl-6,9-dioxo-3,4,6,7,8,9,12,13,14,15-decahydro-2H,11H-16,18-(ethanediylidene)-2,5-methano[1,10,3,6]dioxadiazacyclononadecino[11,12-b]quinoline-4-carboxamide | 846.4 | 3 | C2, B21, A1 |
| 18 | (3R,5S,8S)-8-cyclopentyl-N—((1R,2S)-1-{[(cyclopropylsulfonyl)amino]carbonyl}-2-vinylcyclopropyl)-26-ethoxy-13,13-dimethyl-7,10-dioxo-2,11-dioxa-6,9,25-triazapentacyclo[15.10.2.13,6.018,23.024,28]triaconta-1(27),15,17,19,21,23,25,28-octaene-5-carboxamide | 828.4 | 2 | C7, B21, A1 |
| 19 | (3R,5S,8S)-8-tert-butyl-N—((1R,2S)-1-{[(cyclopropylsulfonyl)amino]carbonyl}-2-vinylcyclopropyl)-18-methoxy-13,13-dimethyl-7,10-dioxo-2,11-dioxa-6,9,27-triazapentacyclo[15.10.2.13,6.020,28.021,26]triaconta-1(27),15,17,19,21(26),28-hexaene-5-carboxamide | 806.1 | 4 | C8, B23, A1 |
| 20 | (3R,5S,8S)-8-cyclohexyl-N—((1R,2R)-1-{[(cyclopropylsulfonyl)amino]carbonyl}-2-ethylcyclopropyl)-18-methoxy-13,13-dimethyl-7,10-dioxo-2,11-dioxa-6,9,27-triazapentacyclo[15.10.2.13,6.020,28.021,26]triaconta-1(27),17,19,21(26),28-pentaene-5-carboxamide | 836.2 | 5 | C8, B20, A3 |
| 21 | (3R,5S,8S)-8-cyclohexyl-N—((1R,2R)-1-{[(cyclopropylsulfonyl)amino]carbonyl}-2-ethylcyclopropyl)-18-methoxy-13,13-dimethyl-7,10-dioxo-2,11-dioxa-6,9,27-triazapentacyclo[15.10.2.13,6.020,28.021,26]triaconta-1(27),15,17,19,21(26),28-hexaene-5-carboxamide | 834.2 | 4 | C8, B20, A3 |
| 22 | (3R,5S,8S)-8-cyclohexyl-N—((1R,2S)-1-{[(cyclopropylsulfonyl)amino]carbonyl}-2-vinylcyclo propyl)-18-methoxy-13,13-dimethyl-7,10-dioxo-2,11-dioxa-6,9,26-triazapentacyclo[15.9.2.13,6.020,27.021,25]nonacosa-1(26),17,19,21(25),27-pentaene-5-carboxamide | 820.1 | 5 | C9, B20, A1 |
| 23 | (2R,4S,7S,14E)-7-cyclohexyl-N—((1R,2S)-1-{[(cyclopropylsulfonyl)amino]carbonyl}-2-vinylcyclopropyl)-24-methoxy-12,12-dimethyl-6,9-dioxo-3,4,6,7,8,9,12,13-octahydro-2H,11H-16,18-etheno-2,5-methanothieno[3',2':5,6]pyrido[2,3-k][1,10,3,6]dioxadiazacyclononadecine-4-carboxamide | 834 | 2 | A1, B20, C12 |
| 24 | (2R,4S,7S)-7-cyclohexyl-N—((1R,2S)-1-{[(cyclopropylsulfonyl)amino]carbonyl}-2-vinylcyclopropyl)-24-methoxy-12,12-dimethyl-6,9-dioxo-3,4,6,7,8,9,12,13,14,15-decahydro-2H,11H-16,18-etheno-2,5-methano thieno[3',2':5,6]pyrido[2,3-k][1,10,3,6]dioxadiazacyclononadecine-4-carboxamide | 836 | 2 (steps 1-4) then 3 | A2, B20, C12 |
| 25 | (2R,4S,7S,14E)-7-butyl-N—((1R,2S)-1-{[(cyclopropylsulfonyl)amino carbonyl}-2-vinylcyclopropyl)-24-methoxy-12,12-dimethyl-6,9-dioxo-3,4,6,7,8,9,12,13-octahydro-2H,11H-16,18-(ethanediylidene)-2,5-methanothieno[3',2':5,6]pyrido[2,3-k][1,10,3,6]dioxadiazacyclo nonadecine-4-carboxamide | 808.4 | 2 | A1, B24, C12 |
| 26 | (2R,4S,7S,14E)-7-cyclopentyl-N—((1R,2S)-1-{[(cyclopropylsulfonyl)amino]carbonyl}-2-vinylcyclopropyl)-24-methoxy-12,12-dimethyl-6,9-dioxo-3,4,6,7,8,9,12,13-octahydro-2H,11H-16,18-(ethanediylidene)-2,5-methanothieno[3',2':5,6]pyrido [2,3-k][1,10,3,6]dioxadiazacyclo nonadecine-4-carboxamide | 820.4 | 2 | A1, B21, C12 |
| 27 | (2R,4S,7S,14E)-7-tert-butyl-N—((1R,2S)-1-{[(cyclopropylsulfonyl)amino]carbonyl}-2-vinylcyclopropyl)-24-methoxy-12,12-dimethyl-6,9-dioxo-3,4,6,7,8,9,12,13-octahydro-2H,11H-16,18-(ethanediylidene)-2,5-methanothieno[3',2':5,6]pyrido [2,3-k][1,10,3,6]dioxadiazacyclo nonadecine-4-carboxamide | 808.4 | 2 | A1, B23, C12 |
| 28 | (4E,13S,16S,18R)-13-tert-butyl-N—((1R,2S)-1-{[(cyclopropylsulfonyl) amino]carbonyl}-2-vinylcyclopropyl)-1,8,8-trimethyl-11,14-dioxo-6,7,8,9,11,12,13,14,17,18-decahydro-3H,16H-15,18-methano-10,19-dioxa-2a,12,15,20-tetraazabenzo[g]cycloicosa[1,2,3-cd]indene-16-carboxamide | 803.6 | 2 (omit step 3) | A1, B13, C10 |
| 29 | (13S,16S,18R)-13-tert-butyl-N—((1R,2S)-1-{[(cyclopropylsulfonyl)amino]carbonyl}-2-vinylcyclo propyl)-1,8,8-trimethyl-11,14-dioxo-4,5,6,7,8,9,11,12,13,14,17,18-dodecahydro-3H,16H-15,18-methano-10,19-dioxa-2a,12,15,20-tetraazabenzo[g]cycloicosa[1,2,3-cd]indene-16-carboxamide | 805.6 | 2 (steps 1, 2, 4) then 3 | A1, B13, C10 |
| 30 | (4E,12S,15S,17R)-12-tert-butyl-N—((1R,2S)-1-{[(cyclopropylsulfonyl) amino]carbonyl}-2-vinylcyclo propyl)-1,7,7-trimethyl-10,13-dioxo-3,6,7,8,10,11,12,13,16,17-decahydro-15H-14,17-methano-9,18-dioxa-2a,11,14,19-tetraazabenzo[g]cyclononadeca[1,2,3-cd]indene-15-carboxamide | 789.7 | 2 (omit step 3) | A1, B23, C10 |
| 31 | (4E,14S,17S,19R)-14-cyclopentyl-N—((1R,2S)-1-{[(cyclopropylsulfonyl) amino]carbonyl}-2-vinylcyclopropyl)-1,9,9-trimethyl-12,15-dioxo-3,6,7,8,9,10,12,13,14,15,18,19-dodecahydro- | 830 | 2 (omit step 3) | A1, B25, C10 |

| Ex. | Name | LRMS (M + H)+ | Procedure | Intermediates |
|---|---|---|---|---|
|  | 17H-16,19-methano-11,20-dioxa-2a,13,16,21-tetraazabenzo[g]cyclohenicosa[1,2,3-cd]indene-17-carboxamide |  |  |  |
| 32 | (4E,14S,17S,19R)-14-cyclopentyl-N—((1R,2S)-1-{[(cyclopropylsulfonyl) amino]carbonyl}-2-vinylcyclo propyl)-1,11-dimethyl-12,15-dioxo-6,7,8,9,10,11,12,13,14,15,18,19-dodecahydro-3H,17H-16,19-methano-20-oxa-2a,11,13,16,21-pentaazabenzo[g]cyclohenicosa[1,2,3-cd]indene-17-carboxamide | 815 | 2 (omit step 3) | A1, B28, C10 |
| 33 | (14S,17S,19R)-14-cyclopentyl-N—((1R,2S)-1-{[(cyclopropylsulfonyl) amino]carbonyl}-2-vinylcyclopropyl)-1,9,9-trimethyl-12,15-dioxo-3,4,5,6,7,8,9,10,12,13,14,15,18,19-tetradecahydro-17H-16,19-methano-11,20-dioxa-2a,13,16,21-tetraazabenzo[g]cyclohenicosa[1,2,3-cd]indene-17-carboxamide | 832 | 2 (steps 1, 2, 4) then 3 | A1, B25, C10 |
| 34 | (14S,17S,19R)-14-cyclopentyl-N—((1R,2S)-1-{[(cyclopropylsulfonyl) amino]carbonyl}-2-vinylcyclopropyl)-1,11-dimethyl-12,15-dioxo-4,5,6,7,8,9,10,11,12,13,14,15,18,19-tetradecahydro-3H,17H-16,19-methano-20-oxa-2a,11,13,16,21-pentaazabenzo[g]cyclohenicosa[1,2,3-cd]indene-17-carboxamide | 817 | 2 (steps 1, 2, 4) then 3 | A1, B28, C10 |
| 35 | (12S,15S,17R)-12-tert-butyl-N—((1R,2S)-1-{[(cyclopropylsulfonyl)amino]carbonyl}-2-vinylcyclopropyl)-1,7,7-trimethyl-10,13-dioxo-3,4,5,6,7,8,10,11,12,13,16,17-dodecahydro-15H-14,17-methano-9,18-dioxa-2a,11,14,19-tetraazabenzo[g]cyclononadeca[1,2,3-cd]indene-15-carboxamide | 791 | 2 (steps 1, 2, 4) then 3 | A1, B23, C10 |
| 36 | (4E,13S,16S,18R)-13-tert-butyl-N—((1R,2S)-1-{[(cyclopropylsulfonyl) amino]carbonyl}-2-vinylcyclo propyl)-22-methoxy-1,8,8-trimethyl-11,14-dioxo-6,7,8,9,11,12,13,14,17,18-decahydro-3H,16H-15,18-methano-10,19-dioxa-2a,12,15,20-tetraazabenzo[g]cycloicosa[1,2,3-cd]indene-16-carboxamide | 834 | 2 (omit step 3) | A1, B13, C11 |
| 37 | (3R,5S,8S)-8-cyclopentyl-N—((1R,2S)-1-{[(cyclopropylsulfonyl)amino]carbonyl}-2-vinylcyclopropyl)-26-ethoxy-13,13-dimethyl-7,10-dioxo-2,11-dioxa-6,9,25-triazapentacyclo[15.10.2.13,6.018,23.024,28]triaconta-1(27),17,9,21,23,25,28-heptaene-5-carboxamide | 830.5 | 3 | C7, B21, A1 |

Example 38

(3R,5S,8S)-8-cyclohexyl-N-((1R,2S)-1-{[(cyclopropylsulfonyl)amino]carbonyl}-2-vinylcyclopropyl)-18-methoxy-13,13-dimethyl-7,10-dioxo-2,11-dioxa-6,9,21,24-tetraazapentacyclo[15.9.2.1$^{3,6}$.0$^{20,27}$.0$^{21,25}$]nonacosa-1(26),17,19,22,24,27-hexaene-5-carboxamide Step 1:
6-Bromo-4-hydroxy-7-methoxyquinolin-2(1H)-one To a mixture of 4-bromo-3-methoxyaniline (10 g, 49.5 mmol) and malonic acid (5.15 g, 49.5 mmol) was added POCl$_3$ (5.07 ml, 54.4 mmol) with thorough mixing, and it was then heated to 105° C. After 5 min, the reaction began to bubble vigorously, and eventually formed a hard foam and heating was continued for 1 h. After cooling, water (200 mL) was added and the mixture was stirred for 30 min. The solid was filtered off and washed with water. To the solid was added 2N NaOH (300 mL) and stirring was continued overnight. The remaining solid was filtered off, and EtOH (5 mL) was then added to the filtrate and the basic layer was then acidified with conc. HCl to pH 2. The resulting solid was then filtered off, washed with water. The solid was then transferred to a flask and the remaining water was removed by stripping off EtOH (200 mL×2). The solid was then further dried under high vacuum for 15 h to yield 8.75 g (66%) of the title compound as an off-white solid. LRMS ESI$^+$ (M+H)$^+$ 270.2.

Step 2: 1-tert-butyl 2-methyl (2S,4R)-4-[(6-bromo-7-methoxy-2-oxo-1,2-dihydroquinolin-4-yl)oxy]pyrrolidine-1,2-dicarboxylate To a solution of 1-tert-butyl 2-methyl (2S,4S)-4-{[(4-bromophenyl)sulfonyl]oxy}pyrrolidine-1,2-dicarboxylate (4 g, 8.61 mmol) and the product from Step 1,6-bromo-4-hydroxy-7-methoxyquinolin-2(1H)-one (3.49 g, 12.92 mmol) in NMP (86 ml) under N$_2$ was added Cs$_2$CO$_3$ (8.42 g, 25.8 mmol). The mixture was then heated to 60° C. After 6.5 h, the reaction was extracted with water and EtOAc. The organic layer was extracted with water and brine and dried over MgSO$_4$. The solvent was then removed in vacuo. The crude product (6.5 g) was purified on silica (gradient elution, 0-100% EtOAc/hex and then 0-5% MeOH/DCM) to yield 2.26 g (53%) of the title compound. LRMS ESI$^+$((M-Boc)+H)$^+$ 397.3.

Step 3: 1-tert-butyl 2-methyl (2S,4R)-4-[(7-methoxy-2-oxo-6-vinyl-1,2-dihydroquinolin-4-yl)oxy]pyrrolidine-1,2-dicarboxylate To a solution of the product from Step 2,1-tert-butyl 2-methyl (2S,4R)-4-[(6-bromo-7-methoxy-2-oxo-1,2-dihydroquinolin-4-yl)oxy]pyrrolidine-1,2-dicarboxylate (2.26 g, 4.54 mmol) in EtOH (45.4 mL) was added potassium vinyltrifluoroborate (0.913 g, 6.82 mmol), Et$_3$N (0.950 mL, 6.82 mmol), and PdCl$_2$(dppf)-CH$_2$Cl$_2$ adduct (0.186 g, 0.227 mmol). The mixture was then heated to reflux for 1 h. The EtOH was removed in vacuo and the residue was taken up in EtOAc and extracted with water. The organic layer was dried over MgSO$_4$ and the solvent was removed in vacuo. The crude material was purified on silica gradient elution, 0-5% MeOH/DCM) to yield 2.0 g (99%) of the title compound. LRMS ESI$^+$((M-Boc)+H)$^+$ 345.3.

Step 4: Methyl (4R)-4-[(7-methoxy-2-oxo-6-vinyl-1,2-dihydroquinolin-4-yl)oxy]-L-prolinate hydrochloride To the product from Step 3, 1-tert-butyl 2-methyl (2S,4R)-4-[(7-methoxy-2-oxo-6-vinyl-1,2-dihydroquinolin-4-yl)

oxy]pyrrolidine-1,2-dicarboxylate (2.02 g, 4.54 mmol) was added HCl (4M in dioxane) (22.72 ml, 91 mmol) at r.t. After 1.5 h, the solvent was removed in vacuo. The residue was taken up in Et$_2$O and the solvent was removed in vacuo to yield 1.73 (99%) g of the title compound as a tan solid. LRMS ESI$^+$ (M+H)$^+$ 345.4.

Step 5: Methyl (4R)-1-[(2S)-2-cyclohexyl-2-({[(2,2-dimethylpent-4-en-1-yl)oxy]carbonyl}amino)acetyl]-4-[(7-methoxy-2-oxo-6-vinyl-1,2-dihydroquinolin-4-yl)oxy]-L-prolinate To a solution of the product from Step 4, methyl (4R)-4-[(7-methoxy-2-oxo-6-vinyl-1,2-dihydroquinolin-4-yl)oxy]-L-prolinate hydrochloride (0.84 g, 2.206 mmol) and linker B20, (2S)-cyclohexyl({[(2,2-dimethylpent-4-en-1-yl)oxy]carbonyl}amino)acetic acid (0.689 g, 2.316 mmol) in DMF (2 mL) was added DIPEA (1.156 mL, 6.62 mmol) and HATU (1.090 g, 2.87 mmol). After 15 min, the reaction was complete and 1 N HCl and EtOAc were added. The organic layer was washed with water and brine, dried over MgSO$_4$ and the solvent was removed in vacuo. The crude product was purified on silica (gradient elution, 0-5% MeOH/DCM) to yield 1.65 g of material which still contained HATU residue. This was removed by extracting the material with EtOAc and 1N HCl (4×), water (1×) and brine (1×). The organic layer was dried over MgSO$_4$ and the solvent was removed in vacuo to yield 1.13 g (82%) of the title compound. LRMS ESI$^+$(M+H)$^+$ 624.6.

Step 6: Methyl (2R,4S,7S,14E)-7-cyclohexyl-23-methoxy-12,12-dimethyl-6,9,20-trioxo-3,4,6,7,8,9,12,13,19,20-decahydro-2H,11H-16,18-etheno-2,5-methanopyrido[4,3-k][1,10,3,6]dioxadiazacyclononadecine-4-carboxylate To a degassed (N$_2$ bubbling for 15 min) solution of the product from Step 5, methyl (4R)-1-[(2S)-2-cyclohexyl-2-({[(2,2-dimethylpent-4-en-1-yl)oxy]carbonyl}amino)acetyl]-4-[(7-methoxy-2-oxo-6-vinyl-1,2-dihydroquinolin-4-yl)oxy]-L-prolinate (1.61 g, 2.58 mmol) in DCM (516 mL) was added the Zhan 1b catalyst (0.189 g, 0.258 mmol). After stirring for 24 h at r.t. and 8 h at reflux, conversion was complete. The solvent was removed in vacuo and the product was purified on silica (gradient elution, 0-5% MeOH/DCM) to yield 1.53 g (99%) of the title compound as a greenish solid. LRMS ESI$^+$ (M+H)$^+$ 596.5.

Step 7: Methyl (2R,4S,7S)-7-cyclohexyl-23-methoxy-12,12-dimethyl-6,9,20-trioxo-3,4,6,7,8,9,12,13,14,15,19,20-dodecahydro-2H,11H-16,18-etheno-2,5-methanopyrido[4,3-k][1,10,3,6]dioxadiazacyclononadecine-4-carboxylate To a solution of the product from Step 6, methyl (2R,4S,7S,14E)-7-cyclohexyl-23-methoxy-12,12-dimethyl-6,9,20-trioxo-3,4,6,7,8,9,12,13,19,20-decahydro-2H,11H-16,18-etheno-2,5-methanopyrido[4,3-k][1,10,3,6]dioxadiazacyclononadecine-4-carboxylate (1.53 g, 2.57 mmol) in EtOH (25.7 mL) under N$_2$ was added Pd/C (0.137 g, 0.128 mmol). The atmosphere was then exchanged for H$_2$ and the mixture was stirred for 2 days. At this time conversion was <50%, so Pd/C (0.137 g, 0.128 mmol) was added and stirring was continued for 2 days more. The reaction was then filtered through glass wool and washed with EtOH. The solvent was removed in vacuo to yield 1.42 g (92%) of the title compound as a tan solid. $^1$H NMR (500 MHz, CDCl$_3$): δ 9.87 (s, 1H), 7.36 (s, 1H), 6.51 (s, 1H), 5.77 (s, 1H), 5.29 (d, J 9.5, 1H), 5.11 (s, 1H), 4.66 (dd, J 10.25, 7.5, 1H), 4.57 (d, J 12.0, 1H), 4.40 (t, J 10.0, 1H), 4.33 (d, J 11.0, 1H), 3.93 (m, 1H), 3.88 (s, 3H), 3.76 (s, 3H), 3.30 (d, J 10.5, 1H), 2.98 (m, 1H), 2.72 (m, 1H), 2.15 (m, 2H), 1.89 (m, 2H), 1.75 (m, 3H), 1.67 (m, 1H), 1.47-1.03 (m, 8H), 1.01 (s, 3H), 0.83 (m, 1H), 0.78 (s, 3H). LRMS ESI$^+$ (M+H)$^+$ 598.5.

Step 8: methyl (3R,5S,8S)-8-cyclohexyl-18-methoxy-13,13-dimethyl-7,10-dioxo-22-{[(trifluoromethyl)sulfonyl]oxy}-2,11-dioxa-6,9,21-triazatetracyclo[15.6.2.1$^{3,6}$.0$^{20,24}$]hexacosa-1(24),17,19,20,22,24-hexaene-5-carboxylate To a solution of the product from Step 7, methyl (2R,4S,7S)-7-cyclohexyl-23-methoxy-12,12-dimethyl-6,9,20-trioxo-3,4,6,7,8,9,12,13,14,15,19,20-dodecahydro-2H,11H-16,18-etheno-2,5-methanopyrido[4,3-k][1,10,3,6]dioxadiazacyclononadecine-4-carboxylate (236 mg, 0.395 mmol) in DCM (6 mL) cooled to 0° C. was added pyridine (0.16 mL, 1.97 mmol) and the triflic anhydride (0.1 mL, 0.59 mmol). After 1.5 h, the reaction was diluted with ether and washed with 10% aqueous NaHCO$_3$. The organic layer was dried over Na$_2$SO$_4$ and the solvent was removed in vacuo. The crude product was purified on silica (gradient elution, 20-60% EtOAc/hexanes) to yield the title compound. LRMS ESI$^+$ (M+H)$^+$ 730.1.

Step 9: methyl (3R,5S,8S)-8-cyclohexyl-18-methoxy-13,13-dimethyl-7,10-dioxo-2,11-dioxa-6,9,21,24-tetraazapentacyclo[15.9.2.1$^{3,6}$.0$^{20,27}$.0$^{21,25}$]nonacosa-1(26),17,19,22,24,27-hexaene-5-carboxylate To a mixture of the product from Step 8, methyl (3R,5S,8S)-8-cyclohexyl-18-methoxy-13,13-dimethyl-7,10-dioxo-22-{[(trifluoromethyl)sulfonyl]oxy}-2,11-dioxa-6,9,21-triazatetracyclo[15.6.2.1$^{3,6}$.0$^{20,24}$]hexacosa-1(24),17,19,20,22,24-hexaene-5-carboxylate (254 mg, 0.348 mmol) in THF (4 mL) was added 2,2-dimethoxyethanamine (0.75 mL, 6.96 mmol). The mixture was then heated to 100° C. for 18 h. The crude material was then purified by reverse phase chromatography (gradient elution, 0-100% CH$_3$CN/0.015% TFA in water) to yield the addition product, methyl (3R,5S,8S)-8-cyclohexyl-22-[(2,2-dimethoxyethyl)amino]-18-methoxy-13,13-dimethyl-7,10-dioxo-2,11-dioxa-6,9,21-triazatetracyclo[15.6.2.1$^{3,6}$.0$^{20,24}$]hexacosa-1(24),17,19,20,22,24-hexaene-5-carboxylate, which was taken up in xylenes (8 mL) and acetic acid (2.1 mL) and heated to 140° C. overnight. The solvents were then removed in vacuo and the crude material was then purified by reverse phase chromatography (gradient elution, 0-100% CH$_3$CN/0.015% TFA in water) to yield the title compound. LRMS ESI$^+$ (M+H)$^+$ 621.1.

Step 10: (3R,5S,8S)-8-cyclohexyl-18-methoxy-13,13-dimethyl-7,10-dioxo-2,11-dioxa-6,9,21,24-tetraazapentacyclo[15.9.2.1$^{3,6}$.0$^{20,27}$.0$^{21,25}$]nonacosa-1(26),17,19,22,24,27-hexaene-5-carboxylic acid To a solution of the product from Step 9, methyl (3R,5S,8S)-8-cyclohexyl-18-methoxy-13,13-dimethyl-7,10-dioxo-2,11-dioxa-6,9,21,24-tetraazapentacyclo[15.9.2.1$^{3,6}$.0$^{20,27}$.0$^{21,25}$]nonacosa-1(26),17,19,22,24,27-hexaene-5-carboxylate (100 mg, 0.161 mmol) in THF (4 mL), MeOH (1 mL) and water (1 mL) was added LiOH (39 mg, 1.61 mmol). The mixture was then heated to 50° C. for 1 h and 1N HCl was then added to neutralize the base. The mixture was then extracted with EtOAc, the organic layer was dried over MgSO$_4$, and the solvent was removed in vacuo to yield the title compound. LRMS (M+H)$^+$=607.1.

Step 11: (3R,5S,8S)-8-cyclohexyl-N-((1R,2S)-1-{[(cyclopropylsulfonyl)amino]carbonyl}-2-vinylcyclopropyl)-18-methoxy-13,13-dimethyl-7,10-dioxo-2,11-dioxa-6,9,21,24-tetraazapentacyclo[15.9.2.1$^{3,6}$.0$^{20,27}$.0$^{21,25}$]nonacosa-1(26),17,19,22,24,27-hexaene-5-carboxamide To a solution of the product from Step 10, (3R,5S,8S)-8-cyclohexyl-18-methoxy-13,13-dimethyl-7,10-dioxo-2,11-dioxa-6,9,21,24-tetraazapentacyclo[15.9.2.1$^{3,6}$.0$^{20,27}$.0$^{21,25}$]nonacosa-1(26),17,19,22,24,27-hexaene-5-carboxylic acid (75 mg, 0.124 mmol) in DMF (1 mL) was added acylsulfonamide intermediate A1 (40 mg, 0.15 mmol), DIPEA (0.065 mL, 0.37 mmol), HATU (56 mg, 0.15 mmol), and DMAP (7.5 mg, 0.062 mmol). After 30 min, the mixture was purified directly by reverse phase chromatography (100×30 mm, 0-100% ACN/0.15% aqueous TFA) to give the title compound as a white solid. LRMS (M+H)$^+$=819.2.

Example 39

(3R,5S,8S)-8-cyclohexyl-N-((1R,2R)-1-{[(cyclopropylsulfonyl)amino]carbonyl}-2-ethylcyclopropyl)-18-methoxy-13,13-dimethyl-7,10-dioxo-2,11-dioxa-6,9,21,24-tetraazapentacyclo[15.9.2.1$^{3,6}$.0$^{20,27}$.0$^{21,25}$]nonacosa-1(26),17,19,22,24,27-hexaene-5-carboxamide The title compound was prepared according to the procedure in Example 38 except intermediate A3 was used in place of intermediate A1 in Step 11. LRMS (M+H)$^+$=821.2.

Example 40

(3R,5S,8S)-8-cyclohexyl-N-((1R,2S)-1-{[(cyclopropylsulfonyl)amino]carbonyl}-2-vinylcyclopropyl)-13,13-dimethyl-7,10-dioxo-2,11-dioxa-6,9,21,24-tetraazapentacyclo[15.9.2.1$^{3,6}$.0$^{20,27}$.0$^{21,25}$]nonacosa-1(26),17,19,22,24,27-hexaene-5-carboxamide The title compound was prepared according to the procedure for Example 38, except 4-bromoaniline was used in place of 4-bromo-3-methoxyaniline in Step 1. LRMS (M+H)$^+$=789.2.

Example 41

(3R,5S,8S)-8-cyclohexyl-N-((1R,2S)-1-{[(cyclopropylsulfonyl)amino]carbonyl}-2-vinylcyclopropyl)-13,13-dimethyl-7,10-dioxo-2,11-dioxa-6,9,22,23,25,26-hexaazapentacyclo[15.9.2.1$^{3,6}$.0$^{20,27}$.0$^{21,25}$]nonacosa-1(26),17,19,21,23,27-hexaene-5-carboxamide Step 1: 6-bromo-2,3-dihydrophthalazine-1,4-dione Hydrazine monohydrate (2 ml, 33.0 mmol) was added to a suspension of 4-bromophthalic anhydride (7.5 g, 33.0 mmol) in ethanol (70 ml) and the resulting mixture was stirred at 90° C. for 24 hr. The volume of the reaction mixture was then reduced to half volume under reduced pressure and the residue was treated 0.5 N aq. HCl (20 mL). The title compound precipitated as a white solid and was collected by filtration (4.86 g, 61%); LRMS ESI$^+$ (M+H)$^+$ 241.

Step 2: 6-bromo-1,4-dichlorophthalazine

A solution of 6-bromo-2,3-dihydrophthalazine-1,4-dione from Step 1 (4.86 g, 20.16 mmol) in POCl$_3$ (100 ml) was heated at 120° C. for 16 hr. POCl$_3$ was then removed under reduced pressure and the residue was dissolved in DCM and cold water. Solid NaHCO$_3$ was carefully added till pH=11 was reached, the aq. layer was separated and further extracted with DCM. The combined organic layers were washed with brine, dried (Na$_2$SO$_4$) and concentrated under reduced pressure to give the title compound as a pale yellow solid (4.13 g, 73%); LRMS ESI$^+$ (M+H)$^+$ 279.

Step 3: 8-bromo-6-chloro[1,2,4]triazolo[3,4-a]phthalazine and 9-bromo-6-chloro[1,2,4]triazolo[3,4-a]phthalazine To a solution of 6-bromo-1,4-dichlorophthalazine from Step 2(400 mg, 1.44 mmol) in xylene (5 ml) was added Et$_3$N (0.24 ml, 1.7 mmol) and formic acid hydrazide (95 mg, 1.58 mmol). The resulting mixture was heated at reflux for 16 hr and the volatiles were then removed under reduced pressure. The solid residue was partitioned between DCM and water. The organic layer was dried over Na$_2$SO$_4$, filtered, concentrated under reduced pressure and the residue was purified by SiO$_2$ gel chromatography (eluent: DCM to DCM/MeOH 3%) to give the title compound as a yellow solid mixture of regioisomers (196 mg, 48%); LRMS ESI$^+$ (M+H)$^+$ 284.

Step 4: 1-tert-butyl 2-methyl (2S,4R)-4-[(8-bromo[1,2,4]triazolo[3,4-a]phthalazin-6-yl)oxy]pyrrolidine-1,2-dicarboxylate and 1-tert-butyl 2-methyl (2S,4R)-4-[(9-bromo[1,2,4]triazolo[3,4-a]phthalazin-6-yl)oxy]pyrrolidine-1,2-dicarboxylate To a solution of 1-tert-butyl 2-methyl (2S,4R)-4-hydroxypyrrolidine-1,2-dicarboxylate (170 mg, 0.69 mmol) in DMF (2 ml) at −10 C was added dropwise a 1M solution of lithium bis(trimethylsilyl)amide (0.75 ml, 0.75 mmol) in THF. The resulting mixture was stirred at −10° C. for 1 hr before adding the product from Step 3 (196 mg, 0.69 mmol) in one portion. The mixture was then stirred at rt for 16 hrs, cooled to 0° C., water was added (0.4 mL) and all the volatiles were removed under reduced pressure. The residue was purified by SiO$_2$ gel chromatography (eluent: DCM to DCM/MeOH 3%) to give title compound as a mixture of regioisomers (247 mg, 73%); LRMS ESI$^+$ (M+H)$^+$ 493.

Step 5: 1-tert-butyl 2-methyl (2S,4R)-4-[(8-vinyl[1,2,4]triazolo[3,4-a]phthalazin-6-yl)oxy]pyrrolidine-1,2-dicarboxylate and 1-tert-butyl 2-methyl (2S,4R)-4-[(9-vinyl[1,2,4]triazolo[3,4-a]phthalazin-6-yl)oxy]pyrrolidine-1,2-dicarboxylate To a solution of the product from Step 4 (207 mg, 0.42 mmol) in EtOH (5 mL) was added potassium vinyl-trifluoroborate (65 mg, 0.46 mmol), triethylamine (0.09 ml, 0.63 mmol) and PdCl$_2$(dppf)-CH2Cl$_2$ adduct (17 mg, 0.02 mmol) and the resulting mixture was heated at 90° C. for 1 hr. The volatiles were then removed under reduced pressure, and the residue was purified by SiO$_2$ gel chromatography (eluent:

DCM to DCM/MeOH=98/2) to give the title product as mixture of regioisomers (177 mg, 95%); LRMS ESI+ (M+H)+ 440.

Step 6: Methyl (2S,4R)-4-[(8-vinyl[1,2,4]triazolo[3,4-a]phthalazin-6-yl)oxy]pyrrolidine-2-dicarboxylate hydrochloride and methyl (2S,4R)-4-[(9-vinyl[1,2,4]triazolo[3,4-a]phthalazin-6-yl)oxy]pyrrolidine-2-dicarboxylate hydrochloride To a solution of the product from Step 5 (177 mg, 0.20 mmol) in 4N HCl/dioxane was stirred at rt for 1 hr. The volatiles were then removed under reduced pressure and the resulting residue was used without further purification in the following step; LRMS ESI+ (M+H)+ 340.

Step 7: Methyl (2S,4R)-1-[(2)-2-cyclohexyl-2-({[(2,2-dimethylpent-4-en-1-yl)oxy]carbonyl}amino)acetyl]-4-[(8-vinyl[1,2,4]triazolo[3,4-a]phthalazin-6-yl)oxy]pyrrolidine-2-carboxylate and methyl (2S,4R)-1-[(2)-2-cyclohexyl-2-({[(2,2-dimethylpent-4-en-1-yl)oxy]carbonyl}amino)acetyl]-4-[(9-vinyl[1,2,4]triazolo[3,4-a]phthalazin-6-yl)oxy]pyrrolidine-2-carboxylate To a solution of product from Step 6 (145 mg, 0.19 mmol) in DMF (5 mL) was added intermediate B20 (57.4 mg, 0.19 mmol), DIPEA (0.12 ml, 0.67 mmol) and TBTU (68 mg, 0.21 mmol). The resulting reaction mixture was stirred at rt for 16 hr, diluted with EtOAc and washed with 1N aq HCl, ss NaHCO$_3$ and brine. The organic phase was dried (Na$_2$SO$_4$), concentrated under reduced pressure and purified by SiO$_2$ gel chromatography (eluent: DCM\MeOH 1% to 3%) to give the title compound as a pale orange foam (200 mg, 83%); LRMS ESI+ (M+H)+ 619.

Step 8: methyl (3R,5S,8S,15E)-8-cyclohexyl-13,13-dimethyl-7,10-dioxo-2,11-dioxa-6,9,22,23,25,26-hexaazapentacyclo[15.9.2.1$^{3,5}$.0$^{20,27}$.0$^{21,25}$]nonacosa-1(26),15,17,19,21,23,27-heptaene-5-carboxylate The title compound was prepared from the product obtained in Step 7 (150 mg, 0.12 mmol) as described for Example 1, Step 6. SiO$_2$ gel chromatography (eluent: DCM\MeOH 1% to 3%) gave the title compound as a glass (70 mg, 98%); LRMS ESI+ (M+H)+ 591.

Step 9: methyl (3R,5S,8S)-8-cyclohexyl-13,13-dimethyl-7,10-dioxo-2,11-dioxa-6,9,22,23,25,26-hexaazapentacyclo[15.9.2.1$^{3,5}$.0$^{20,27}$.0$^{21,25}$]nonacosa-1(26),17,19,21,23,27-hexaene-5-carboxylate To a solution of product from Step 8 (70 mg, 0.12 mmol) in MeOH (2 mL) was added 10% Pd/C (13 mg) and the resulting mixture was stirred at rt under hydrogen atmosphere for 16 hr. The catalyst was removed by filtration and the volatiles were removed under reduced pressure. The title compound was used without further purification in the following step; LRMS ESI+ (M+H)+ 592.

Step 10: (3R,5S,8S)-8-cyclohexyl-13,13-dimethyl-7,10-dioxo-2,11-dioxa-6,9,22,23,25,26-hexaazapentacyclo[15.9.2.1$^{3,5}$.0$^{20,27}$.0$^{21,25}$]nonacosa-1(26),17,19,21,23,27-hexaene-5-carboxylic acid To a solution of the product from Step 9 (70 mg, 0.12 mmol) in THF/H$_2$O 1/1 v/v (5 mL) was added LiOH (23 mg, 0.95 mmol) and the resulting mixture was stirred at rt for 1 hr. The reaction mixture was then brought to pH=2 by addition of 0.16 mL of 6N aq. HCl and the volatiles were removed under reduced pressure to give the title compound which was used without further purification in the following step; LRMS ESI+ (M+H)+ 579.

Step 11: (3R,5S,8S)-8-cyclohexyl-N-((1R,2S)-1-{[(cyclopropylsulfonyl)amino]carbonyl}-2-vinylcyclopropyl)-13,13-dimethyl-7,10-dioxo-2,11-dioxa-6,9,22,23,25,26-hexaazapentacyclo[15.9.2.1$^{3,6}$.0$^{20,27}$.0$^{21,25}$]nonacosa-1(26),17,19,21,23,27-hexaene-5-carboxamide To a solution of the product from Step 10 (0.12 mmol) in DMF (3 mL) were added intermediate A1 (32 mg, 0.12), DIPEA (54 mg, 0.07 mmol) and TBTU (42 mg, 0.13 mmol). The resulting reaction mixture was stirred at rt 16 hr and purified directly by reverse phase chromatography (100×30 mm, 40-95% ACN/0.15% aq. TFA) to give the title compound as a white solid product (13 mg; 14%); LRMS ESI+ (M+H)+ 791.1; $^1$H NMR (400 MHz, DMSO-d$_6$): δ 10.45 (s, 1H), 9.38 (s, 1H), 8.87 (s, 1H), 8.37 (d, J 7.9, 1H), 8.16 (s, 1H), 7.89 (d, J 7.9, 1H), 7.79 (s, 1H), 7.67 (d, J 7.7, 1H), 5.77 (s, 1H), 5.59 (m, 1H), 5.22 (d, J 16.4, 1H), 5.10 (d, J 11.4, 1H), 4.59 (d, J 9.6, 1H), 4.31 (m, 1H), 4.23 (d, J 10.7, 1H), 4.15 (m, 1H), 3.99 (d, J 11.8, 1H), 3.26 (m, 1H), 2.94 (m, 1H), 2.86 (m, 1H), 2.68 (m, 1H), 2.59 (m, 1H), 2.19 (m, 1H), 1.92 (s, 2H), 1.84 (m, 1H), 1.74-1.50 (m, 5H), 1.41 (m, 1H), 1.25-0.83 (m, 15H), 0.76 (s, 3H).

Example 42

(3R,5S,8S,15E)-8-cyclohexyl-N-((1R,2S)-1-{[(cyclopropylsulfonyl)amino]carbonyl}-2-vinylcyclopropyl)-13,13-dimethyl-7,10-dioxo-2,11-dioxa-6,9,22,23,25,26-hexaazapentacyclo[15.9.2.1$^{3,5}$.0$^{20,27}$.0$^{21,25}$]nonacosa-1(26),15,17,19,21,23,27-heptaene-5-carboxamide The title compound was prepared as described for Example 41, employing methyl (3R,5S,8S,15E)-8-cyclohexyl-13,13-dimethyl-7,10-dioxo-2,11-dioxa-6,9,22,23,25,26-hexaazapentacyclo[15.9.2.1$^{3,5}$.0$^{20,27}$.0$^{21,25}$]nonacosa-1(26),15,17,19,21,23,27-heptaene-5-carboxylate instead of (3R,5S,8S)-8-cyclohexyl-13,13-dimethyl-7,10-dioxo-2,11-dioxa-6,9,22,23,25,26-hexaazapentacyclo[15.9.2.1$^{3,5}$.0$^{20,27}$.0$^{21,25}$]nonacosa-1(26),17,19,21,23,27-hexaene-5-carboxylic acid in Step 10; white solid; LRMS ESI+ (M+H)+ 789.2; $^1$H NMR (600 MHz, DMSO-d$_6$): δ 10.40 (s, 1H), 9.38 (s, 1H), 8.80 (s, 1H), 8.37 (d, J 8.1, 1H), 8.33 (s, 1H), 8.12 (s, 1H), 7.88-7.86 (m, 2H), 6.60 (d, J 16.0, 1H), 6.45 (m, 1H), 5.63 (s, 1H), 5.53 (m, 1H), 5.16 (d, J 15.9, 1H), 5.05 (d, J 11.4, 1H), 4.77 (d, J 11.5, 1H), 4.36 (d, J 11.7, 1H), 4.21 (m, 1H), 3.95 (d, J 10.4, 1H), 3.25 (m, 1H), 2.92 (m, 1H), 2.78 (m, 1H), 2.28 (m, 1H), 2.12 (m, 1H), 2.03-2.00 (m, 2H), 1.94 (m, 1H), 1.80 (m, 1H), 1.70-1.61 (m, 3H), 1.23-0.92 (m, 15H), 0.82 (s, 3H).

The invention claimed is:

1. A compound of formula (I):

or a pharmaceutically acceptable salt thereof, wherein:

m is 0, 1, 2 or 3; n is 0;

$R^1$ is $CO_2R^5$, $CONR^5SO_2R^5$, $CONR^5SO_2N(R^5)_2$ or tetrazolyl;

$R^a$ is $C_{2-6}$alkylene-$R^2$;

$R^b$ is hydrogen;

or $R^a$ and $R^b$, together with the carbon atom to which they are attached, form a $C_{3-6}$cycloalkyl group, optionally substituted by $R^2$;

$R^2$ is $C_{1-6}$alkyl, $C_{2-6}$alkenyl or $C_{3-8}$cycloalkyl, wherein said alkyl, alkenyl or cycloalkyl is optionally substituted with 1 to 3 halo;

$R^3$ is $C_{1-6}$alkyl, $(CH_2)_{0-3}C_{3-8}$cycloalkyl, $(CH_2)_{0-3}$aryl or $(CH_2)_{0-3}$Het, optionally substituted by halo, $OR^5$, $SR^5$, $N(R^5)_2$, $C_{1-6}$alkyl, $NO_2$, CN, $CF_3$, $NR^5SO_2R^5$, $SO_2N(R^5)_2$, $NHCO_2R^5$, $NHCOR^5$, $NHCONHR^5$, $CO_2R^5$, $C(O)R^5$ or $CON(R^5)_2$;

each W is independently halo, $OR^5$, $C_{1-6}$alkyl, CN, $NO_2$, $CF_3$, $CO_2R^5$ or $CON(R^5)_2$;

each $R^5$ is independently hydrogen, $C_{1-6}$alkyl or $C_{3-8}$cycloalkyl;

Z is O or $NR^6$;

$R^6$ is hydrogen or $C_{1-6}$alkyl;

Y is C=O, $SO_2$ or $CR^cR^d$;

X is O, $NR^e$ or $CR^eR^f$;

$R^c$, $R^d$, $R^e$ and $R^f$ are independently hydrogen, halo or $C_{1-6}$alkyl;

M is $C_{4-12}$alkylene, $C_{4-12}$alkenylene or $C_{4-12}$alkynylene, optionally substituted by $C_{1-6}$alkyl, $(CH_2)_{0-3}C_{3-8}$cycloalkyl, $(CH_2)_{0-3}$aryl, and optionally containing one O or S atom or one NH or $NC_{1-6}$alkyl group, and optionally spiro-fused to a $C_{3-7}$cycloalkyl group, and optionally fused to a 3- to 8-membered ring, which ring optionally contains 1 or 2 heteroatoms selected from N, O and S;

ring A is optionally substituted by $R^4$; and $R^4$ is halo, hydroxy, $C_{1-6}$alkyl, $C_{1-6}$alkoxy, CN, $NO_2$, oxo, $C_{3-8}$cycloalkyl, $N(R^5)_2$, aryl or heteroaryl, optionally substituted by 1 to 8 halo or $C_{1-4}$alkyl.

2. The compound as claimed in claim 1, wherein m is 0 or 1.

3. The compound as claimed in claim 1, wherein $R^1$ is $CONR^5SO_2R^5$ or $CONR^5SO_2N(R^5)_2$.

4. The compound as claimed in claim 1, wherein $R^a$ is $C_{2-5}$alkylene-$R^2$, $R^b$ is hydrogen or $R^a$ and $R^b$, together with the carbon atom to which they are attached, form a $C_{3-5}$cycloalkyl group, optionally substituted by $R^2$, where $R^2$ is $C_{1-6}$alkyl or $C_{2-6}$alkenyl.

5. The compound as claimed in claim 1, wherein $R^3$ is $C_{1-6}$alkyl, or $(CH_2)_{0-3}C_{3-8}$cycloalkyl, optionally substituted by halo, $OR^5$ or $C_{1-6}$alkyl.

6. The compound as claimed in claim 1, wherein M is $C_{4-10}$alkylene, $C_{4-10}$alkenylene or $C_{4-10}$alkynylene, optionally substituted by $C_{1-6}$alkyl or $(CH_2)_{0-3}C_{3-8}$cycloalkyl, and optionally containing one O or S group or one NH or $NC_{1-4}$alkyl group, and optionally fused to a 3- to 8-membered carbocyclic ring.

7. The compound as claimed in claim 1, wherein $R^4$ is halo, hydroxy, $C_{1-6}$alkyl, $C_{1-6}$alkoxy, CN, $C_{3-8}$cycloalkyl or aryl.

8. The compound as claimed in claim 1 which is selected from:
- (2R,4S,7S)-7-cyclohexyl-N-((1R,2S)-1-{[(cyclopropylsulfonyl)amino]carbonyl}-2-vinylcyclopropyl)-12,12-dimethyl-6,9-dioxo-3,4,6,7,8,9,12,13,14,15-decahydro-2H,11H-16,18-(ethanediylidene)-2,5-methano[1,10,3,6]dioxadiazacyclononadecino[11,12-b]quinoline-4-carboxamide,
- (2R,4S,7S,14E)-21-cyano-7-cyclopentyl-N-((1R,2S)-1-{[(cyclopropylsulfonyl)amino]carbonyl}-2-vinylcyclopropyl)-25-methoxy-12,12-dimethyl-6,9-dioxo-3,4,6,7,8,9,12,13-octahydro-2H,11H-16,18-(ethanediylidene)-2,5-methano[1,10,3,6]dioxadiazacyclononadecino[11,12-b]quinoline-4-carboxamide,
- (2R,4S,7S)-21-cyano-7-cyclopentyl-N-((1R,2S)-1-{[(cyclopropylsulfonyl)amino]carbonyl}-2-vinylcyclopropyl)-25-methoxy-12,12-dimethyl-6,9-dioxo-3,4,6,7,8,9,12,13,14,15-decahydro-2H,11H-16,18-(ethanediylidene)-2,5-methano[1,10,3,6]dioxadiazacyclononadecino[11,12-b]quinoline-4-carboxamide,
- (2R,4S,7S)-7-cyclopentyl-N-((1R,2S)-1-{[(cyclopropylsulfonyl)amino]carbonyl}-2-vinylcyclopropyl)-25-methoxy-12,12-dimethyl-6,9-dioxo-3,4,6,7,8,9,12,13,14,15-decahydro-2H,11H-16,18-(ethanediylidene)-2,5-methano[1,10,3,6]dioxadiazacyclononadecino[11,12-b]quinoline-4-carboxamide,
- (2R,4S,7S)-7-cyclopentyl-N-((1R,2S)-1-{[(cyclopropylsulfonyl)amino]carbonyl}-2-vinylcyclopropyl)-25-methoxy-12,12,21-trimethyl-6,9-dioxo-3,4,6,7,8,9,12,13,14,15-decahydro-2H,11H-16,18-etheno-2,5-methano[1,10,3,6]dioxadiazacyclononadecino[11,12-b]quinoline-4-carboxamide,
- (3 aR,7S,10S,12R,24aR)-7-cyclohexyl-N-((1R,2S)-1-{[(cyclopropylsulfonyl)amino]carbonyl}-2-vinylcyclopropyl)-25-methoxy-5,8-dioxo-1,2,3,3a,5,6,7,8,11,12,22,23,24,24a-tetradecahydro-10H-19,21-etheno-9,12-methanocyclopenta[18,19][1,10,3,6]dioxadiazacyclononadecino[11,12-b]quinoline-10-carboxamide,
- (3 aS,7S,10S,12R,24aS)-7-cyclohexyl-N-((1R,2S)-1-{[(cyclopropylsulfonyl)amino]carbonyl}-2-vinylcyclopropyl)-25-methoxy-5,8-dioxo-1,2,3,3a,5,6,7,8,11,12,22,23,24,24a-tetradecahydro-10H-19,21-etheno-9,12-methanocyclopenta[18,19][1,10,3,6]dioxadiazacyclononadecino[11,12-b]quinoline-10-carboxamide,
- (2R,4S,7S,14E)-20-chloro-7-cyclopentyl-N-((1R,2S)-1-{[(cyclopropylsulfonyl)amino]carbonyl}-2-vinylcyclopropyl)-25-methoxy-12,12-dimethyl-6,9-dioxo-3,4,6,7,8,9,12,13-octahydro-2H,11H-16,18-etheno-2,5-methano[1,10,3,6]dioxadiazacyclononadecino[11,12-b]quinoline-4-carboxamide,
- (2R,4S,7S)-20-chloro-7-cyclopentyl-N-((1R,2S)-1-{[(cyclopropylsulfonyl)amino]carbonyl}-2-vinylcyclopropyl)-25-methoxy-12,12-dimethyl-6,9-dioxo-3,4,6,7,8,9,12,13,14,15-decahydro-2H,11H-16,18-etheno-2,5-methano[1,10,3,6]dioxadiazacyclononadecino[11,12-b]quinoline-4-carboxamide,
- (2R,4S,7S)-7-cyclopentyl-N-((1R,2S)-1-{[(cyclopropylsulfonyl)amino]carbonyl}-2-vinylcyclopropyl)-21-fluoro-25-methoxy-12,12-dimethyl-6,9-dioxo-3,4,6,7,8,9,12,13,14,15-decahydro-2H,11H-16,18-(ethanediylidene)-2,5-methano[1,10,3,6]dioxadiazacyclononadecino[11,12-b]quinoline-4-carboxamide,
- (2R,4S,7S,14E)-7-cyclopentyl-N-((1R,2S)-1-{[(cyclopropylsulfonyl)amino]carbonyl}-2-vinylcyclopropyl)-21,25-dimethoxy-12,12-dimethyl-6,9-dioxo-3,4,6,7,8,9,12,13-octahydro-2H,11H-16,18-(ethanediylidene)-2,5-methano[1,10,3,6]dioxadiazacyclononadecino[11,12-b]quinoline-4-carboxamide, and
- (2R,4S,7S)-7-cyclopentyl-N-((1R,2S)-1-{[(cyclopropylsulfonyl)amino]carbonyl}-2-vinylcyclopropyl)-21,25-dimethoxy-12,12-dimethyl-6,9-dioxo-3,4,6,7,8,9,12,13,14,15-decahydro-2H,11H-16,18-(ethanediylidene)-2,5-methano[1,10,3,6]dioxadiazacyclononadecino[11,12-b]quinoline-4-carboxamide, or pharmaceutically acceptable salts thereof.

9. A compound as claimed in claim 1, wherein:
m is 0 or 1;
$R^1$ is $CONR^5SO_2R^5$ or $CONR^5SO_2N(R^5)_2$;
$R^a$ is $C_{2-5}$alkylene-$R^2$ where $R^2$ is as defined in claim 1, $R^b$ is hydrogen or $R^a$ and $R^b$, together with the carbon atom to which they are attached, form a $C_{3-5}$cycloalkyl group, optionally substituted by $R^2$, where $R^2$ is $C_{1-6}$alkyl or $C_{2-6}$alkenyl;
$R^3$ is $C_{1-6}$alkyl, or $(CH_2)_{0-3}C_{3-8}$cycloalkyl, optionally substituted by halo, $OR^5$ or $C_{1-6}$ alkyl;
Z is O, Y is C=O and X is O or $NR^e$;
M is $C_{4-10}$alkylene, $C_{4-10}$alkenylene or $C_{4-10}$alkynylene, optionally substituted by $C_{1-6}$alkyl or $(CH_2)_{0-3}C_{3-8}$cycloalkyl, and optionally containing one O or S group or one NH or $NC_{1-4}$alkyl group, and optionally fused to a 3- to 8-membered carbocyclic ring;
A is

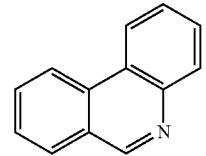 [SMILES: c1ccc2c(c1)cnc1ccccc12]

and which ring is optionally substituted by $R^4$; and
$R^4$ is halo, hydroxy, $C_{1-6}$alkyl, $C_{1-6}$alkoxy, CN, $C_{3-8}$cycloalkyl or aryl.

10. A pharmaceutical composition comprising a compound as claimed in claim 1, or a pharmaceutically acceptable salt thereof, in association with a pharmaceutically acceptable carrier.

11. The pharmaceutical composition as claimed in claim 10, further comprising one or more other agents for the treatment of viral infections or an immunomodulatory agent.

12. The pharmaceutical composition as claimed in claim 11, wherein said one or more other agents for the treatment of viral infections is an antiviral agent.

13. The pharmaceutical composition as claimed in claim 11, wherein said immunomodulatory agent is an α-, β- or γ-interferon.

14. A method of treating infection by hepatitis C virus in a human or animal, comprising administering a compound as claimed in claim 1 or a pharmaceutically acceptable salt thereof.

15. A method of inhibiting hepatitis C virus protease and/or of treating an illness due to hepatitis C virus, the method involving administering to a human or animal subject suffering from the condition a therapeutically effective amount of the pharmaceutical composition claimed in claim 10.

16. A method of inhibiting hepatitis C virus protease and/or of treating an illness due to hepatitis C virus, the method involving administering to a human or animal subject suffering from the condition a therapeutically effective amount of a compound as claimed in claim 1, or a pharmaceutically acceptable salt thereof.

17. A method for manufacturing a medicament for treatment of infection by heptatitis C virus in a human or animal, said method comprising providing a therapeutically effective amount of a compound as claimed in claim 1, or a pharmaceutically acceptable salt thereof, and a pharmaceutically acceptable carrier.

* * * * *